US006649605B2

(12) United States Patent
Olesen et al.

(10) Patent No.: US 6,649,605 B2
(45) Date of Patent: Nov. 18, 2003

(54) TREATMENT OF TENSION-TYPE HEADACHES WITH NMDA RECEPTOR ANTAGONISTS

(75) Inventors: Jes Olesen, Hellerup (DK); Lars Bendtsen, Slagelse (DK); Rigmor Jensen, Virum (DK); Ulf Madsen, Horsholm (DK)

(73) Assignee: Head Explorer A/S, Ballerup (DK)

( * ) Notice: Subject to any disclaimer, the term of this patent is extended or adjusted under 35 U.S.C. 154(b) by 81 days.

(21) Appl. No.: 09/941,855

(22) Filed: Aug. 30, 2001

(65) Prior Publication Data

US 2002/0072543 A1 Jun. 13, 2002

Related U.S. Application Data

(60) Division of application No. 09/304,115, filed on May 4, 1999, now Pat. No. 6,284,794, which is a continuation-in-part of application No. PCT/DK97/00502, filed on Nov. 4, 1997.
(60) Provisional application No. 60/085,413, filed on May 14, 1998, and provisional application No. 60/030,294, filed on Nov. 5, 1996.

(51) Int. Cl.$^7$ ...................... A61K 31/55; A61K 31/675; A61K 31/135
(52) U.S. Cl. ......................... 514/215; 514/82; 514/85; 514/89; 514/216; 514/217; 514/654
(58) Field of Search .............................. 514/82, 85, 89, 514/215, 216, 217, 654

(56) References Cited

U.S. PATENT DOCUMENTS 5,296,225 A     3/1994   Adekunle et al.

FOREIGN PATENT DOCUMENTS

| EP | 0659410 | 6/1995 |
|---|---|---|
| EP | 813873 | 12/1997 |
| WO | 9531195 | 11/1995 |
| WO | 9615782 | 5/1996 |
| WO | 9629326 | 9/1996 |
| WO | 9632386 | 10/1996 |

OTHER PUBLICATIONS

Bach, et al., *Effect of Sulpiride or Paroxetine on Cerebrospinal Fluid Neuropeptide Concentrations in Patients with Chronic Tension–type Headache*, Neuropeptides, vol. 27, pp. 129–136, 1994.
Langemark, et al., *Sulpiride and Paroxetine in the Treatment of Chronic Tension–Type Headache. An Explanatory Double–Blind Trial*, Headache, vol. 34, pp. 20–24, 1994.
Ashina, et al., *Effect of inhibition of nitric oxide synthase on chronic tension–type headache: a randomised crossover trial*, The Lancet, vol. 353, pp. 287–289, Jan. 23, 1999.
Finkel, et al., *Paroxetine is a novel nitric oxide synthase inhibitor*, Psychopharmacol Bull, vol. 32(4), pp. 653–658, 1996.

Olesen, J., *Clinical and pathophysiological observations in migraine and tension–type headache explained by integration of vascular, supraspinal and myofascial inputs*, Pain, (Abstract), vol. 46(2), pp. 125–132, Aug. 1991.
Atkins, C.J., et al., "An Electronic Method for Measuring Joint Tenderness in Rheumatoid Arthritis," *Arthritis And Rheumatism*, 35–4:407–410 (1992).
Ashina, M., et al., "Measurement of Muscle Hardness: A Methodological Study," *Cephalalgia* 18:106–111 (1998).
Ashina, M., et al., "Muscle Hardness in Patients with Chronic Tension–type Headache: Relation to Actual Headache State," *Pain* 79:201–205 (1999).
Aull, S., et al., "Polypragmasie beim Spannungskopfschmerz?," *Wiener Klinische Wochenschrift* 106–6:153–158 (1994).
Bakke, M., et al., "Clinical Significance of Isometric Bite Force Versus Electrical Activity in Temporal and Masseter Muscles," *Scand J Dent Res* 97:539–551 (1989).
Bendtsen, L., "A Non–selective (amitriptyline), but not a Selective (citalopram), Serotonin Reuptake Inhibitor is Effective in the Prophylactic Treatment of Chronic Tension–type Headache," *Journal Of Neurosurgery, And Psychiatry* 61:285–290 (1996).
Bendtsen, L., et al., "Decreased Pain Detection and Tolerance Thresholds in Chronic Tension–type Headache," *Archives Of Neurology* 53:373–376 (1996).
Bendtsen, L., et al., "Evidence of Qualitatively Altered Nociception in Patients with Fibromyalgia," *Arthritis & Rheumatism* 40–1:98–102 (1997).
Bendtsen, L., et al., "Exteroceptive Suppression of Temporal Muscle Activity is Normal in Chronic Tension–Type Headache and not Related to Actual Headache State," *Cephalalgia* 16:251–256 (1996).
Bendtsen, L., et al., "Muscle Palpation with Controlled Finger Pressure: New Equipment for the Study of Tender Myofascial Tissues," *Pain* 59:235–239 (1994).
Bendtsen, L., et al., "Pressue–controlled Palpation: A New Technique Which Increases the Reliability of Manual Palpation," *Cephalalgia* 15:205–210 (1995).
Bendtsen, L., et al., "Qualitatively Altered Nociception in Chronic Myofascial Pain," *Pain* 65:259–264 (1996).
Bendtsen, L., et al., "Quantitatively Changed Noxious Thresholds in Chronic Tension–Type Headache," *Cephalalgia* 15:143 (1995).
Boivie, J., "Central Pain," Textbook Of Pain, Third Edition, Churchill Livingstone, Edinburgh pp. 871–902 (1994).
Bovim, G., "Cervicogenic Headache, Migraine, and Tension–type Headache. Pressure–pain Threshold Measurements," *Pain* 51:169–173 (1992).

(List continued on next page.)

*Primary Examiner*—William R. A. Jarvis
(74) *Attorney, Agent, or Firm*—Iver P. Cooper

(57) ABSTRACT

NMDA receptor antagonists, especially mirtazapine, can be used to treat tension-type headaches.

51 Claims, 22 Drawing Sheets

OTHER PUBLICATIONS

Brennum, J., et al., "Measurement of Human Pressure–pain Thresholds on Fingers and Toes," *Cephalalgia* 9:131–132 (1989).

Brennum, J., et al., "Sumatriptan has no Clinically Relevant Effect in the Treatment of Episodic Tension–type Headache," *European Journal of Neurology* 3:23–28 (1996).

Brennum, J., et al., "The 5–HT$_1$–like Agonist Sumatriptan has a Significant Effect in Chronic Tension–type Headache," *Cephalalgia* 12:375–379 (1992).

Campbell, J.N., et al., "Peripheral Neural Mechanisms of Nociception," Textbook of Pain, Churchill Livinston, Edinburgh pp. 22–45 (1989).

Cervero, F., et al., "Mechanically Evoked Responses of Afferent Fibres Innervating the Guinea–Pig's Ureter: an In Vitro Study," *Journal Of Physiology* 412:245–266 (1989).

Cervero, F., et al., "Visceral Nociceptors: A New World Order?," *Trends Neurosci* 15:374–378 (1992).

Christensen L.V., "Jaw Muscle Fatigue and Pains Induced by Experimental Tooth Clenching: A Review," *Journal Of Oral Rehabilitation* 8:27–36 (1981).

Clark, G.T., et al., "Cross–correlation Between Stress, Pain, Physical Activity, and Temporalis muscle EMG in Tension – type Headache," *Cephalalgia* 15:511–518 (1995).

Clark, G.T., et al., "Jaw Pain and Tenderness Levels During and After Repeated Sustained Maximum Voluntary Protrusion," *Pain* 45:17–22 (1991).

Coderre, T. J., et al., "Contribution of Central Neuroplasticity of Pathological Pain: Review of Clinical and Experimental Evidence," *Pain* 52:259–285 (1993).

Diamond, S., "Efficacy and Safety Profile of Venlafaxine in Chronic Headache," *Headache Quarterly* 6–3:212–214 (1995).

Dickenson, A.H., "Pharmacology of Pain Transmission and Control," *Pain*–An updated review 113–121 (1996).

Drummond, P.D., "Scalp Tenderness and Sensitivity to Pain in Migrain and Tension Headache," *Headache* 27:45–50 (1987).

Dubner, R., et al., "Activity–dependent Neuronal Plasticity Following Tissue Injury and Inflammation," *Trends Neurosci* 15:96–103 (1992).

Fields, H.L., et al., "Central Nervous System Mechanisms of Pain Modulation," Textbook of Pain, Chruchill Livingstone, Edinburgh pp. 243–257 (1994).

Fruhstorfer, H., et al., "Method for Quantitative Estimation of Thermal Thresholds in Patients," *Journal Of Neurology, Neurosurgery, And Psychiatry* 39:1071–1075 (1976).

Gee, N.S., et al., "The Novel Anticonvulsant Drug, Gabapentin (Neurontin), Binds to the $\alpha_2\delta$ Subunit of a Calcium Channel," *Journal Of Biological Chemistry* 271–10:5768–5776 (1996).

Gobel, H., et al., "Pain Sensitivity and Pain Reactivity of Pericranial Muscles in Migraine and Tension–type Headache," *Cephalalgia* 12:142–151 (1992).

Grozdanovic, Z., et al., "Species–independent Expression of Nitric Oxide Synthase in the Sarcolemma Region of Visceral and Somatic Striated Muscle Fibers," *Cell & Tissue Research* 281:493–499 (1995).

Haley, J.E., et al., "Electrophysiological evidence for a Role of Nitric Oxide in Prolonged Chemical Nociception in the Rat," *Neuropharmacology* 31:251–258 (1992).

Hamilton, M., "A Rating Scale for Depression," *J. Neurol. Neurosurg. Psychiat.* 23:56–62 (1960).

Hao, J.X., et al., "Photochemically Induced Transient Spinal Ischemia Induces Behavioral Hypersensitivity to Mechanical and Cold Stimuli, but Not to Noxious–Heat Stimuli, in the Rat," *Experimental Neurology* 118:187–194 (1992).

Hao, J.X., et al., "Treatment of a Chronic Allodynia–like Response in Spinally Injured rats: Effects of Systemically Administered Nitric Oxide Synthase Inhibitors," *Pain* 66:313–319 (1996).

Hatch, J.P., et al., "The use of Elecromyography and Muscle Palpation in the Diagnosis of Tension–type Headache with and without Pericranial Muscle Involvement," *Pain* 49:175–178 (1992).

Hoheisel, U., et al., "Functional Reorganization in the Rat Dorsal Horn During an Experimental Myositis," *Pain* 59:111–118 (1994).

Horikawa, M., et al., "Non–invasive Measurement Method for Hardness in Muscular Tissues," *Medical & Biological Engineering & Computing* 31:623–627 (1993).

Howell, J.N., et al., "Muscle Stiffness, Strength Loss, Swelling and Soreness Following Exercise–induced Injury in Humans," *Journal of Physiology* 464:183–196 (1993).

Hu, J.W., et al., "Stimulation of Craniofacial Muscle Afferents Induces Prolonged Facilitatory Effects in Trigeminal Nociceptive Brain–Stem Neurones," *Pain* 48:53–60 (1992).

Hwang J.H., et al., "Effect of Subarachnoid Gabapentin on Tactile–Evoked Allodynia in a Surgically Induced Neuropathic Pain Model in the Rat," *Regional Anesthesia* 22–3:249–256 (1997).

Hylden, J.L., et al., "Expansion of Receptive Fileds of Spinal Lamina I Projection Neurons in Rats with Unilateral Adjuvant–induced Inflammation:The Conribution of Dorsal Horn Mechanisms," *Pain* 37:229–243 (1989).

Jamal, G.A., et al., "An Improved Automated Method for the Measurement of Thermal Thresholds. 1. Normal Subjects," *Journal Of Neurology, Neurosurgery, And Psychiatry* 48:354–360 (1985).

Janig, W., et al., "Receptive Properties of Sacral Primary Afferent Neurons Supplying the Colon," *Journal Of Neurophysiology* 65–5:1067–1077 (1991).

Jensen, K., et al., "Experimental Pain in Human Temporal Muscle Induced by Hypertonic Saltine, Potassium and Acidity," *Cephalalgia* 12:101–106 (1992).

Jensen, K., et al., "Experimental Toothcleaning in Common Migraine," *Cephalalgia* 5:243–251 (1985).

Jensen, K., et al., "Pain and Tenderness in Human Temporal Muscle Induced by Bradykinin and 5–Hydroxytryptamine," *Peptides* 11:1127–1132 (1990).

Jensen, K., et al., "Pressure–pain threshold in Human Temporal Region. Evaluation of a New Pressure Algometer," *Pain* 25:313–323 (1986).

Jensen, K., et al., "Quantification of Tenderness by Palpation and Use of Pressure Algometers," *Advances In Pain Research And Therapy* 17:165–181 (1990).

Jensen, R., et al., "Improtance of Muscular Disorders in Tension–Type Headache," *Cephalalgia* 17:357 (1997).

Jensen, R., et al., "Initiating Mechanism of Experimentally Induced Tension–type Headache," *Cephalalgia* 16:175–182 (1996).

Jensen, R., "Mechanisms of Spontaneous Tension–type Headaches: An Analysis of Tenderness, Pain Thresholds and EMG," *Pain* 64:251–256 (1995).

Jensen, R., et al., "Muslce Tenderness and Pressure Pain Thresholds in Headache. A Population Study," *Pain* 52:193–199 (1993).

Jensen, R., et al., "Muscular Disorders in Tension–type Headache," *Cephalalgia* 16:97–103 (1996).

Jensen, R., et al., "Muscular Factors are of Importance in Tension–type Headache," (Abstract) 39th Annual Scientific Meeting of American Association for the Study of Headache, New York p. 25 (1997).

Jensen, R., et al., "Muscular Factors are of Importance in Tension–Type Headache," *Headache* 38:10–17 (1998).

Jensen, R., et al., "Quantitative Surface EMG of Pericranial Muscles in Headache. A Population Study," *Electroencephalography And Clinical Neurophysiology* 93:335–344 (1994).

Jensen, R., et al., "Quantitative Surface EMG of Pericranial Muscles. Reproducibility and Variability," *Electronecephalography And Clinical Neurophysiology* 89:1–9 (1993).

Jensen, R., "Variation in Pain Thresholds and Tenderness During Spontaneous Tension–type Headaches," *Cephalalgia* 15:148 (1995).

Kendgen–Miles, D., et al., "Nitric Oxide as a Chemical Link in the Generation of Pain from Veins in Humans," *Pain* 139–142 (1996).

Kobzik, L., et al., "Nitric Oxide in Skeletal Muscle," *Nature* 372:546–548 (1994).

Koltzenburg, M., et al., "The Nociceptor Sensitization by Bradykinin Does Not Depend on Sympathetic Neurons," *Neuroscience* 46:465–473 (1992).

Laird, J.M.A., et al., "Excitability Changes of Somatic and Viscero–Somatic Nociceptive Reflexes in the Decerebrate–spinal Rabbit: Role of NMDA Receptors," *Journal of Physiology* 489–2:545–555 (1995).

LaMotte, R.H., et al., "Hypothesis for Novel Classes of Chemoreceptors Mediating Chemogenic Pain and Itch," Proceedings of the Fifth World congress of Pain, Elsevier Amsterdam pp. 529–535 (1988).

Langemark, M., et al., "Clinical Characterization of Patients with Chronic Tension Headache," *Headache* 28:590–596 (1988).

Langemark, M., et al., "Pericranial Tenderness in Tension Headache," *Cephalalgia* 7:249–255 (1987).

Lnagemark, H., et al., "Pressure Pain Thresholds and Thermal Nociceptive thresholds in Chronic Tension–type Headache," *Pain* 38:203–210 (1989).

Langemark, M., et al., "Sulpiride and Paroxetine in the Treatment of chronic Tension–type Headache. A Comparative Double–blind Study," *Headache* 9–10:398–399 (1989).

Langemark, M., et al., "Temporal Muscle Blood Flow in Chronic Tension–type Headache," *Arch. Neurol* 47:654–658 (1990).

LeBars, D., et al., "Diffuse Noxious Inhibitory Controls (DNIC).I. Effects on Dorsal horn Convergent Neurons in the Rat," *Pain* 6:283–304 (1979).

Levine J., et al., "Inflammatory Pain," Textbook of Pain, Third Edition, Churchill Livingstone, Edinburgh pp. 45–56 (1994).

Lipchik, G.L., et al., "Central and Peripheral Mechanisms in Chronic Tension–type Headache," *Pain* 64:467–475 (1996).

Lipchik, G.L., et al., "Pericranial Muscle Tenderness and Exteroceptive Suppresion of Temporalis Muscle–Activity: A Blind Study of Chronic Tension–type Headache," *Headache* 37:368–376 (1997).

Lous, I., et al., "evaluation of Pericranial Tenderness and Oral Function in Patients with Common Migraine, Muscle Contraction Headache and 'Combination Headache'," *Pain* 12:385–393 (1982).

Magerl, W., et al., "Secondary Hyperalgesia and Perceptual Wind–up Following Intradermal Injection of Capsaicin in Humans," *Pain* 74:257–268 (1998).

Magni, G., et al., "Chronic Musculosketal Pain and Depressive Symptoms in the General Population. An Analysis of the 1st National Health and Nutrition Examination Survey Data," *Pain* 43:299–307 (1990).

Magnusson T., et al., "Signs and Symptoms of Mandibular Dysfunction After Introduction of Experimental Balancing–side Interferences," *Acts Odontol Scand* 42:129–135 (1984).

Mao, J., et al., "The Inhibition of Nitric Oxide–activated Poly (ADP–ribose) Synthetase Attenuates Transsynaptic Alteration of Spinal Cord Dorsal Horn Neurons and Neuropathic Pain in the Rat," *Pain* 72:355–366 (1997).

Matthews, J.N.S., et al., "Analysis of Serial Measurements in Medical Research," *BMJ* 300:230–235 (1990).

Mayer, E.A., et al., "Basic and Clinical Aspects of Visceral Hyperalgesia," *Gastroenterology* 107:271–293 (1994).

McMahon, S.B., et al., "Central heperexcitability Triggered by Noxious Inputs," *Current Opinion in Neurobiology* 3:602–610 (1993).

Meller, S.T., et al., "Nitric Oxide (NO) and Nociceptive Processing in the Spinal Cord," *Pain* 52:127–136 (1993).

Meller, S.T., et al., "Production of endogenous nitric Oxide and Activation of Soluble Guanylate Cyclase are Required for N–methyl–D–aspartate–produced Facilitation of the Nociceptive Tail–flick Reflex," *European Journal Of Pharmacology* 214:93–96 (1992).

Meller, S.T., et al., "The Role of nitric Oxide in the Development and Maintenance of the Hyperalgesia Produced by Intraplantar Injection of Carrageenan in the Rat," *Neuroscience* 60–2:367–374 (1994).

Mense, S., et al., "Nociception From Skeletal Muscle in Relation to Clinical Muscle Pain," *Pain* 54:241–289 (1993).

Meyer, R.A., et al, "Peripheral Neural Mechanisms of Nociception," Textbook of Pain pp. 13–14 (1994).

Moncada, S., et al., "Nitric Oxide: Physiology, Pathophysiology, and Pharmacology," *Pharmacol Rev* 43:109–142 (1991).

Myers, D.E., et al, "Head Pain as a Result of Experimental Ischemic Exercise of the Temporalis Muscle," *Headache* 23:113–116 (1983).

Nakamura, A., et al., "Involvement of Endogenous Nitric Oxide in the Mechanism of Bradykinin–induded Peripheral Hyperalgesia," *British Journal Of Pharmacology* 117:407–412 (1996).

Ness, T.J., et al., "Quantitative Comparison of Inhibition of Visceral and Cutaneous Spinal Nociceptive Transmission from the Midbrain and Medulla in the Rat," *Journal Of Neurophysiology* 58–4:850–865 (1987).

Norregaard, J., et al., "Pressure and Heat Pain Thresholds and Tolerances on Patients with Fibromyalgia," *Journal of Musculoskeletal Pain* 5–2:43–53 (1991).

Olesen, J., et al., "Getting Away From Simple Muscle Contraction as a Mechanism of Tension–type Headache," *Pain* 46:123–124 (1991).

Olesen, J., et al., "Nitric Oxide Supersensitivity: A Possible Molecular Mechanism of Migraine Pain," *Neuroreport* 4–8:1027–1030 (1993).

Ostergaard, S., et al., "Comparison of First Degree Relatives and Spouses of People with Chronic Tension Headache," *BMJ* 314:1092–1093 (1997).

Paiva, T., et al., "Effects of Frontalis EMB Biofeedback and Diazepam in the Treatment of Tension Headache," *Headache* 22:216–220 (1982).

Pedersen, J.L., et al., "Hyperalgesia and Temporal Summation of Pain After Heat Injury in Man," *Pain* 74:189–197 (1998).

Persson, J., et al., "Beneficial Effects of Ketamine in a Chronic Pain State with Allodynia, Possibly Due to Central Sensitization," *Pain* 60:217–222 (1995).

Petersen, K., L., et al., "Evaluation of Pericranial Myofascial Mociception by Pressure Algometry. Producibility and Factors of Variation," *Cephalalgia* 12:33–37 (1992).

Pfaffenrath, V., et al., "Efficacy and Tolerability of Amitriptylinoxide in the Treatment of Chronic Tension–type Headache: A Multi-centre Controlled Study," *Cephalalgia* 14:149–155 (1994).

Pikoff, H., "Is the Muscular Model of Headache Still Viable? A Review of Conflicting Data," *Headache* 24:186–198 (1984).

Price, D.D., et al., "The N–menthyl–$_D$–aspartate Receptor Antagonist Dextromethorphan Selectively Reduces Temporal Summation of Second Pain in Man," *Pain* 59:165–174 (1994).

Rang, H.P., et al., "Nociceptive Peripheral Neurons: Cellular Properties," Textbook of Pain, Third Edition, Churchill Livingstone, Edinburgh pp. 57–78 (1994)l.

Rasmussen, B.K., et al., "Epidemiology of Headache in a General Population–A Prevalence Study," *J Clin Epidemiol* 44–11:1147–1157 (1991).

Rasmussen, B.K., et al., "Impact of Headache on Sickness Absence and Utilisation of Medical Services: A Danish Population Study," *Journal Of Epidemiology And Community Health* 46:443–446 (1992).

Rasmussen, B.K., et al., "Migraine and Tension–type Headache in a General Population: Precipitating Factors, Female Hormones, Sleep Pattern and Relation to Lifestyle," *Pain* 53:65–72 (1993).

Rees, D.D., et al., "Characterization of Three Inhibitors of Endothelial Nitric Oxide Synthase in vitro and in vivo," *Br. J. Pharmacol.* 101:746–752 (1990).

Roberts. M.H.T., "5–Hydroxytryptamine in Nociception and Antinociception," 5–Hydroxytryptamine Mechanisms in Primary Headaches, Raven Press, New York pp. 69–76 (1992).

Roche, A.K., et al., "A Nitric Oxide Synthesis Inhibitor (L–NAME) Reduces Licking Behavior and Fos–labeling in the Spinal Cord of Rats During Formalin–induced Inflammation," *Pain* 66:331–341 (1996).

Rosner, H., et al., "Gabapentin Ajunctive Therapy in Neuropathic Pain States," *The Clinical Journal Of Pain* 12:56–58 (1996).

Russle, M.B., et al., "Presentation of a New Instrument: The Diagnostic Headache Diary," *Cephalalgia* 12:369–374 (1992).

Sakai, F., et al., "Pericranial Muscle Hardness in Tension–type Headache," *Brain* 118:523–531 (1995).

Sandrini, G., et al., "Comparative Study with EMG, Pressure Algometry and Manual palpation in Tension–type Headache and Migraine," *Cephalalgia* 14:451–457 (1994).

Schoenen, J., et al., "Cephalic and Extracephalic Pressure Pain Thresholds in Chronic Tension–type Headache," *Pain* 47:145–149 (1991).

Schoenen, J., et al., "Exteroceptive Suppression of Temporalis Muscle Activity in Chronic Headache," *Neurology* 37:1834–1836 (1987).

Schoenen, J., et al., "Multiple Clinical and Paraclinical Analyses of Chronic Tension–type Headache Associated or Unassociated With Disorder of Pericranial Muscles," *Cephalalgia* 11:135–139 (1991).

Shimoyama N., et al., "Spinal Gabapentin is Antinociceptive in the Rat Formalin Test," *Neuroscience Letters* 222:65–67 (1997).

Shukla R., et al., "Alprazolam in Chronic Tension Type Headache," *JAPI* 44–9:641–644 (1996).

Southan, G.J., et al., "Selective Pharmacological Inhibition of Distinct Nitric Oxide Synthase Isoforms," *Biochemical Pharmacology* 51:383–394 (1996).

Soyka, D., "Der Spannungskopfschmerz," *Fortbildung* 87–6:477–481 (1993).

Stevens, M.B., "Tension–type Headaches," *American Family Physician* 47–4:799–805 (1993).

Torebjork, H.E., et al., "Central Changes in Prcessing of Mechanoreceptive Input in Capsaicin–induced Secondary Hyperalgesia in Humans," *Jounral Of Physiology* 448:765–780 (1992).

Torebjork, H.E., et al., "Peripheral Neural Correlates of Magnitude of Cutaneous Pain and Hyperalgesia: Simultaneous Recordings in Humans of Sensory Judgements of Pain and Evoked Responses in Nociceptors with C–fibers," *Journal Of Neurophysiology* 51–2:325–339 (1984).

Ulrich, V., et al., "A Comparison of Tension–type Headache in Migraineurs and in Non–Migraineurs: A Population–based Study" (1980).

Wall, P.D., et al., "Muscle But not Cutaneous C–afferent Input Produces Prolonged Increases in the Excitability of the Flexion Reflex in the Rat," *J. Physiol.* 356:443–458 (1984).

Wall, P.D., "The Presence of Ineffective Synapses and The Circumstances Which Unmask Them," *Phil. Trans. R. Soc. Lond. B.* 278:361–372 (1977).

Wanman, A., et al., "Headache and dysfunction of the Masticatory Stysem in Adolescents," *Cephalalgia* 6:247–253 (1986).

Willer, J.C., et al., "Phycophysical and electrophysiological Approaches to the Pain–relieving Effects of Heterotropic Nociceptie Stimuli," *Brain* 107:1095–1112 (1984).

Woolf C.J., et al., "Dynamic Alterations in the Cutaneous Mechanoreceptive Fields of Dorsal Horn Neurons in the Rat Spinal Cord," *Journal Of Neuroscience* 10–8:2717–2726 (1990).

Woolf, C.J., "Evidence for a Central Component of post–Injury Pain Hypertensitivity," *Nature* 306:686–688 (1983).

Woolf, C.J., "The Dorsal Horn: State–dependent Sensory Processing and the Generation of Pain," Textbook of Pain, Third Edition, chruchill Livingston, Edinburgh pp. 101–112 (1994).

Woolf, C.J., "The Induction and Maintenance of Central Sensitization is Dependent on N–methyl–$_D$–aspartic Acid Receptor Activation; Implications for the Treatment of post–injury Pain Hypersensitivity States," *Pain* 44:293–299 (1991).

Woolf, C.J., et al., "The Pathophysiology of Chronic Pain— Increased Sensitivity to Low Threshold Aβ–fibre Inputs," *Curr Opin Neurobiol* 4:525–534 (1994).

Woolf, C.J., et al., "Peripheral Nerve Injury triggers Central Sprouting of Myelinated Afferents," *Nature* 355:75–78 (1992).

Woolf, C.J., et al., "Windup and Central Sensitization are Not Equivalent," *Pain* 66:105–108 (1996).

Worz, R., et al., "Flupirtine Versus Placebo in Chronic Tension–type Headache," *Headache Quaterly* 7–1:30–38 (1996).

Yaksh, T.L., et al., "Central Pharmacology of Nociceptive Transmission," Textbook of Pain, Third Edition, Churchill Livingstone, Edinburgh pp. 165–200 (1994).

Yarnitsky, D., et al., "Heat Pain Thresholds: Normative Data and Repeatability," *Pain* 60:329–332 (1995).

Yu, X.M., et al., "Differential Effects of Cutaneous and Deep Application of Inflammatory Irritant on Mechanoreceptive Field Properties of Trigeminal Brain Stem Nociceptive Neurons," *Journal of Neurophysiology* 70–4:1704–1701 (1993).

Yu, X.M., et al., "Response Properties and Descending Control of Rat Dorsal Horn Neurons with Deep Receptive Fields," *Neuroscience* 39:823–831 (1990).

Zhang, X., et al., "A Closed–loop System for Maintaining Constant Experimental Muscle Pain in Man," *IEEE Trans Biomed Eng* 40–4:344–352 (1993).

Headache Classification Committee of the International Headache Society. Classification and Diagnostic Criteria for Headache Disorders, Cranial Neuralgias and Facial Pain. *Cephalalgia* 8 (sppl. 7):1–96 (1988).

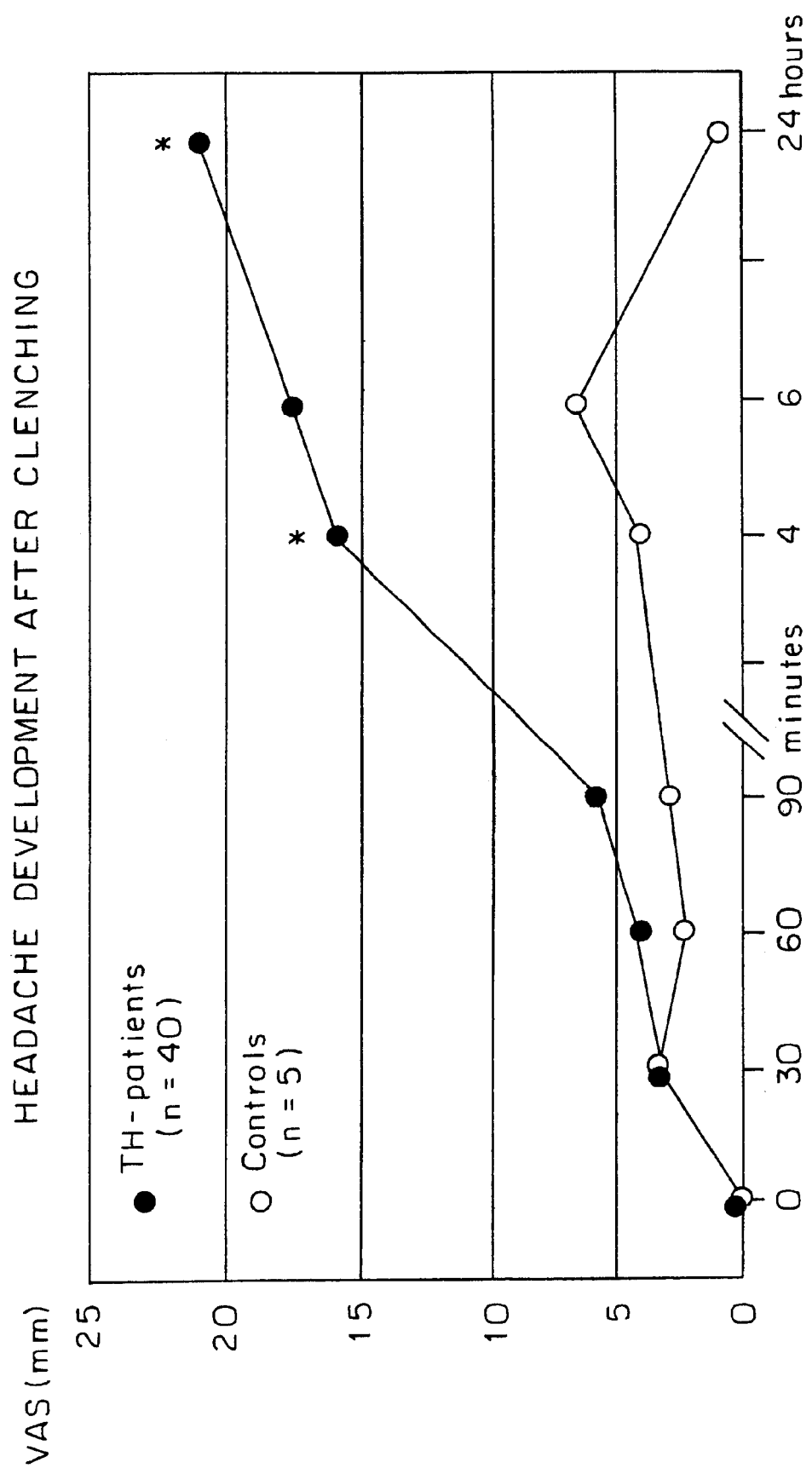

TREATMENT OF TENSION-TYPE HEADACHES WITH NMDA RECEPTOR ANTAGONISTS

This application is a divisional of application Ser. No. 09/304,115, filed May 4, 1999, now U.S. Pat. No. 6,284,794, which is a nonprovisional claiming the benefit under 35 USC §119(e) of provisional Serial No. 60/085,413, filed May 14, 1998. This application is also a continuation-in-part of PCT/DK97/00502, filed Nov. 4, 1997, a PCT application designating the United States, which is a nonprovisional claiming the benefit under 35 USC §119(e) of provisional Serial No. 60/030,294, filed Nov. 5, 1996. All of the above applications are hereby incorporated by reference in their entirety.

FIELD OF THE INVENTION

The present invention relates to a method of treatment or prevention of tension-type headache in a human in need of such treatment. In particular, the invention relates to a method of treatment of tension-type headache comprising the administration of an agent or agents effective for the prevention or reduction of central sensitization

GENERAL BACKGROUND

Types of Clearly Defined Headache Disorders

Previously, headache disorders were not clearly distinguished and it was widely believed that they formed part of a continuum and were strongly related. In 1988, The International Headache Society, (IHS) via its ad hoc committee on classification published a document entitled Classification and Diagnostic Criteria for Headache Disorders, Cranial Neuralgias and Facial Pain (Classification and Diagnostic Criteria for Headache Disorders, 1988). A new entity was here defined by name of tension-type headache. This entity was practically the same as conditions previously called tension headache, muscle contraction headache, psychomyogenic headache and idiopathic headache. The IHS classification also defined a number of other specific headache diseases. Today it therefore gives no meaning to talk about headache in general. It would be the same as to discuss bellyache and chest pain without specifying its type and etiology. Due to the development in diagnostic accuracy research results obtained before 1988 have uncertain validity.

Tension-type headache was subdivided by the IHS Classification Committee into an episodic form occurring less than half of all days and a chronic form occurring half of all days or more. Furthermore, both of these divisions were further subdivided into a form with disorder of pericranial muscle and a form without such disorder. It is thus crucial that research and patents specify which of the subforms are included.

Before the entity of tension-type headache was created, it was widely believed that this kind of headache was caused by muscle ischemia, a concept later disproven by the present inventors (Langemark et al. 1990). The term tension-type headache was created in order to indicate that experts disagreed with the notion of tension-type headache being simply a kind of muscle pain. In fact, the term idiopathic headache was suggested. There is only a moderate co-morbidity with neck pain and low back pain in sufferers of tension-type headache. Furthermore, Electromyography (EMG)-measurements have failed to detect an increase of muscle contraction sufficient to cause pain on a purely mechanical basis in tension-type headache patients whereas central factors such as depression and anxiety have been attributed a significant role. Finally, a genetic factor has recently been shown to be involved in tension-type headache (Østergaard et al. 1996). From the point of view of mechanisms and definition tension-type headache is thus a specific entity which may or may not share mechanisms with muscle pain in the head and in other parts of the body. The classification and diagnostic criteria for tension-type headache are shown in Tables I and II.

TABLE I

Classification of headache disorders cranial neuralgias, and facial pain (Headache Classification Committee 1988).

1. Migraine
2. Tension-type headache
3. Cluster headache and chronic paroxysmal hemicrania
4. Miscellaneous headaches unassociated with structural lesion
5. Headache associated with head trauma
6. Headache associated with vascular disorders
7. Headache associated with non-vascular intra-cranial disorder
8. Headache associated with substances or their withdrawal
9. Headache associated with noncephalic infection
10. Headache associated with metabolic disorder
11. Headache or facial pain associated with disorder of cranium, neck, eyes, nose, sinuses, teeth, mouth or other facial or cranial structures
12. Cranial neuralgias, nerve trunk pain and deafferentation pain
13. Headache not classifiable

TABLE II

Diagnostic criteria for episodic and chronic tension-type headache (Headache Classification Committee 1988)

II.1. Episodic tension-type headache
A. At least 10 previous headache episodes fulfilling criteria B-D listed below.
   Number of days with such headache<180/year (<15/month)
B. Headache lasting from 30 minutes to 7 days
C. At least 2 of the following pain characteristics:
   1. Pressing/tightening quality
   2. Mild or moderate severity (may inhibit, but does not prohibit activities)
   3. Bilateral location
   4. No aggravation by walking stairs or similar routine physical activity
D. Both of the following:
   1. No nausea or vomiting (anorexia may occur)
   2. Photophobia and phonophobia are absent, or one but not the other is present
E. At least one of the following:
   1. History, physical and neurological examinations do not suggest one of the disorders listed in groups 5–11
   2. History and/or physical and/or neurological examinations do suggest such disorders, but they are ruled out by appropriate investigations
   3. Such disorders are present, but tension-type headache does not occur for the first time in close temporal relation to the disorder
II.2. Chronic tension-type headache
A. Average headache frequency 15 days/month (180 days/year) for 6 months fulfilling criteria B–D listed below
B. At least 2 of the following pain characteristics:
   1. Pressing/tightening quality
   2. Mild or moderate severity (may inhibit, but does not prohibit activities)
   3. Bilateral location
   4. No aggravation by walking stairs or similar routine physical activity
C. Both of the following:
   1. No vomiting
   2. No more than one of the following:
      Nausea, photophobia or phonophobia

TABLE II-continued

Diagnostic criteria for episodic and chronic tension-type
headache (Headache Classification Committee 1988)

D. At least one of the following:
  1. History, physical and neurological examinations do not suggest one of the disorders listed in groups 5–11
  2. History and/or physical and/or neurological examinations do suggest such disorders, but they are ruled out by appropriate investigations
  3. Such disorders are present, but tension-type headache does not occur for the first time in close temporal relation to the disorder Epidemiological studies done by the inventors have shown that chronic tension-type headache affects three per cent of the population at any given time, the lifetime prevalence being as high as six per cent (Rasmussen et al. 1991). Severe episodic tension-type headache defined as persons having headache twice a week or more occurs in approximately ten per cent of the population. Thus, tension-type headache is a serious problem with significant socio-economic implications, involving enormous loss of workdays and quality of life.

Epidemiological studies done by the inventors have shown that chronic tension-type headache affects three percent of the population at any given time, the lifetime prevalence being as high as six percent (Rasmussen et al. 1991). Severe episodic tension-type headache defined as persons having headache twice a week or more occurs in approximately ten percent of the population. Thus, tension-type headache is a serious problem with significant socio-economic implications, involving enormous loss of workdays and quality of life.

Previous Findings in General Pain Physiology and Pain Pharmacology

The possible pathogenic mechanisms of tension-type headache have previously been studied and discussed by Langemark et al. (Langemark et al. 1987, 1988, 1989) and by the group of Jean Schoenen (Schoenen et al. 1937, 1991a, b). The latter group have mainly focused on electrophysiological recordings as electromyography, and the jaw opening reflex as reflected by the so-called exteroceptive silent period (ES2) (Schoenen et al. 1987). On the basis of shortened ES2 periods in patients with chronic tension-type headache compared to healthy controls a limbic dysfunction was suggested, but these results have later been disproven by more systematic investigations (Bendtsen et al. 1996a, Lipchik et al 1996, Zwart and Sand, 1996). Schoenen and other groups have also studied mechanical pain thresholds on the extremities as well as in the cranial region and decreased mechanical pain thresholds in severely affected patients with chronic tension-type headache were reported (Schoenen et al. 1991a, Langemark et al. 1989), whereas patients with the episodic form of tension-type headache are reported to have normal thresholds compared to healthy controls (Hatch et al. 1992, Goebel et al. 1992, Jensen et al. 1993b). These authors suggested that central mechanisms may be involved in the chronic subform and that the peripheral mechanisms played a role in the episodic form, but provided no further clues or arguments about the underlying mechanisms. One more recent congress presentation and two scientific papers by the present inventors have focused on the sensory mechanisms in tension-type headache as decreased thresholds and tolerances were found in and outside the head of patients with chronic tension-tape headache indicating a generally increased sensitivity to noxious and innocuous stimuli (Bendtsen et al. 1995b, 1996b and 1996c). Similarly a congress report and a scientific paper present data from patients studied during and outside a spontaneous tension-type headache episode (Jensen et al. 1995a and 1995b). Muscle tenderness was increased during the headache episode, whereas mechanical pain thresholds remained unchanged and thermal pain tolerance decreased. It was concluded that a peripheral sensitization may be one of the primary sources of pain and that central sensitization may contribute to and maintain the pain in chronic tension-type headache. However, these data did not provide any further clues for more specific localizations of the sensitization, could not lead to a precise experimental model and finally did not lead to guidance for specific treatment of tension-type headache.

Peripheral Induction of Central Sensitization

One of the most exciting developments in pain research over the past decades has been the recognition that the response generated by the somatosensory system to a defined input is not fixed or static. In particular, the increased knowledge on central sensitization, i.e. increased excitability of neurons in the central nervous system, has been a major breakthrough in the understanding of chronic pain. In 1983 Woolf and colleagues (Woolf 1983) demonstrated for the first time that a prolonged noxious input from the periphery is capable of sensitizing spinal dorsal horn neurons. It has later been demonstrated that the central sensitization is induced by repetitive C-fiber, but not A-fiber, input (Yaksh and Malmberg 1994). In the sensitized state, a low-intensity stimulus can generate pain, the phenomenon of allodynia. The low-intensity stimulus is mediated via low-threshold afferents, A-b-fibers, which do not normally mediate pain, and it has been suggested that the major cause of increased pain sensitivity in the chronic pain condition is an abnormal response to A-b-sensory input (Woolf and Doubell 1994). The original findings by Woolf and colleagues on spinal dorsal horn sensitization have later been confirmed by numerous independent laboratories (Mense 1993), and a similar sensitization of trigeminal brainstem nociceptive neurons following stimulation of craniofacial muscle afferents has been reported by Hu et al. (Hu et al. 1992). While central sensitization may be of relevance in many different chronic pain conditions it is particular likely in muscle pain, because input from muscle nociceptors is more effective in inducing prolonged changes in the behavior of dorsal horn neurons than is input from cutaneous nociceptors (Wall and Woolf 1984).

SUMMARY OF THE INVENTION

The inventors of the present invention have discovered that the central nervous system is sensitized in patients suffering from increased myofascial pain in connection with tension-type headache because of prolonged nociceptive input from myofascial tissues. The present inventors were then able to devise, for the first time, an effective treatment of tension-type headache, which comprises interacting with neuronal transmission connected with nociception so as to prevent or reduce central sensitization.

A better understanding of the principle of the invention can be derived from the detailed description of the scientific background in the scientific section below.

SCIENTIFIC SECTION

Previous Findings in General Pain Physiology and Pain Pharmacology and Previous Findings in Tension-Type Headache Pain physiology and pain pharmacology have mostly been elucidated in animal studies. There are, however, no animal models with any proven validity in tension-type headache. Furthermore, these animal experimental studies are done in anaesthetized animals while the sensation of pain by definition can only occur in awake beings. Most of the experiments are also of an acute nature stimulating for milliseconds and recording responses for seconds, minutes or hours and are therefore of uncertain validity for chronic tension-type headache. Finally, only few studies have been done on myofascial tissues projecting via the trigeminal nerve while the huge body of knowledge otherwise available deals with mechanisms of the spinal cord. None of the experimental animal studies mention any form of headache, neither do they suggest that the results of these studies may be utilized for the treatment of tension-type headache. However, after the crucial findings leading to the present invention were made, it is clear that the implications of the findings in relation to general pain physiology can also be utilized in relation to tension-type headache.

With respect to medicinal treatment of tension-type headache, the prior art mentions a variety of substances. The substance Flupirtin (ethyl 2-amino-6-(4-fluorobenylamino)-3-pyridylcarbamate), which is suggested to work as an NMDA glutamate receptor antagonist (Schwartz et al. 1981), has been suggested for use in the treatment of chronic or episodic tension-type headache, as disclosed in EP 0 659 410 A2, and according to Wörz et al., 1996, it has shown positive effects. However, in these documents the substance is described as a muscle relaxant, and the mechanism by which it is proposed to exert its effect in the treatment of various conditions, including tension-type headache, is by lowering muscle tension. Thus, as opposed to the present inventors, the prior art understands and explains tension-type headache as a condition directly and primarily caused by muscle tension. WO 96/32386 concerns arylglycinamide derivatives which are antagonists of neurokinins, and these compounds are broadly claimed for use in the treatment of a wide variety of conditions in which neurokinins are supposed to be implicated. Tension-type headache is mentioned as such a condition, but there is no indication of what the mechanism of neurokinin involvement might be. For all the above-mentioned prior art documents, it can be said that the concept of central sensitization in relation to tension-type headache, as introduced by the present inventors, is not described or contemplated at all. Indeed, the prior art does not appear to be concerned with the underlying physiological mechanisms of tension-type headache, but seems to reflect presently held notions of pain physiology in general.

In connection with the present invention, the term "arylglycinamide derivative as disclosed in WO 96/32386" means a compound as defined in any of claims 1–17 of WO 96/32386. As appears from the claims herein, these arylglycinamide derivatives are excluded from the definitions of all aspects of the present invention. The excluded arylglycinamide derivatives of claims 1–17 of WO 96/32386 are all comprised by the definition given in claim 1 of WO 96/32386. Thus, whenever reference is made to an "arylglycinamide derivative as disclosed in WO 96/32386", this means an arylglycinamide derivative covered by the definition of claim 1 of WO 96/32386, that is:

Arylglycinamide derivatives of the general formula I

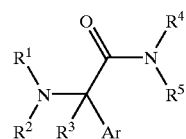

and their pharmaceutically acceptable salts, in which

Ar is unsubstituted or 1–5 times substituted phenyl, or unsubstituted or 1 or 2 times substituted naphtyl [the substituents of phenyl and naphthyl independently of each other being halogen (F, Cl, Br, J), OH, $(C_1-C_4)$ alkyl, $O-(C_1-C_4)$alkyl, $CF_3$, $OCF_3$ or $NR^9R^{10}$ (wherein $R^9$ and $R^{10}$ independently of each other a are H, methyl or acetyl)], or Ar is phenyl substituted with $-OCH_2O-$ or $-O(CH_2)_2O-$;

$R^1$ and $R^2$ together with the N to which they are bound form a ring of the formula

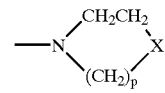

wherein p is 2 or 3,

X means oxygen, $N(CH_2)_nR^6$ or $CR^7R^8$, wherein n is 0, 1 or 2, $R^6$ is $(C_3-C_7)$cycloalkyl, phenyl or naphthyl, each phenyl optionally being 1–3 times substituted with halogen (F, Cl, Br, J), $(C_1-C_4)$alkyl, $O-(C_1-C_4)$alkyl, $CF_3$, $OCF_3$ or $NR^{15}R^{16}$ (wherein $R^{15}$ and $R^{16}$ independently of each other are H, methyl or acetyl);

$R^7$ and $R^8$ have one of the following meanings a) when $R^3$ is unsubstituted or substituted phenyl, then $R^7$ and $R^8$ are H, b) when is $R_8$ is H, $-CONH_2$, $-NHC(O)CH_3$, $-N(CH_3)C(O)CH_3$, CN,

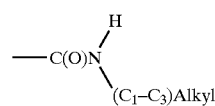

or $-C(O)N((C_1-C_3)alkyl)_2$, then $R^7$ is phenyl, phenyl substituted with 1–3 substituents [wherein the substituents independently from each other are halogen (F, Cl, Br, J), $(C_1-C_4)$ alkyl, $O-(C_1-C_4)$alkyl, $CF_3$ or $OCF_3$], piperidinyl, 1-methylpiperidinyl,

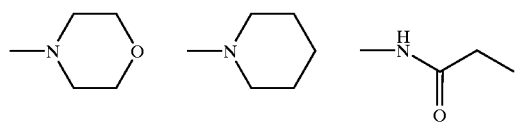

-continued

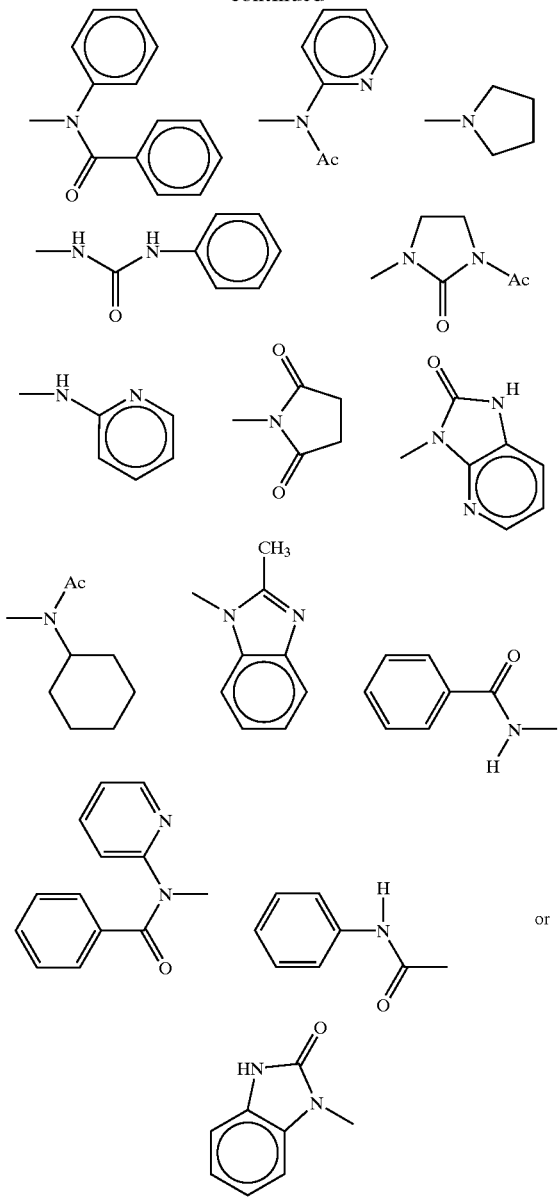

or
c) $R^7$ and $R^8$ together form the moiety

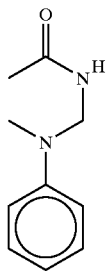

$R^3$ is H, $(C_1-C_4)$alkyl, unsubstituted or 1–3 times substituted phenyl, wherein the substituents independently of each other are halogen, $(C_1-C_4)$alkyl, O—$(C_1-C_4)$ alkyl, $CF_3$, $OCF_3$ or $NR^{17}R^{18}$ (wherein $R^{17}$ and $R^{18}$ independently of each other are H, methyl or acetyl);

$R^4$ is phenyl$(C_1-C_4)$alkyl or naphthyl$(C_1-C_4)$alkyl, wherein phenyl may be substituted with 1–3 substituents: which substituents independently of each other are halogen (F, Cl, Br, J), $(C_1-C_4)$alkyl, O—$(C_1-C_4)$ alkyl, $CF_3$, $OCF_3$ or $NR^{19}R^{20}$ (wherein $R^{19}$ and $R^{20}$ independently of each other are H, methyl or ethyl, and $R^5$ is H, $(C_1-C_4)$alkyl, $(C_3-C_6)$cycloalkyl, $CH_2COOH$, —$CH_2C(O)NH_2$, —OH or phenyl $(C_1-C_4)$alkyl.

Novel Experimental Evidence for Neuronal Sensitization in Tension-Type Headache

As discussed, precious studies in tension-type headache have in general terms indicated that there may be sensitization of muscle and nociceptive afferents and also in a non-specific way have suggested some kind of central sensitization. Whether one or the other kind of sensitization is the more important or whether indeed they both co-exist has not been clear. Recent series of experiments by the present inventors have now clearly shown that tension-type headache is indeed much more complicated than previously anticipated; thus neither the phenomenon of peripheral sensitization nor that of unspecific central sensitization does in isolation explain the condition. The studies of the present inventors have demonstrated that mechanical force due to contraction of chewing muscles may induce peripheral sensitization in chewing muscles and that this peripheral sensitization is an important factor which may or may not induce headache (Jensen and Olesen 1996). Whether this happens depends on the response of the central nervous system. Further experiments have shown for the first time that a qualitatively altered pain perception related to sensitization of second order nociceptive neurons is chronically present in subjects with tension-type headache (Bendtsen et al. 1996c). This is believed to be far the most important abnormality in tension-type headache. Thirdly, recent studies by the present inventors have demonstrated that in addition to sensitization of second order nociceptive neurons, there is also a component of a more unspecific sensitization of pain pathways at higher levels of the central nervous system (Bendtsen et al. 1996b). While sensitization of second order neurons is believed to be segmental (located only in those segments of the spinal cord/trigeminal nucleus which receive afferents from myofascial tissues), the sensitization of higher centers is of a general nature and results in increased pain sensitivity all over the body. It is anticipated that the sensitization of supraspinal neurons is a consequence of the considerably increased nociceptive input to these neurons (Lamour et al. 1983) because of the sensitization at the level of the spinal dorsal horn/trigeminal nucleus. Thus, the generalized pain hypersensitivity reflects the sensitization of second order neurons. Moreover, a recent study (Ashina et al. 1998a, Example 4 herein) by the inventors has demonstrated that the nitric oxide synthase (NOS) inhibitor, L-$N^G$ methyl arginine hydrochloride (L-NMMA), is effective in the treatment of patients with chronic tension-type headache. Since NOS inhibitors reduce spinal dorsal horn sensitization induced by continues painful input from the periphery (Mao et al. 1997) this study provides additional evidence for central sensitization at the level of the spinal dorsal horn/trigeminal nucleus in patients with tension-type headache. Another recent study (Example 8 herein) by the inventors has demonstrated that L-NMMA reduces muscle hardness in patients with tension-type headache. Increased muscle hardness is anticipated to reflect central sensitization, since it is known that central sensitization may increase the drive to motor neurons both at the supraspinal and at the segmental level (Woolf 1983), resulting in increased muscle activity and thereby in increased muscle hardness. This study, therefore, also points towards central sensitization in tension-type headache. Finally, the present inventors have recently demonstrated that experimental tooth clenching induces increased tenderness of masticatory muscles in patients with tension-type headache and that the increased tenderness precedes the induced headache by several hours (Jensen and Olesen 1996), and that the central nervous system is sensitized only in patients with tender pericranial muscles and not in patients without tender pericranial muscles (Jensen et al. 1998). Together, these studies demonstrate that the central nervous system is sensitized at the level of the spinal dorsal horn/trigeminal nucleus in patients with tension-type headache because of prolonged nociceptive input from myofascial tissues. On the basis of the combined findings of the inventors, a novel and rather complex model of the mechanisms of tension-type headache has been developed, as depicted in FIG. 1. In the following the model is described in details and its significant implications for devising successful future drug treatment of tension-type headache are discussed.

The model is illustrated in FIG. 1, in which the abbreviations have the following meaning:

| | |
|---|---|
| V: | Trigeminal nerve, |
| C2, C3: | Second and third cervical segment of the spinal cord, |
| PAG: | Periaquadactal grey, |
| DRN: | Dorsal raphe nuclei, |
| on-cells: | cells in ventromedial medulla, which activate pain pathways, for instance by reducing the threshold in the tail flick test. |
| C, Ad, Ab: | Fibers of the C, Ad, and Ab type |

Model for the Development of Tension-Type Headache Involving Neuronal Sensitization The main circuitry in FIG. 1 is the following:

Voluntary muscle activity is initiated by the supplementary motor area. This activates the motor cortex which again activates the motor nucleus of the trigeminal nerve and anterior horn cells of the C2 and C3 segments of the spinal cord causing contraction of chewing and neck muscles. Simultaneously with the activation of motor cortex, the supplementary motor area also activates the antinociceptive system. Therefore normal muscle activity, even when vigorous, is not normally perceived as painful. Another way of activating the motor pathways is via the limbic system which is concerned with emotions. When this system is activated, as in states of anxiety and stress, it is envisaged that the motor cortex and the pain facilitator system are activated simultaneously. Thus, emotionally induced involuntary muscle contraction usually induces myofascial tenderness and pain. Both voluntary and emotionally triggered muscle contraction via mechanical stress and perhaps neurogenic inflammation increase afferent input from myofascial tissues via C-fibers, A-d-fibers and A-b-fibers. C-fiber input is responsible for slow pain and, when prolonged, causes the so-called wind-up phenomenon in second order neurons located in the nucleus of the trigeminal tract and in segments C2 and C3 of the dorsal horn of the spinal cord. Wind-up is associated with increased sensitivity of second order neurons and an increase of their receptive fields. Furthermore, input via A-b-fibers becomes painful which is called allodynia. Input from the periphery in a state of wind-up causes a more intense pain than normally. With repeated or chronic micro traumatic or inflammatory reactions in myofascial tissues peripheral nociceptores, primarily projecting via C-fibers, become sensitized. Substances involved in peripheral sensitization include the potassium ion, bradykinin, histamine, ATP, neurotrophins and possibly other growth factors (Meyer et al. 1994).

Synaptic Mechanisms in the Spinal Dorsal Horn/Trigeminal Nucleus Involved in Central Sensitization How does repetitive C-fiber input to the spinal dorsal horn result in abnormal responses to normal Ab-fiber inputs, i.e. in central sensitization? The most likely answer is that C-fiber released neurotransmitters increase the excitability of dorsal horn neurons, so that previously ineffective Ab-fiber inputs to nociceptive dorsal horn neurons become effective (Woolf and. Thompson 1991). Several neurotransmitters are known to be involved in nociceptive transmission from C-fiber afferents to second order neurons in the spinal dorsal horn. These neurotransmitters can largely be divided into gases, into peptides, which are chains of amino acids, or into excitatory or inhibitory amino acids. Which are chemically single amino acids and into excitatory or inhibitory amines.

Gases

The freely diffusible gas nitric oxide (NO) is probably released from C-fibers and acts after binding to the enzyme guanylate cyclase in postsynaptic neurons. However, even though NO is considered of major importance in central sensitization, its exact role as a neurotransmitter is not yet clarified (Meller and Gebhart 1993).

Neurokinins

Neurokinins are a family of related peptides, including substance P, neurokinin A, neurokinin B and bradykinin which are known to be released from C-fibers. Currently there are three known subclasses of receptors for these peptides: neurokinin-1, (NK1) $NK_2$ and $NK_3$ receptors.

PACAP

PACAP is expressed in abundant amounts in dorsal horn neurons and is believed to play a significant role in pain transmission or the modulation of pain transmission.

Calcitonin Genie-Related Peptide (CGRP)

The exact role of this peptide in pain transmission is not known because of lack of selective receptor antagonists. However, CGRP probably protracts the breakdown of substance P in the synaptic cleft, thereby adding to the level of excitability of the spinal cord (Dickenson 1996).

Other Peptides

Several other peptides such as somatostatin, neuropeptide Y and galanin ray be important, but their exact role in central sensitization is not yet known.

Excitatory Amino Acids

It now appears that the excitatory amino acid glutamate plays a dominant role in the development of central sensitization. Glutamate is used by most neurons in the brain and spinal cord as their major excitatory transmitter. The actions of glutamate are mediated by 4 different receptor classes: the N-methyl-D-aspartate (NMDA), the a-amino-3-hydroxy-5- methyl-4-isoxazolyl-propionic acid (AMPA), the kainate receptors, and the metabotropic receptors. Of these receptors, especially the NMDA receptors are considered to be of crucial importance in central sensitization (Coderre et al. 1993).

Adenosine

The central terminals of primary afferent fibers do express adenosine receptors (Levine and Taiwo 1994). Via these receptors, adenosine can inhibit voltage-gated calcium channels via activation of a G-protein resulting in an inhibition of transmitter release from the primary afferent neuron (Rang et al. 1994). Adenosine agonists may also act to inhibit the firing of wide-dynamic neurons, probably through an increase in potassium conductance. Furthermore, adenosine has been reported to block the release of glutamate (Yaksh and Malmberg 1994). In support of these findings intrathecal adenosine has been shown to increase the nociceptive threshold (Yaksh and Malmberg 1994). Adenosine does also play a role in the peripheral tissues. In the primary afferent nociceptor adenosine acting at the $A_1$-receptor inhibit hyperalgesia, while adenosine acting at the $A_2$-receptor produces hyperalgesia via elevation of intracellular cAMP Levine and Taiwo 1994).

Gamma Amino Butyric Acid (GABA)

GABA is an important inhibitory transmitter in the central nervous system, and it has been suggested that the encoding of low-threshold mechanical stimuli as innocuous depends completely upon the presence of a tonic activation of intrinsic glycine and/or GABAergic neurons (Yaksh and Malmberg 1994). Furthermore, it has been demonstrated that the administration of GABA antagonists can produce allodynia (Woolf 1994). $GABA_B$ agonists may act to inhibit the firing of wide-dynamic neurons, probably through an increase in potassium conductance (Yaksh and Malmberg 1994) and GABA may also reduce the amount of transmitter release from the central terminals of primary afferent fibers by opening of chloride channels (Rang et al. 1994).

5-hydroxytryptamine (5-HT)

5-HT is a very important transmitter in the modulation of pain. While 5-HT has both analgesic and algesic properties, it acts mainly as an inhibitory pain transmitter in the central nervous system (Roberts 1992). Thus, when 5-HT is applied directly to the spinal cord, it produces analgesia (Fields and Basbaum 1994). The antinociceptive effects of 5-HT are mediated via many different 5-HT receptor subtypes. Thus, it is known that both the $5-HT_1$ and $5-HT_2$ and $5-HT_3$ receptors are involved in antinociception (Fields and Basbaum 1994).

Norepinephrine (NE)

Like 5-HT, also norepinephrine (NE) plays an important role as an endogenous antinociceptive transmitter. In general, noradrenergic controls are mediated at the spinal level by the action at the a-2-adrenergic receptor (Fields and Basbaum 1994). The a-2-agonist clonidine has been shown to block the release of transmitters and peptides in primary afferent terminals by presynaptic action, and it is most likely that the analgesic effects of the tricyclic antidepressants partly depend on their inhibition of norepinephrine re-uptake (Boivie 1994).

Intracellular Mechanisms in the Spinal Dorsal Horn/Trigeminal Nucleus Involved in Central Sensitization Why are the NMDA receptors considered so important? The actions of many receptors on neuronal excitability are via opening or closing of ion channels. The ion channel for the NMDA receptors allows vast amounts of calcium into the neuron, so much that the resultant increase in excitability exceeds that produced by all other receptors (Dickenson 1996). The increase in intracellular calcium initiates a cascade of biochemical events. Thus, calcium activates a calmodulin-sensitive site on NO synthase, which results in the production of NO. NO may thereafter act via at least three different mechanisms: 1) it may act in the neuron where it is produced, e.g. by increasing cyclic guanylate mono phosophate (cGMP) levels which again will activate protein kinases or by inducing the expression of immediate early genes. The protein kinases and the protein products of immediate early genes may then act as third messengers and control the expression of other genes involved in the synthesis of growth factors, channel proteins, peptides and enzymes; 2) it may act as a retrograde transmitter by diffusion to the presynaptic neuron where it modulates excitability and enhances synaptic connections; and 3) it may diffuse to adjacent neurons, e.g. interneurons (Meller and Gebhart 1993). Another important result of increased intracellular calcium is the activation of phospholipase $A_2$, leading to increases in intracellular arachidonic acid and the subsequent formation of cyclooxygenase and lipooxygenase products. Prostaglandins have been shown to increase calcium conductance on dorsal root ganglion cells and to increase the secretion of primary afferent peptides such as substance P (Yaksh and Malmberg 1994). Activation of the NMDA receptors thus has dramatic consequences and the receptors are therefore usually blocked, such that they do not participate in normal transmission. This channel block, which is mediated by physiological levels of $Mg^{2-}$ ions, can only be removed by sufficient repeated depolarization of the membrane. It is suspected that the neurokinins co-released with glutamate from C-fibers contribute to the removal of $Mg^{2+}$ ions. This important action of the neurokinins is probably mediated via $NK_1$ and $NK_2$ receptors (Dickenson 1996). Also the protein kinases activated by NO will feed back on the NMDA receptors, causing phosphorylation and partial removal of the $Mg^{2+}$ channel blockade (Woolf 1996). Other glutamate receptors are probably also involved in central sensitization, but the exact mechanisms are not yet known.

Altered Pain Perception After Central Sensitization

The increased excitability of neurons in the spinal dorsal horn/trigeminal nucleus has dramatic consequences for the pain perception in the individual patient. In the sensitized state, pain can be generated by low-threshold Ab-fibers (allodynia) (Torebjörk, et al. 1992), the response to activation of high-threshold afferents is exaggerated (hyperalgesia) (Woolf 1994), and since the receptive field of the dorsal horn neuron is increased, the central sensitization will also be manifest as a spread of hypersensitivity to uninjured sites (secondary hyperalgesia) (Torebjörk et al. 1992).

Central Sensitization in the Brain

When noxious input is received in the nucleus of the trigeminal tract, its further transmission to the thalamus and sensory cortex depends on the intensity of the input and on the balance between pain inhibiting and pain facilitating descending systems originating from the brain stem. When the pain inhibiting system is activated, it decreases the likelihood that incoming stimuli are being transmitted to the thalamus and, alternatively, when the facilitatory system is activated, it increases the likelihood of this event. From the thalamus, nociception is projected further to the sensory cortex. Via unknown mechanisms pain causes a reflex increase in muscle tone. It is envisaged that this response to pain is mediated via the limbic system because pain and anxiety are closely interrelated. There is also a cross-talk between nociception and motor activity at the level of the trigeminal nucleus/spinal cord. Finally, pain activates the sympathetic system causing release of noradrenaline. This again is responsible for an increased pain sensation, so-called sympathetically aggravated or maintained pain.

Detailed Model for the Progression of Tension-Type Headache

The progression of episodic tension-type headache into chronic tension-type headache often takes several years and happens only in a minority of episodic tension-tape headache sufferers. A genetic disposition (Østergaard et al. 1996) as well as several environmental factors seem to be involved in the development of chronicity. Despite the fact that the progression is continuous, it is best illustrated by a number of scenarios.

Scenario 1: Mild and moderate muscle contraction in normals. Voluntary muscle contraction in relation to normal functions such as chewing or head holding is initiated from the supplementary motor cortex. This is probably associated with only a minor increase in nociception from myofascial tissues and no wind-up in non-headache sufferers. Simultaneously the antinociceptive system is activated such that no sensation of pain occurs.

Scenario 2: Forceful and/or long-lasting muscle activity, in normals. With particularly vigorous muscle activity and especially when it is very protracted, the strain on myofascial tissues may be such that nociception is rather marked and tenderness and local pain may occur, but it is rapidly controlled by local reparative mechanisms in myofascial tissues and a continuously active antinociceptive system. Tenderness without spontaneous pain on the day after exercise may be a result of this balance or may be a purely local phenomenon.

Scenario 3: Involuntary muscle activity induced by the limbic system in normals. In contrast to activation initiated by the supplementary motor area, muscle contraction initiated by the limbic system is not associated with an increased antinociceptive activity. On the contrary it is proposed to be associated with increased activity in the pain facilitatory system. An alternative is a decrease in the activity of the antinociceptive system, but this is unlikely because this system is normally not tonically active. Limbic initiated muscle activity therefore causes pain even with moderate degrees of contraction and also with relatively short-lasting contractions. However, in normals the drive from the limbic system is short lasting and so are the mild changes in myofascial tissues induced by the motor activity. The headache is therefore self limiting.

Scenario 4: Voluntary contraction in patients with severe episodic—and chronic but not daily tension-type headache. In most of these individuals voluntary muscle activity will be painful. In part this is due to permanent sensitization of second order neurons in the nucleus of the trigeminal tract, in part it is due to the fact (Jensen and Olesen 1996) that the antinociceptive system is not activated as normally. Contraction therefore aggravates tenderness and causes pain from the myofascial structures (Jensen and Olesen 1996) The process of reverting the system back to normal may be more or less effective. This variable duration of the initiating stimulus accounts for the variable duration of the headache.

Scenario 5: Severe (daily) chronic tension-type headache.

In severe chronic tension-type headache there is a state of chronic sensitization in myofascial tissues and in central pain pathways both at the second order neurons and at higher centers. There is a minor constant elevation of EMG signal from cranial muscles. In addition, the most severe cases also have a more diffuse sensitization revealed in decreased pain thresholds throughout the body (Bendtsen et al. 1996b). Chronically increased muscle activity maintains a state of chronic peripheral sensitization which again maintains a state of chronic sensitization in the second order neurons in the nucleus of the trigeminal tract (Bendtsen et al. 1996c). This causes steady inflow of nociceptive signals to the thalamus and the perception of chronic pain by the sensory cortex. This again activates the limbic system and stimulates tonic involuntary muscle activity. In this situation of chronic pain there is probably also activation of the sympathetic nervous system adding a component of sympathetically mediated pain to the whole picture. On top of this chronic situation of sustained pain, it is easy to see how additional strain would result in increased and prolonged pain. A further increase in muscle activity would for instance in the sensitized peripheral myofascial tissues lead to a stronger than normal nociceptive input to the already sensitized nucleus of the trigeminal tract which would project to already sensitized hemispheric pain centers. A vicious circle has been set up and it may become permanent due to changes in gene transcription and consequent structural changes in neurons aid synapses.

Rationale for the Novel Strategy According to the Invention for the Treatment of Tension-Type Headache Previous treatments have primarily been directed towards reducing muscle contraction i.e. biofeedback treatment, physiotherapy, dental treatment, exercises and muscle relaxants. All of these treatments have had limited or no success. It follows from the model according to the present inventors that therapeutic intervention should be directed primarily towards the afferent system and above all against sensitization of second order neurons in the nucleus of the trigeminal tract and upper cervical segments. Furthermore, it follows that while intervention using peripherally acting analgesics or other measures which reduce peripheral nociceptive input is sufficient in episodic tension-type headache, this is not so for severe episodic and chronic tension-type headache, where sensitization of second order neurons occurs. In these patients, desensitization of these neurons should be the major target for drug intervention. It may, however, be difficult to desensitize these neurons in face of an ongoing vigorous input from the periphery. Therefore, drugs which reduce peripheral sensitization may be needed in addition to the drugs which desensitize second order nociceptive neurons, or drugs working at both levels may be needed. Preferably, treatment should be given early enough to prevent sensitization of second order neurons. Alternatively, if marked sensitization at the cortical level occurs, the individual being hypersensitive to painful stimuli all over the body, it may not be enough to intervene against the sensitization of second order neurons. For such patients intervention against cortical sensitization is recommended as an additional measure.

The Novel Therapeutic Principle According to the Invention for Treatment of Tension-Type Headache According to the present invention, several means of intervening against tension-type headache can be envisaged, depending on the level according to the above, at which the intervention is aimed. In either case, be it in the periphery, the second order neurons of the sensory trigeminal nucleus or the cortex, the intervention must target the transmission of nerve impulses. A number of different transmitter substances are involved in this transmission at each level. Thus, the invention, in some of its aspects, relate to the following therapeutic principles in tension-type headache of the chronic type and of the severe episodic type defined as having headaches ten or more days per month:

- Administration of agents or drugs (in the present specification and claims, the terms agent and drug are used as interchangeable) which prevent or reduce sensitization of second order nociceptive neurons located in the nucleus of the descending tract of the trigeminal nerve and in the C2 and C3 segments of the dorsal cervical horn of the spinal cord. There are several known types of assays indicating the capability of an agent to prevent or reduce central sensitization. In the following, 13 such assays are described.

- Administration of agents or drugs which reduce supraspinal pain sensitization to a normal level. These are agents or drugs which normalize the response of pressure pain thresholds in the temporal region to tooth clenching and drugs which normalize pain thresholds in hand.

- Administration of agents or drugs which reduce peripheral sensitization defined as agents or drugs which prevent the development of abnormal tenderness due to tooth clenching.

- Administration of agents or drugs which normalize the pain response to intra muscular infusion of bradykinin, 5-HT, histamine, prostaglandines and/or nitroglycerine.

- Administration of agents or drugs which normalize local pressure pain threshold over myofascial tissues of the head.

- Administration of agents or drugs which have more than one of the above effects.

- Administration of agents or drugs which in a panel of test patients with tension-type headache have one of the above effects described one by one.

When targeting the transmission of nerve impulses according to the invented model, it is preferred to interact with the following substances relating to neurotransmission in connection with pain:

Glutamate
Substance P
Nitric oxide
GABA

It is particularly preferred to:
Antagonize the effect of glutamic acid
Antagonize the effect of substance P
Antagonize the effect of nitric oxide
Stimulate the effect of GABA.

More specifically, it is preferred to use:
NMDA receptor antagonists
Inhibitors of neuronal nitric oxide synthase (NOS)
GABA A and GABA B receptor agonists Counteraction of Central Sensitization of Second Order Neurons In order to counteract central sensitization of second order neurons of the sensory trigeminal nucleus/dorsal horn, it will be advantageous to cause a decrease in neuronal transmission involving the pathways utilizing e.g. the transmitter substances glutamate, nitric oxide, and the neurokinins (substance P, bradykinin, neurokinin A, neurokinin B). Also, it will be of interest to counteract the action of second messengers such as guanylate cyclase, cGMP as well as any further steps in the action of cGMP in second order sensory neurons receiving nociceptive input from the head and neck.

Prevention of Central Sensitization of Second Order Neurons

In order to prevent the occurrence of central sensitization of second order neurons of the sensory trigeminal nucleus/dorsal horn, it will be advantageous to normalize neuronal transmission in the peripheral and/or central nervous system involving transmitter substances such as glutamate, GABA, adenosine, nitric oxide, the neurokinins (substance P, bradykinin, neurokinin A, neurokinin B), neurotrophins and histamine. While it might have seemed advantageous to use 5-HT$_{1D}$ receptor agonists because they stabilize presynaptic nociceptive terminals, studies by the inventors have shown that a compound of this class (sumatriptan) is not effective to a clinically relevant extent in tension-type headache although it is highly effective in migraine (Brennum et al. 1992, 1996). Counteracting excitatory 5-HT receptors, such as 5-HT$_2$ and 5-HT$_3$ localized on second order neurons, however, are contemplated to be effective in the treatment of tension-type headache in accordance with the present invention.

DETAILED DESCRIPTION OF THE INVENTION

On the basis of their experimental discoveries and analyses, the present inventors have devised, for the first time, a strategy for the treatment or prevention of tension type headache. Up to now, there has not been any effective treatment available for tension type headache, which has been a very serious problem in view of the very high prevalence of tension-type headache.

The present invention relates to a method of treatment or prevention of tension-type headache in a person in need of such treatment, the method comprising administering an amount of an agent effective to interact with neuronal transmission connected with pain perception so as to prevent or reduce central sensitization.

The attainment of prevention or reduction of central sensitization can be demonstrated by one of the following assays:

1) Normalization of a pathological qualitatively altered stimulus-response function. The attainment of a normalization of a qualitatively altered stimulus-response function in connection with nociception (Bendtsen et al. 1996c, Example 1) can be demonstrated by palpation of the trapezius muscle and recording of the degree of pain corresponding to the intensity of palpation (Bendtsen et al. 1994). When a curve representing the stimulus/response function in connection with nociception has changed in shape from being substantially linear in a normal representation to being substantially linear in a double logarithmic representation, a normalization of the qualitatively altered stimulus/response function has been obtained. In the present context, an agent which normalizes a qualitatively altered stimulus-response function in connection with nociception is an agent which, when administered to a group of at least 20 patients suffering from tension-type headache, will cause the curve representing the stimulus/response function in connection with nociception to become substantially linear when represented double logarithmically in at least 10 of the patients. Preferably, the agent so defined has such an effect in at least 12 of the patients. More preferably, the agent so defined has such an effect in at least 14 of the patients.

2) Normalization of a pathological abnormally low pain threshold. The attainment of a normalization of an abnormally low pain threshold can be demonstrated by the measurement of the pressure pain threshold in the extremities or in the pericranial region with an electronic pressure algometer or by the measurement of the electrical pain threshold with a constant current stimulator as previously described (Bendtsen et al. 1996a). When the pain threshold has changed from being significantly lower in a group of patients with tension-type headache than in a group of healthy controls to be not significantly different between the two groups, a normalization of the abnormally low pain threshold has been obtained. In the present context an agent which normalizes an abnormally low pain threshold is an agent which, when administered to a group of at least 10 patients suffering from tension-type headache, will change the pain threshold from being significantly lower than that in a group of healthy controls to be not significantly different between the two groups.

3) Reduction of a pathological pericranial muscle hardness. The attainment of reduction of pericranial muscle hardness can be demonstrated by the measurement of hardness in the pericranial muscles with a hardness meter as previously described (Ashina et al. 1998a), when the muscle hardness is reduced significantly more following the administration of a given agent than following the administration of placebo, a reduction of muscle hardness has been obtained. In the present context, an agent which reduces pericranial muscle hardness is an agent which, when administered to a group of at least 10 patients suffering from tension-type headache, will reduce pericranial muscle hardness significantly more than placebo. Such a reduction will typically be at least 10%. Preferably the reduction will be at least 20%. More preferably the reduction will be at least 30%.

4) Reduction of a pathological increased pericranial myofascial tenderness. The attainment of reduction of increased pericranial myofascial tenderness can be demonstrated by the measurement of the tenderness in the pericranial region using the Total Tenderness Scoring system as previously described (Bendtsen et al. 1995). Myofascial tenderness is considered to be increased when the Total Tenderness Score or the Local Tenderness Score in the pericranial region is above the 75% percentile of the Total Tenderness Score or the Local Tenderness Score in a group of healthy controls (Jensen and Rasmussen 1996). In the present context, an agent which reduces increased pericranial myofascial tenderness is an agent which, when administered to a group of at least 10 patients suffering from tension-type headache, will reduce the Total Tenderness Score or the Local Tenderness Score in the pericranial region by at least 10% compared with the administration of placebo. Preferably, the agent so defined will reduce the Total Tenderness Score or the Local Tenderness Score in the pericranial region by at least 20% compared with the administration of placebo. More preferably, the agent so defined will reduce the Total Tenderness Score or the Local Tenderness Score in the pericranial region by at least 30% compared with the administration of placebo.

5) Prevention or reduction of pain, tenderness or hardness in pericranial muscles, or prevention or normalization of a qualitatively altered stimulus-response function or a reduced pain threshold induced by experimental tonic muscle contraction. The attainment of prevention or reduction of pain, tenderness or hardness, or prevention or normalization of a qualitatively altered stimulus-response function or a reduced pain threshold can be demonstrated as described in assays 1–4 above. Experimental tonic muscle contraction can be obtained by clenching of the molar teeth for 30 minutes at 10% of the individual subject's maximal voluntary contraction measured from electromyographic recordings of the activity in the temporal or masseter muscles as previously described (Jensen and Olesen 1996). In the present context, an agent which prevents or reduces pain, tenderness or hardness, or prevents or normalizes a qualitatively altered stimulus-response function or a reduced pain threshold induced by experimental tonic muscle contraction is an agent which, when administered to a group of at least 10 human subjects, will prevent or reduce pain, tenderness or hardness, or prevent or normalize a qualitatively altered stimulus-response function or a reduced pain threshold induced by experimental tonic muscle contraction to a significantly higher degree than placebo.

6) Prevention or reduction of pain, tenderness or hardness in pericranial muscle, or prevention or normalization of a qualitatively altered stimulus-response junction or a reduced pain threshold induced by intra muscular infusion of algogenic substances. The attainment of prevention or reduction of pain, tenderness or hardness, or prevention or normalization of a qualitatively altered stimulus-response function or a reduced pain threshold can be demonstrated as described in assays 1–4 above. Intra muscular infusion of algogenic substances can be performed by the use of a 0.4 mm needle as previously described (Jensen et al. 1990). Algogenic substances such as bradykinin, serotonin, histamine, adenosine-triphosphate, prostaglandines, capsaicin, hypertonic saline, potassium, nitroglycerine or combinations hereof can be used. The algogenic substances can be injected either as a single bolus injection (Jensen et al. 1990) or as a prolonged infusion (Zhang et al. 1993). In the present context, an agent which prevents or reduces pain, tenderness or hardness, or prevents or normalizes a qualitatively altered stimulus-response function or a reduced pain threshold induced by intra muscular infusion of algogenic substances is an agent which, when administered to a group of at least 10 human subjects, will prevent or reduce pain, tenderness or hardness, or prevent or normalize a qualitatively altered stimulus-response function or a reduced pain threshold induced by intra muscular infusion of algogenic substances to a significantly higher degree than placebo.

7) Prevention or reduction of pain, tenderness or hardness in pericranial muscle, or prevention or normalization of a qualitatively altered stimulus-response function or a reduced pain threshold induced by stimulation of nociceptive afferents in myofascial tissues. The attainment of prevention or reduction of pain, tenderness or hardness, or prevention or normalization of a qualitatively altered stimulus-response function or a reduced pain threshold can be demonstrated as described in assays 1–4 above. Stimulation of nociceptive afferents in myofascial tissues can be obtained by methods such as eccentric muscle contraction (Howell et al. 1993), prolonged static muscle contraction, repeated monotonous muscle work, ischemic muscle exercise (Myers and McCall Jr 1983), electrical stimulation via needle electrodes inserted into the muscles (Vecchiet et al. 1988) or mechanical pressure applied to the muscles. In the present context, a substance which prevents or reduces pain, tenderness or hardness, or prevents or normalizes a qualitatively altered stimulus-response function or a reduced pain threshold induced by stimulation of nociceptive afferents in myofascial tissues is a substance which, when administered to a group of at least 10 human subjects, will prevent or reduce pain, tenderness or hardness, or prevent or normalize a qualitatively altered stimulus-response function or a reduced pain threshold induced by stimulation of nociceptive afferents in myofascial tissues to a significantly higher degree than placebo.

8) Prevention or reduction of secondary allodynia or secondary hyperalgesia induced by stimulation of nociceptive afferents in myofascial tissues. The attainment of prevention or reduction of secondary allodynia or secondary hyperalgesia can be demonstrated by measuring pain sensitivity in the unaffected tissue area that surrounds an area in which nociceptive afferents are stimulated (Magerl et al. 1998). Pain sensitivity can be measured by visual analogue scale recording of the pain intensity evoked by stimuli such as mechanical pressures applied by an electronic pressure algometer, manual palpation or pressure-controlled palpation (Bendtsen et al. 1995; Bendtsen et al. 1996a), punctuate mechanical stimuli applied by von Frey hairs (Magerl et al. 1998), light touch stimuli applied by a soft cotton wisp (Magerl et al. 1998), thermal stimuli applied by the Marstock thermotest (Nørregaard et al. 1997) or electrical stimuli applied by surface electrodes (Bendtsen et al. 1996a) or intra muscular needle electrodes (Vecchiet et al. 1988) or by measuring the nociceptive flexion reflex (Willer et al. 1984). Stimulation of nociceptive afferents in myofascial tissues can be obtained as described in assays 5–7 above. In the present context, an agent which prevents or reduces secondary allodynia or secondary hyperalgesia induced by stimulation of nociceptive afferents in myofascial tissues is an agent which, when administered to a group of at least 10 human subjects, will prevent or reduce secondary allodynia or secondary hyperalgesia induced by stimulation of nociceptive afferents in myofascial tissues to a significantly higher degree than placebo.

9) Prevention or reduction of wind-up induced by repetitive stimulation of nociceptive afferents in the pericranial region. The attainment of prevention or reduction of wind-up can be demonstrated by measuring pain sensitivity to repeated stimuli (Magerl et al. 1998), since temporal summation of painful stimuli is regarded as a psychophysical correlate of wind-up (Price et al. 1994). In the present context, wind-up is defined to be present when repeated identical stimuli become increasingly painful (Pedersen et al. 1998). Wind-up can be induced by stimuli such as repeated electrical stimuli, e.g. five stimuli of 1 ms duration with an intensity of 1.4 times the baseline pain threshold delivered at 2 Hz by a constant current stimulator (Pedersen et al. 1998), or as repeated punctuate mechanical stimuli, e.g. five stimuli delivered at 2 Hz with a 256 mN calibrated von Frey hair (Magerl et al. 1998). The evoked pain intensity can be measured using a visual analogue scale. In the present context, an agent which prevents or reduces wind-up induced by stimulation of nociceptive afferents in the pericranial region is an agent which, when administered to a group of at least 10 human subjects, will prevent or reduce wind-up induced by stimulation of nociceptive afferents in the pericranial region to a significantly higher degree than placebo.

10) Prevention or reduction of secondary allodynia or secondary hyperalgesia induced by nociceptive input in an experimental animal model. The degree of secondary allodynia or secondary hyperalgesia can be examined by measuring pain sensitivity in the unaffected tissue area that surrounds an area in which nociceptive afferents are stimulated (Magerl et al. 1998). Pain sensitivity can be measured by recording the response of the animal to well-defined stimuli, e.g. briskly stroking the skin with the blunt point of a pencil (Magerl et al. 1998), mechanical pressures applied by an electronic pressure algometer, manual palpation, pressure-controlled palpation or calibrated von Freys hairs (Hao et al. 1992), electrical stimuli or thermal stimuli (Hao et al. 1992). The response of the animal can be measured by methods such as: a) grading of the behavior of the animal to avoid a given stimulus, e.g. as a score of 0: no response; 1: moderate efforts to avoid the stimulus; and 2: vigorous efforts to escape the stimulus (Hao et al. 1992); b) recording the time required for eliciting a given response of the animal, e.g. withdrawal of an extremity, by a given stimulus (Hao et al. 1992); c) recording the intensity of a stimulus that elicits a given reaction, e.g. vocalization or withdrawal or licking of an extremity (Hao et al. 1992); or d) by a combination of the above-mentioned methods (Hao et al. 1992). The induction of secondary allodynia or secondary hyperalgesia can be performed as described above in assays 6 and 7 or by methods such as the application to the skin of chemical irritants, e.g. mustard oil (Woolf and King 1990), thermal stimuli (Hylden et al. 1989), pinching, subcutaneous or intra muscular injections of complete Freund's adjuvant (Hylden et al. 1989). In the present context, an agent which prevents or reduces secondary allodynia or secondary hyperalgesia induced by nociceptive input in an experimental animal model is an agent which will prevent or reduce secondary allodynia or secondary hyperalgesia induced by nociceptive input in an experimental animal model to a significantly higher degree than placebo.

11) Prevention or reduction of wind-up induced by repetitive stimulation of nociceptive afferents in as experimental animal model. The degree of wind-up can be examined by measuring pain sensitivity (Magerl et al. 1998) or the activity of second order neurons to repeated stimuli (Woolf and Thompson 1991). In the present context, wind-up is defined to be present when repeated identical stimuli become increasingly painful (Pedersen et al. 1998) or potentiate the responses of second order neurons (Laird et al. 1995). Pain sensitivity in animals can be recorded as described above in assay 10, while the activity of second order neurons can be measured using extra- and intracellular recordings of the activity in these neurons (Woolf and King 1990; Hu et al. 1992). After exposure of the spinal cord via laminectomy, extracellular recordings can be made using glass microelectrodes and intracellular recordings can be made using potassium acetate electrodes (Woolf and King 1990). Wind-up can be induced by stimuli such as those described in assay 10. In the present context, an agent which prevents or reduces wind-up induced by repetitive stimulation of nociceptive afferents in an experimental animal model is an agent which will prevent or reduce wind-up induced by repetitive stimulation of nociceptive afferents in an experimental animal model to a significantly higher degree than placebo.

12) Prevention or reduction of increased receptive field size of second order neurons induced by nociceptive input in an experimental animal model. The receptive field size of second order neurons can be measured using extra- and intracellular recordings of the activity in these neurons (Woolf and King 1990; Hu et al. 1992) as described above in assay 11. The receptive fields can be mapped using stimulation with e.g., calibrated von Frey hairs, blunt probes (Hylden et al. 1989), thermal stimuli (Hylden et al. 1989), serrated forceps or calibrated pinchers applied to the skin (Woolf and King 1990). The induction of increased receptive field size of second order neurons can be performed as described above in assay 10. In the present context, an agent which prevents or reduces increased receptive field size of second order neurons induced by nociceptive input in an experimental animal model is an agent which will prevent or reduce increased receptive field size of second order neurons induced by nociceptive input in an experimental animal model to a significantly higher degree than placebo.

13) Prevention or reduction of increased excitability of the flexion reflex induced by nociceptive input in an experimental animal model. The excitability of the flexion reflex can be examined by measuring the activity in flexor motor neurons elicited by a standard stimulus applied ipsilaterally to the recording of flexor motor neuron activity (Woolf 1983). The examination can, e.g., be performed by extracellular recordings of the activity from flexor alpha motor neurons to the posterior biceps femoris/semitendinosus muscles in the decerebrate rat (Woolf and Thompson 1991). The flexion reflex can, e.g. be elicited by a standard pinch applied to the ipsilateral toes (Woolf and Thompson 1991). The induction of increased excitability of the flexion reflex can be performed as described above in assay 10. In the present context, an agent which prevents or reduces increased excitability of the flexion reflex induced by nociceptive input in an experimental animal model is an agent which will prevent or reduce increased excitability of the flexion reflex induced by nociceptive input in an experimental animal model to a significantly higher degree than placebo.

Prevention or reduction of central sensitization induced by nociceptive input in an experimental animal model. The degree of central sensitization in an experimental animal model can be measured by other methods which are presumed to reflect central sensitization but which are not mentioned in the above described assays 10–13, i.e. measurement of cellular intermediate early genes such as c-fos (Dubner and Ruda 1992). The induction of central sensitization can be performed as described above in assay 10. In the present context, an agent which prevents or reduces central sensitization induced by nociceptive input in an experimental animal model is an agent which gill prevent or reduce central sensitization induced by nociceptive input in an experimental animal model to a significantly higher degree than placebo.

In the present context the term "significantly higher degree than placebo" should be taken to mean statistically significant when the relevant statistical tests are applied to data relating to an effect of an agent according to the invention compared to an effect of placebo in any given assay or test.

The interaction with neuronal transmission connected with pain perception will normally be interaction with neuronal transmission connected with second order nociceptive neurons. This interaction will normally involve prevention of sensitization by way of a reduction of C-fiber input to the second order nociceptive neurons or reversal of an already established sensitization of second order nociceptive neurons.

Interaction with neuronal transmission connected with pain perception can be exerted by increasing inhibitory synaptic stimuli or it can be exerted by decreasing excitatory synaptic stimuli.

By the term "palpation" is meant the act of applying, with the fingers, pressure to the surface of the body for the purpose of determining the amount of pain elicited in the underlying tissue by said pressure intensity.

In the present context, the term "qualitatively altered stimulus/response function" in connection with nociception means that the function describing the amount of pain elicited by a given pressure intensity, sensed by a person being palpated, has changed in shape from being positively accelerating to being substantially linear, of Example 1.

By the term "tender muscle" is meant a muscle in which pain is elicited by palpation with a clinically relevant pressure.

In the present context, by the term "central sensitization" is meant that second order nociceptive neurons residing in the central nervous system are rendered more sensitive than normally to incoming synaptic stimuli. At the occurrence of central sensitization such stimuli will elicit excitation of the said central neurons at stimulation below the normal threshold for excitation; thus, central neurons possess an increased excitability.

In the present context, myofascial pain relates to pain in the myofascial tissue, by which is meant muscular structures, tendons and tendon insertions related to the pericranial and cervical region.

In the context of the present invention second order nociceptive neurons are neurons located in the nucleus of the trigeminal tract and of C2 and C3 segments of medullary dorsal horns, said neurons being involved in the processing of nociceptive stimuli.

By the term "C-fibers" is meant a class unmyelinated nociceptive fibers terminating on neurons in the nucleus of the trigeminal tract/dorsal horn of the spinal cord, The interaction with neuronal transmission connected with pain perception, so as to obtain a substantial prevention or a substantial normalization of an otherwise qualitatively altered stimulus-response function in connection with nociception is preferably performed by administering an effective amount of an agent which prevents or normalizes an otherwise qualitatively altered stimulus-response function in connection with nociception.

In the present context, an agent which prevents or normalizes an otherwise qualitatively altered stimulus-response function in connection with nociception is an agent which, when administered to a group of at least 20 patients suffering from tension type headache as defined above, till cause the curve representing the stimulus/response function in connection with nociception to become substantially linear when represented double logarithmically in at least 10 of the patients. Preferably the agent so defined has such an effect in at least 12 of the patients. More preferably the agent so defined has such an effect in at least 14 of the patients.

A number of substances and classes of substances which interact with neuronal transmission to exert this function are known, confer the detailed discussion thereof in the following.

In accordance with what is explained above, another way of expressing the treatment according to the invention is by reference to pain threshold in connection with chronic contraction of muscle, in particular tooth clenching. Thus, according to this, the invention can be expressed as a method for treatment of tension-type headache in a person in need of such treatment, comprising interacting with neuronal transmission connected with pain perception so as to obtain a substantial increase of an otherwise unresponsive pain threshold in connection with chronic contraction of muscle, in particular tooth clenching.

Again, the interaction is preferably performed by administering an agent which will interact with neuronal transmission in a manner corresponding to what has been described above. The agent can be characterized as a agent which performs positively (as described above), in one or more of the assays described above, such as the stimulus/response function test described above, or as a agent which, in a group of at least 20 patients suffering from tension tape headache as defined above, will cause the effect of tooth clenching to be an increased pain threshold instead of an abnormally low pain threshold in at least 10 of the patients, preferably at least 12 of the patients, more preferably in at least 14 of the patients.

In another aspect, the invention relates to an agent having the properties defined herein for use as a medicament, in particular for the treatment of tension-type headache. This aspect relates to those substances or substance classes discussed herein which have not previously been used as medicaments or diagnostics. In a further aspect, the invention relates to the use of an agent having the properties described herein for the preparation of a pharmaceutical composition for the treatment or prevention of tension-type headache.

In one aspect of the present invention the treatment or prevention of tension-type headache according to the invention is not accompanied by a substantial reduction of muscle tension.

In an important aspect the present invention relates to a method for treating tension-type headache in a person which comprises administering an agent in an amount effective to alleviate said headache, said agent being an agent capable of altering the relationship of pain intensity to pressure intensity when the trapezoid muscle is palpated at different pressure intensities in said person. The relationship is typically substantially linear in the untreated persons, and substantially non-linear in the treated persons. Furthermore, the relationship will typically be positively accelerating in the treated person. In one embodiment of the present invention the rate of acceleration of pain intensity with pressure intensity is substantially constant. In one important embodiment of the present invention the relationship in the treated persons is substantially the same as in control persons who did not have tension-type headache and who were treated with a placebo.

The agent interacting with neuronal transmission to substantially normalize an otherwise qualitatively altered stimulus/response function in connection with nociception is preferably one which directly quantitatively lowers pain perception, in that, in a panel of test persons suffering from increased myofascial tenderness with disorder of pericranial muscle in connection with tension-type headache, the administration of the agent will result in transformation of a substantially linear pain intensity perception in response to pressure intensity in trapezius as well as other relevant pericranial muscles into a curve (C) of which the values of pain intensity are lower than the linear pain intensity perception.

The curve (C) is preferably a curve which can be described substantially as a power function and is a curve which is substantially linear in a double logarithmic plot.

It is preferred that substantially each of the values of curve (C) is at the most 20% higher, preferably at the most 10% higher, than the value of the corresponding curve produced for a test panel of healthy controls.

In connection with any of the patient panel tests discussed above it is noted that the treatment with the agent in question should be performed by administration at least once daily to maintain a therapeutic plasma level in the patients and should be continued for a sufficient time to allow the agent to exert its therapeutic effect, but that an agent is considered not to perform according to the particular test if the effect is not obtained within a treatment time of three months. This does not mean that it will necessarily take three months for an agent to exert its therapeutic effect; some compounds will show their therapeutic effect after much shorter treatment periods, down to days or even hours. In connection with testing of a new candidate agent, the dosage of the agent will normally be kept as high as permitted by the toxicity of the compound during initial tests and will then be reduced to a lower level which is still maximally effective during the test proper.

Evaluation of the ability of an agent to provide an effective treatment for tension-type headache, by interacting with neuronal transmission according to the present invention, may also be performed as an acute test, in which the agent is administered, typically as a bolus or an infusion, to a group of patients suffering from chronic tension-type headache. In such a test, the pain connected to tension-type headache in these patients will typically be scored by the patients, as described in example 4, at various time points after administration of the agent, typically at least every 15 min and subsequently monitored over a period of at least 30 min, typically at least 60 min. preferably at least 90, more preferably at least 120 min. For the evaluation of a candidate agent, an additional group of patients acutely suffering from tension-type headache will receive placebo and serve as a control group. The curves based on the pain scores of patients in both groups will typically be compared, as shown in FIG. 14, and an agent will be considered effective in treatment of tension-type headache according to the present invention, if it is capable of preventing or substantially preventing pain in connection with tension-type headache when pain scores after administration of the agent, when differing most from the corresponding score after administration of placebo, are at least 10% lower than scores for placebo, typically at least 20% lower, preferably at least 30% lower, more preferably at least 40% lower. For an evaluation as described here, the size of the participating groups of patients will be at least 5 patients in each group, typically at least 7 patients in each group, preferably at least 10 patients in each group, more preferably at least 12 patients in each group, even more preferably at least 15 patients in each group.

Evaluation of the ability of an agent to provide an effective prevention of tension-type headache by interacting with neuronal transmission according to the present invention can be performed as described above except that the parameter measured and scored by headache patients will typically be duration of pain or frequency of pain in connection with tension-type headache in sufferers with an episodic form of the disease.

In the practical treatment of a patient, the administration of an agent will normally be continued for at least one month, preferably at least two months and more preferably at least three months and in many cases indefinitely in order to establish and maintain the normalization which is aimed at. If the desired normalization occurs before one month of treatment, it is certainly possible according to the invention to discontinue the treatment, but this will increase risk of relapse and is normally not preferred. The administration is performed using at least one dose daily or at any rate substantially at least one dose daily (which means that the treatment is not outside the scope of the invention if it is just interrupted one or perhaps even (but not preferred) a few days), and the dose of the particular agent is preferably adapted so that it will maintain a therapeutic plasma level substantially at any time. Notwithstanding the above statement to the effect that the administration may in many cases be performed indefinitely, it is contemplated that there will be cases where the treatment period will be less than 10 years, such as less than 5 years or less than 2 years or even less than 1 year.

The interaction with neuronal transmission connected with pain perception will normally be such an interaction with neuronal transmission connected with second order nociceptive neurons which involves substantially reducing excitation mediated through the interaction between transmitter substances and their receptors on second order nociceptive neurons.

The above-mentioned interaction will normally involve a reduction of C-fiber, A-d-fiber and A-b-fiber input to the nociceptive second order neurons, through a substantial reduction of excitatory activity in synapses of C-fibers, A-d-fibers and A-b-fibers on second order neurons, said activity mediated through the interaction between the involved transmitter substances and their receptors on second order nociceptive neurons.

The reduction of excitatory activity in synapses of C-fibers, A-d-fibers and A-b-fibers on second order neurons mediated through the interaction between the involved excitatory transmitter substances and their receptors on second order nociceptive neurons swill preferably be performed by administration of an effective amount of at least one agent which a) substantially inhibits the production of said excitatory transmitter substance, b) substantially inhibits the release of said excitatory transmitter substance, c) substantially counteracts the action of said excitatory transmitter substance, and/or d) substantially inhibits the binding of said excitatory transmitter substance to its relevant receptors.

Important examples of such excitatory transmitter substances are selected from the group consisting of glutamate, nitric oxide, neurokinins (substance P, neurokinin A, neurokinin B and bradykinin), CGRP, adenosine working through A2 receptors, 5-HT when working through $5\text{-HT}_{2,3}$ receptors and pituitary adenylate cyclase activating polypeptide (PACAP).

Agents which can interact with neuronal transmission mediated by glutamate will typically comprise competitive or non-competitive antagonists of ionotropic glutamate receptors, including NMDA, AMPA and kainate receptors. Interaction with glutamate neurotransmission can also be performed with antagonists at the glycine site of the NMDA receptors or with antagonists or inverse agonists at modulatory sites such as polyamine sites. Interaction with metabotropic glutamate receptors can be performed with agonists or antagonists depending on whether they are receptors located pre or postsynaptically and whether they belong to the excitatory type I receptors (mGluR1,5) or the inhibitory type II and type III receptors (mGluR2,3 and mGluR4,6–8, respectively).

While sensitization of second order neurons is believed, as explained above, to be an important cause of pain in connection with tension type headache, it is clear that other elements of neuronal transmission may also play a significant role and in some cases even a predominant role as explained in the model described in connection with FIG. 1. Based on this recognition, another, more general, aspect of the present invention introduces, for the first time, the use of a number of classes of substances for treatment of tension type headache. This aspect relates to a method for treatment or prevention of tension-type headache in a person in need of such treatment, comprising administering an amount of an agent which, in the peripheral and/or central nervous system, is effective to specifically interact with neuronal transmission connected with pain perception by a) substantially antagonizing the action of glutamate, 5-HT, GABA, nitric oxide, nitric oxide synthase, guanylate cyclase, cyclic guanylate monophosphate (cGMP), CGRP, substance P, neurokinin A, neurokinin B, bradykinin, PACAB, adenosine, glycine, histamine, neurotrophins, $Na^+$ ions or $Ca^{2+}$ ion channels, or by b) substantially potentiating the action of adenosine, galanine or norepinephrine, with the proviso that said agent is not ethyl 2-amino-6-(4-fluorobenzylamino)-3-pyridylcarbamate or an arylglycineamide derivative as described herein.

An additional aspect of the present invention relates to a method of treatment of tension-type headache comprising administering to a person in need of such treatment an effective amount of an agent which substantially inhibits the action of the enzyme nitric oxide synthase (NOS) and thereby reduces chronic pain in connection with tension-type headache. In many cases the effect of treatment of tension-type headache with a NOS inhibitor will be exerted through a decrease in existing central sensitization, but also within the scope of the invention is treatment of tension-type headache with NOS inhibitors whose effect on the reduction of pain in connection with tension-type headache is mediated through a mechanism not directly involving inhibition of central sensitization. Such an alternative mechanism might possibly comprise an alteration of pain modulation involving nitric oxide.

A very important aspect of the present invention is a method of screening a drug for the ability to alleviate a tension-type headache which comprises comparing the relationship of pain intensity to pressure intensity when the trapezoid muscle is palpated at different pressure intensities for (a) persons having tension-type headaches after treatment with the drug, and (b) persons having tension-type headaches, treated with a placebo, and determining if the relationship is altered. Also within the scope of the present invention is a method of screening a drug for the ability to alleviate tension-type headache comprising testing said drug in one or more of the assays 1–13 described above and determining effect in the test organism according to each assay. The test organisms will typically be human patients and human controls or relevant experimental animals, depending on the given assay.

In the following discussion of substances or groups of substances, numbers in parenthesis refer to the correspondingly numbered structural formulas in the formula sheets below.

NMDA receptor antagonists
competitive
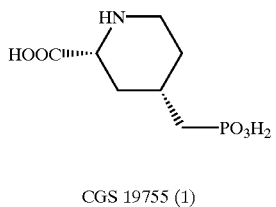
CGS 19755 (1)
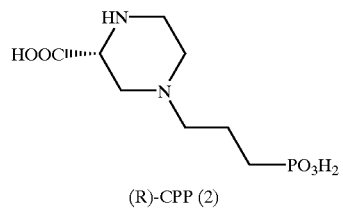
(R)-CPP (2)
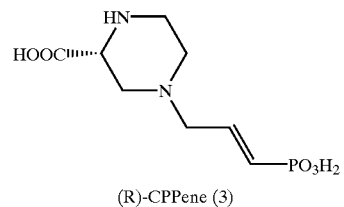
(R)-CPPene (3)
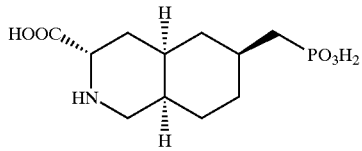
LY 235959 (4)
non-competitive
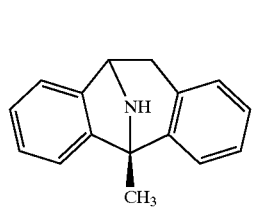
MK-801 (5)
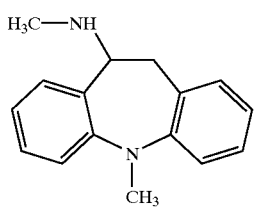
Metapramine (6)
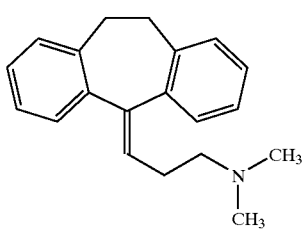
Amitriptyline (7)
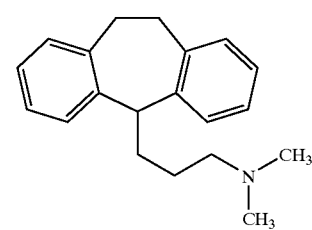
Imipramine (8)
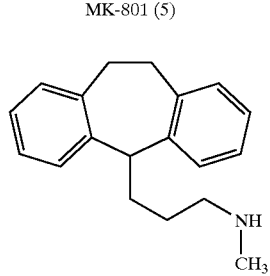
Desipramine (9)
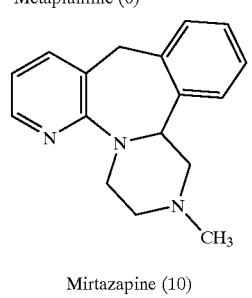
Mirtazapine (10)
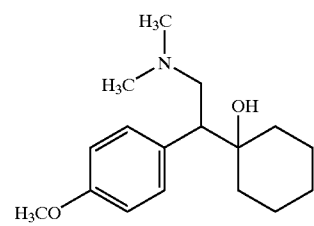
Venlafaxine (11)
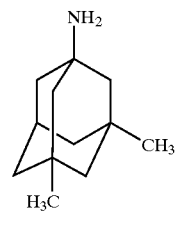
Memantine (12)
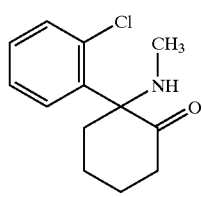
Ketamine (13)
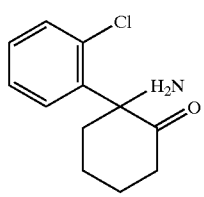
Norketamine (14)
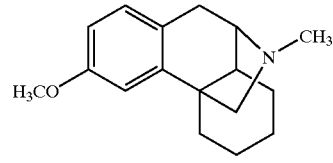
Dextromethorphan (15)
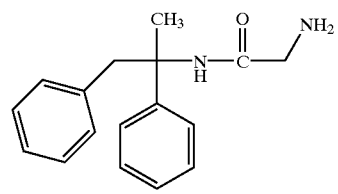
Remacemide (16)
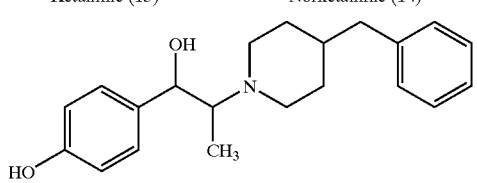
Ifenprodil (17)
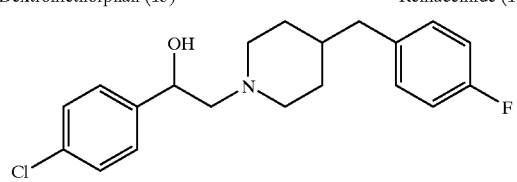
Eliprodil (18)
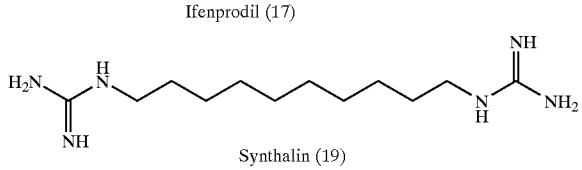
Synthalin (19)

Glycine antagonists (NMDA co-agonist site)
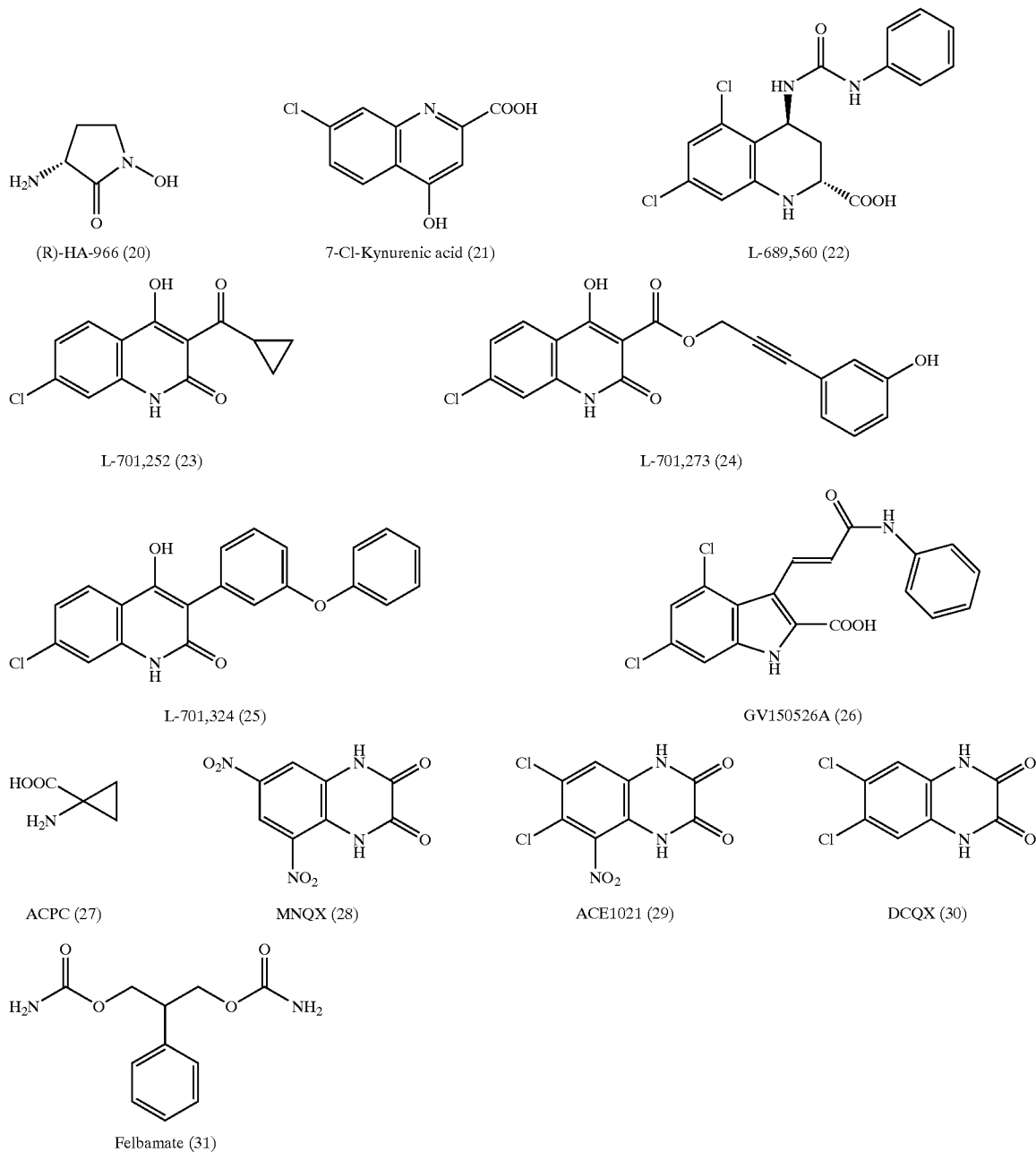
(R)-HA-966 (20)    7-Cl-Kynurenic acid (21)    L-689,560 (22)
L-701,252 (23)    L-701,273 (24)
L-701,324 (25)    GV150526A (26)
ACPC (27)    MNQX (28)    ACE1021 (29)    DCQX (30)
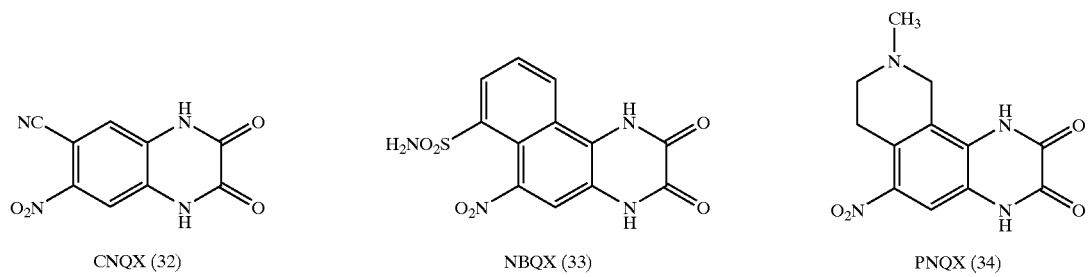
Felbamate (31)
AMPA receptor antagonists
competitive
CNQX (32)    NBQX (33)    PNQX (34)

-continued
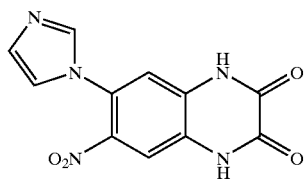
YM90K (35)
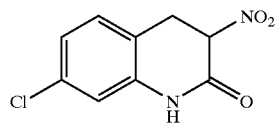
L-698,544 (36)
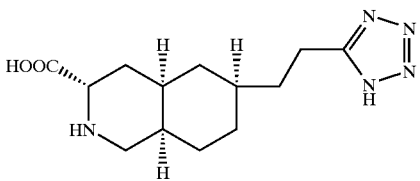
LY 215490 (37)
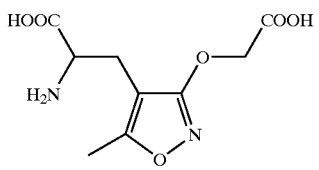
AMOA (38)
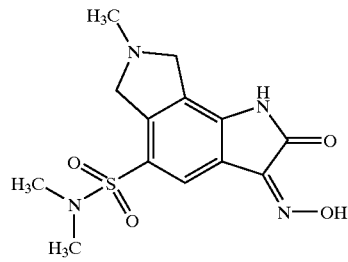
NS-257 (39)
non-competitive
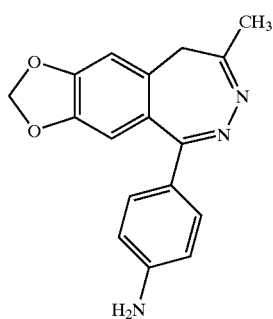
GYKI 52466 (40)
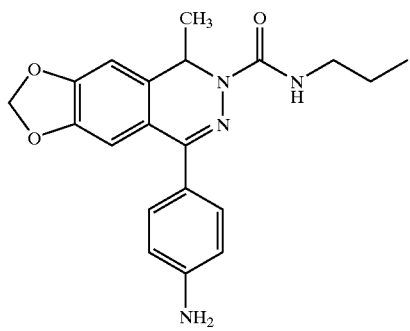
SYM 2206 (41)
Kainic acid receptor antagonist
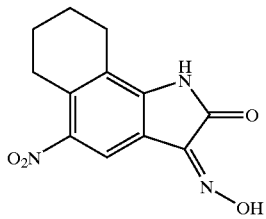
NS-102 (42)
Metabotropic glutamate receptor ligands
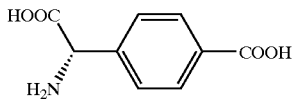
4CPG (43)
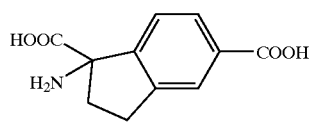
UPF523 (44)
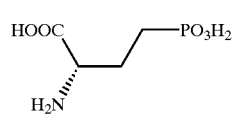
L-AP4 (45)

Neurokinin A (NK$_2$) receptor antagonists
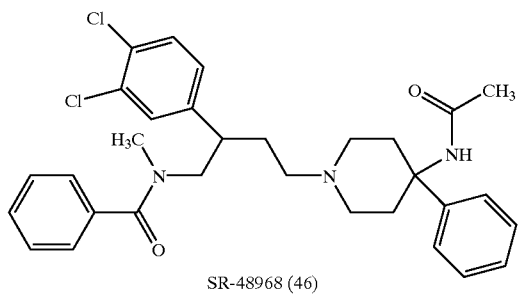
SR-48968 (46)
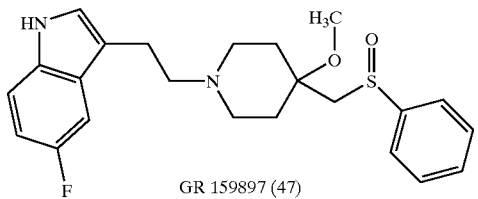
GR 159897 (47)
Bradykinin receptor antagonists
D-Arg-Arg-Pro-Hyp-Gly-Thi-Ser-D-Tic-Oic
Icatibant (48)
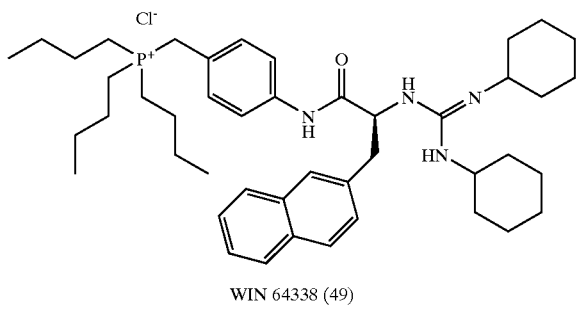
WIN 64338 (49)
NO synthase inhibitors
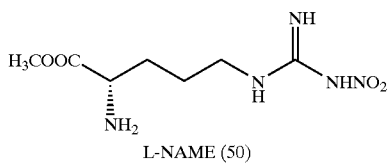
L-NAME (50)
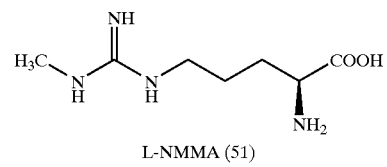
L-NMMA (51)
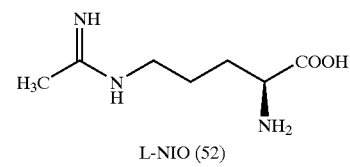
L-NIO (52)
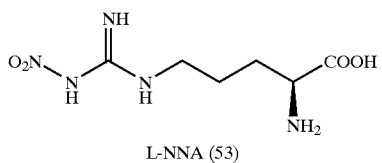
L-NNA (53)
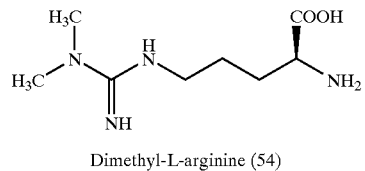
Dimethyl-L-arginine (54)
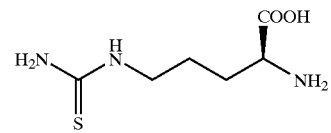
Thiocitrulline (55)
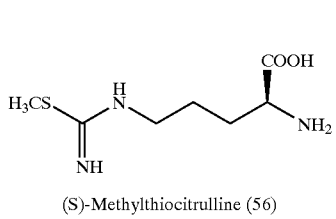
(S)-Methylthiocitrulline (56)
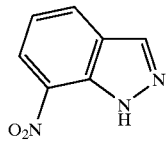
7-Nitroindazole (57)
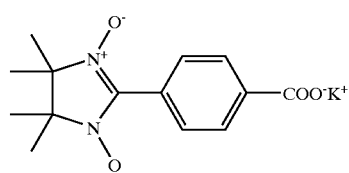
Potassium carboxy-PTIO (58)
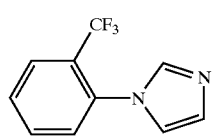
TRIM (59)
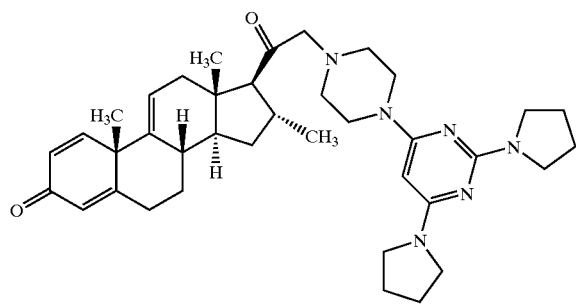
Tirilazad (60)

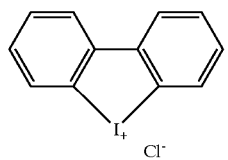
Diphenyleneiodonium chloride (61)
Guanylat cyclase inhibitor
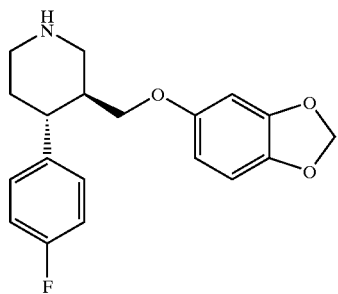
Paroxetine (62)
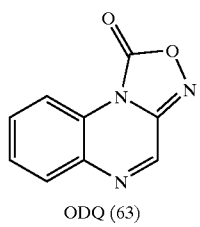
ODQ (63)
GABA-A receptor agonists
Gabapentin (64)
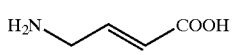
TACA (65)
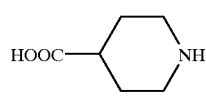
Isonipecotic acid (66)
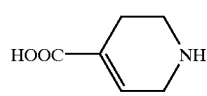
Isoguvacine (67)
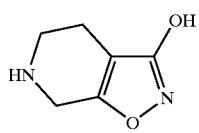
THIP (68)
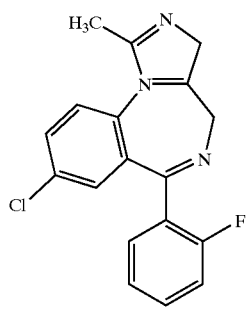
Midazolam (69)
GABA uptake inhibitors
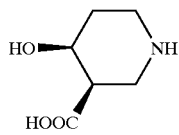
(±)-cis-4-Hydroxynipecotic acid (70)
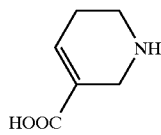
Guvacine (71)
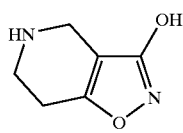
THPO (72)
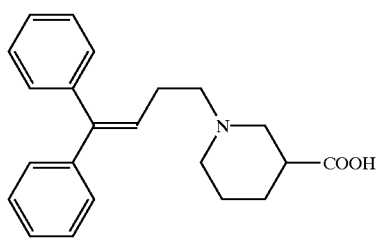
SKF 89976-A (73)
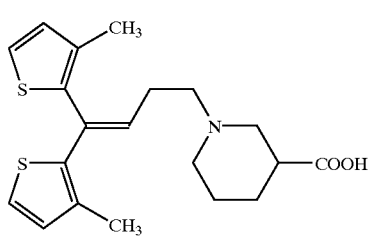
Tiagabine (74)

-continued
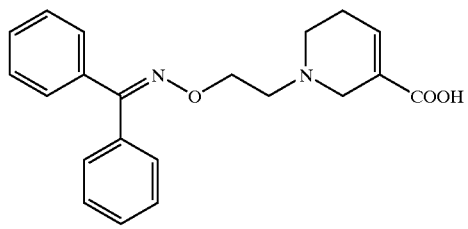
NO-711 (75)
GABA transaminase inhibitor
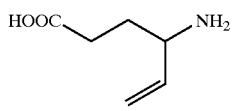
Vigabatrin (76)
Adenosin receptor ligands
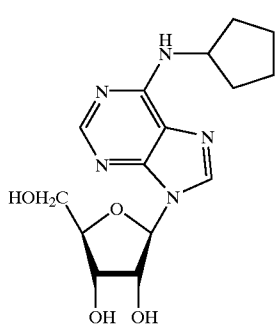
$N^6$-Cyclopentyladenosine (77)
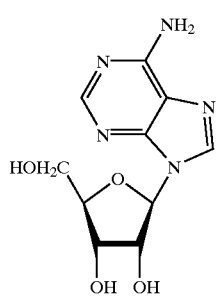
Adenosine (78)
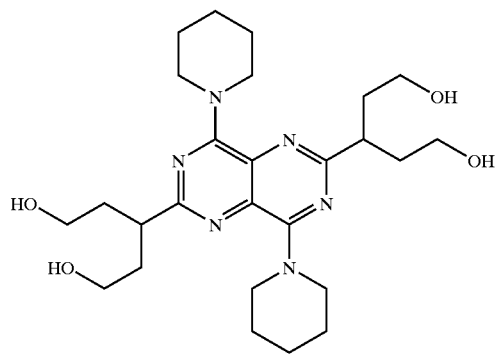
Dipyridamole (79)
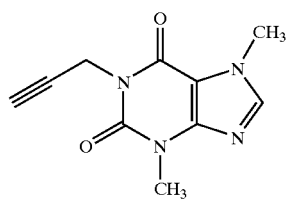
DMPX (80)
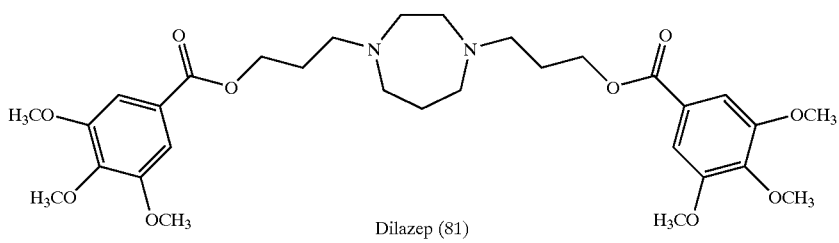
Dilazep (81)
5-HT'$_{2,3}$receptor antagonists
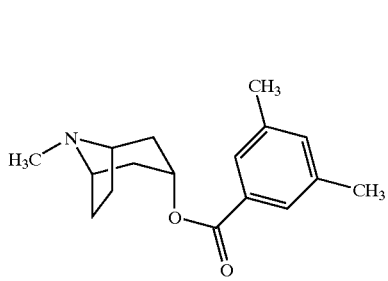
Tropanserin (82)
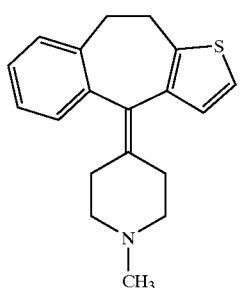
Pizotyline (83)

α-2 Receptor agonists

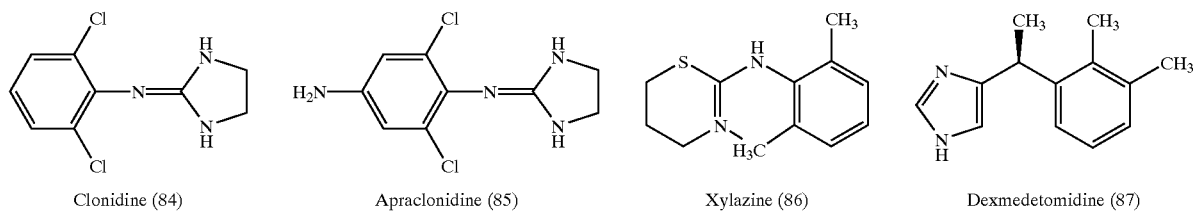

Clonidine (84)    Apraclonidine (85)    Xylazine (86)    Dexmedetomidine (87)

Na⁺ channel blockers

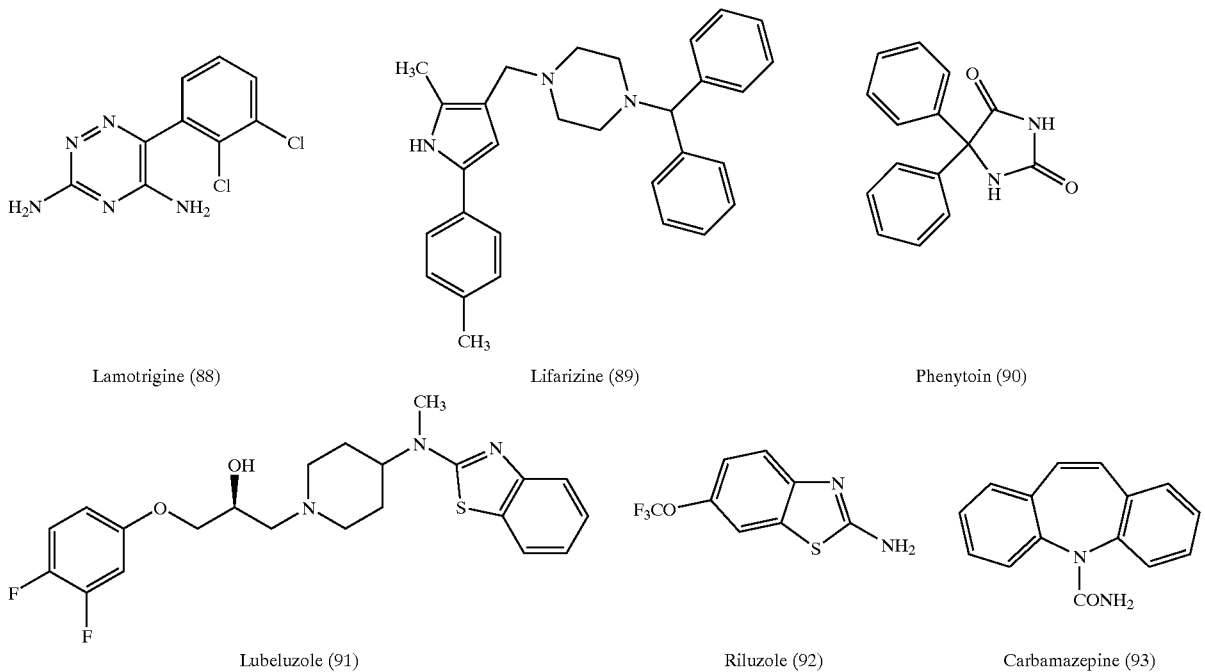

Lamotrigine (88)    Lifarizine (89)    Phenytoin (90)

Lubeluzole (91)    Riluzole (92)    Carbamazepine (93)

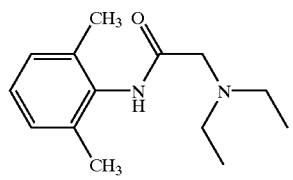   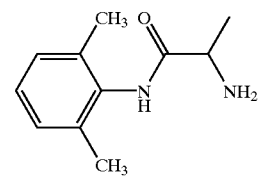   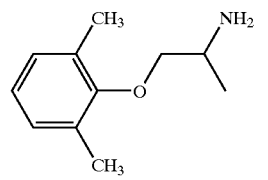

Lidocaine (94)    Tocainide (95)    Mexiletene (96)

Ca²⁺ channel blockers

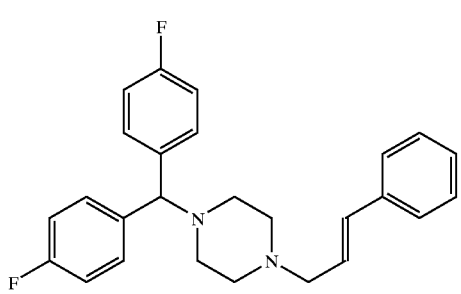   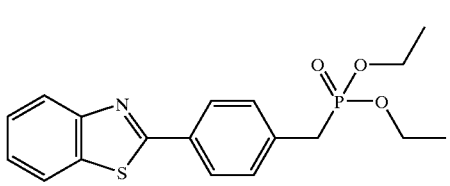

Flunarizine (97)    Fostedil (98)

Agents which inhibit neuronal transmission mediated by glutamate, in the central and/or peripheral nervous system, are capable of a) substantially inhibiting the production of glutamate, b) substantially inhibiting the release of glutamate, c) substantially counteracting the action of glutamate and/or d) substantially inhibiting the binding of glutamate to receptors for glutamate.

Examples of competitive NMDA receptor antagonists are nitrogen-containing heterocyclic compounds selected from diacidic piperidines, such as CGS 19755 (1), diacidic piperazines, such as (R)-CPP (2) and (R)-CPPene (3), phosphono amino acids such as LY 235959 (4) and derivatives of any of the above which are competitive NMA antagonists or prodrugs thereof.

Examples of non-competitive NMDA receptor antagonists are polycyclic amines, such as MK-801 (5); tricyclic antidepressants, such as Metapramine (6), Amitriptyline (7), Imipramine (8), Desipramine (9), Mirtazapine (10) or Venlafaxine (11); adamantanamines, such as Memantine (12); arylcyclohexylamines, such as Ketamine (13); arylcyclohexylamines, such as Norketamine (14), opioid derivatives, such Dextromethorphan (15); glycylamides, such as Remacemide (16); piperidinylethanols, such as Ifenprodil (17); piperidinylethanols, such as Eliprodil (18): diguanidines, such as Synthalin (19); γ-aminobutyric acid derivatives, such as Gabapentin (64), polycyclic amines, such as Pizotyline (83) or derivatives of any of the above which are non-competitive NMDA antagonists or prodrugs thereof.

Mirtazapine (10) and Venlafaxine (11) are conventionally known to have α-2 receptor antagonist effects, and their efficacy as antidepressants are thought to be exerted through a decrease in noradrenergic neurotransmission. However, it is presently believed that Mirtazapine and Venlafaxine may also have an effect on glutamate neurotransmission, potentially as non-competitive NMDA receptor antagonists. It is through this mechanism that the two substances are presumed to provide a method of treatment of tension-type headache according to the present invention.

Examples of Glycine antagonists are aminopyrrolidinones, such as (R)-HA-966 (20); kynurenic acid derivatives, such as 7-Cl-Kynurenic acid (21); tetrahydroquinolines, such as L-689,560 (22); kynurenic acid derivatives, such as L-701,252 (23), L-701,273 (24), L-701,324 (25); indoles such as GV150526A (26); glycine derivatives, such as ACPC (27); quinoxalinediones, such as MNQX (28), ACEA 1021 (29) and DCQX (30); dicarbamates, such as Felbamate (31) and derivatives of any of the above which are glycine antagonists or prodrugs thereof.

Examples of competitive AMPA receptor antagonists are quinoxalinediones, such as CNQX (32), NBQX (33), PNQX (34) and YM90K (35); dihydroquinolones, such as L-698, 544 (36); diacidic decahydroisoquinolines, such as LY 215490 (37); amino acid isoxazoles, such as AMOA (38); indoleoximes, such as NS-257 (39) and derivatives of any of the above which are competitive AMPA receptor antagonists or prodrugs thereof.

Examples of non-competitive AMPA receptor antagonists are 2,3-benzodiazepines, such as GYKI 52466 (40); phthalazines, such as SYM 2206 (41) and derivatives of any of the above which are non-competitive AMPA receptor antagonists or prodrugs there of.

Examples of competitive kainate receptor antagonists are indoleoximes, such as NS-102 (42) and derivatives thereof which are competitive kainic acid receptor antagonists or prodrugs thereof.

Examples of metabotropic receptor agonists are phenylglycines, such as 4CPG (43); amino acid indanes, such as UPF523 (44); phosphono amino acids, such as L-AP4 (45) and derivatives of any of the above which are metabotropic glutamate receptor agonists or prodrugs thereof.

Agents which inhibit neuronal transmission mediated by 5-HT, in the central and/or peripheral nervous system, are capable of a) substantially inhibiting the synthesis of 5-HT, b) substantially inhibiting the release of 5-HT, c) substantially counteracting the action of 5-HT and/or d) substantially inhibiting the binding of 5-HT to excitatory 5-HT, 5-HT$_{2,3}$ receptors.

Examples of 5-HT$_{2,3}$ receptor antagonists are tropan derivatives such as Tropanserin (82); polycyclic amines, such as Pizotyline (83) and derivatives of any of the above which are 5-HT$_{2,3}$ receptor antagonists or prodrugs thereof.

It is presently believed that Pizotyline (83) may also have effect on glutamate neurotransmission, potentially as a non-competitive NMDA receptor antagonist, as mentioned above. This mechanism is presumed, in addition to the 5-HT receptor antagonism, to provide a method of treatment of tension-type headache according to the present invention.

Agents which can inhibit neuronal transmission mediated by adenosine, in the central and/or peripheral nervous system, are capable of a) substantially inhibiting the synthesis of adenosine, b) substantially inhibiting the release of adenosine, c) substantially counteracting the action of adenosine, and/or d) substantially functioning as antagonists at adenosine A2 receptors.

Examples of adenosine A2 receptor antagonists are xanthine derivatives, such as DMPX (80) and derivatives thereof which are A2 receptor antagonists or prodrugs thereof.

Examples of adenosine uptake inhibitors are homopiperazine derivatives, such as Dilazep (81) and derivatives thereof which are adenosine uptake inhibitors or prodrugs thereof.

Agents which can inhibit neuronal transmission mediated by substance P, in the central and/or peripheral nervous system are capable of a) substantially inhibiting the synthesis of substance P, b) substantially inhibiting the release of substance P, c) substantially counteracting the action of substance P, and/or d) substantially inhibiting binding of substance P to receptors for substance P.

Agents which can inhibit neuronal transmission mediated by neurokinin A, in the peripheral and/or central nervous system, are capable of a) substantially inhibiting the synthesis of neurokinin A, b) substantially inhibiting the release of neurokinin A, c) substantially counteracting the action of neurokinin A, and/or d) substantially inhibiting binding of neurokinin A to receptors for neurokinin A (NK$_2$ receptors).

Examples of neurokinin A (NK$_2$) receptor antagonists are peptidomimetics, such as SR-48968 (37); peptidomimetics, such as GR 159897 (38) and derivatives thereof which are NK$_2$ receptor antagonists or prodrugs thereof.

Agents which can inhibit neuronal transmission mediated by bradykinin, in the peripheral and/or central nervous system, are capable of a) substantially inhibiting the production of bradykinin, b) substantially inhibiting the release of bradykinin, c) substantially counteracting the action of bradykinin and/or d) substantially inhibiting binding of bradykinin to receptors for bradykinin.

Examples of bradykinin receptor antagonists are peptidomimetics, such as Icatibant (48) and WIN 64338 (49) and derivatives of any of the above which are bradykinin receptor antagonists or prodrugs thereof.

Agents which can inhibit neuronal transmission mediated by CGRP, in the peripheral and/or central nervous system, are capable of a) substantially inhibiting the production of CGRP, b) substantially inhibiting the release of CGRP, c) substantially counteracting the action of CGRP and/or d) substantially inhibiting the binding of CGRP to receptors for CGRP.

Examples of CGRP receptor antagonists are CGRP 8–37.

Agents which can inhibit neuronal transmission mediated by PACAP, in the peripheral and/or central nervous system, are capable of a) substantially inhibiting the synthesis of PACAP, b) substantially inhibiting the release of PACAP, c) substantially counteracting the action of PACAP and/or d) substantially inhibiting binding of PACAP to receptors for PACAP.

Agents which can inhibit neuronal transmission mediated by nitric oxide, in the peripheral and/or central nervous system, are capable of a) substantially inhibiting the production of nitric oxide b) substantially counteracting the action of nitric oxide, c) substantially inhibiting the production of nitric oxide synthase (NOS) and/or d) substantially counteracting the action of nitric oxide synthase (NOS).

The interaction with neuronal transmission connected with pain perception connected with second order nociceptive neurons can comprise interaction with intracellular substances involved in this neuronal transmission, said interaction involving excitation mediated through the interaction with enzymes and second messengers in second order nociceptive neurons.

Preferred examples of the above mentioned intracellular substances are NOS, guanylate cyclase, and cGMP.

The interaction with neuronal transmission connected with pain perception, comprising interaction with NOS will preferably be performed by the administration of an effective amount of at least one agent which can substantially inhibit the production of the NOS, and/or substantially counteract the action of NOS.

Examples of NOS inhibitors are arginine derivatives, such as L-NAME (50), L-NMMA (51), L-NIO (52), L-NNA (53) and Dimethyl-L-arginine (54); citrulline derivatives, such as Thiocitrulline (55) and (S)-Methylthiocitrulline (56); indazoles, such as 7-Nitroindazole (57); imidazolin-N-oxides, such as Potassium carboxy-PTIO (58); phenylimidazoles, such as TRIM (59); 21-aminosteroids, such as Tirilazad (60); biphenyls, such as Diphenyleneiodinium chloride (61); piperidine derivatives, such as Paroxetine (62) and derivatives of any of the above which are NOS inhibitors or prodrugs thereof.

The interaction with neuronal transmission connected with pain perception, comprising interaction with guanylate cyclase can be performed by the administration of an effective amount of at least one agent, which substantially inhibits the production of guanylate cyclase and/or substantially counteracts the action of guanylate cyclase.

Examples of guanylate cyclase inhibitors are quinoxalines, such as ODQ (63) and derivatives thereof which are guanylate cyclase inhibitors.

The interaction with neuronal transmission connected with pain perception comprising interaction with cGMP can be executed by the administration of an effective amount of at least one agent which, in the peripheral and/or central nervous system, is capable or a) substantially inhibiting the production of guanylate cyclase, b) substantially counteracting the action of guanylate cyclase, c) substantially inhibiting the production of cyclic guanylate monophosphate (cGMP), d) substantially counteracting the action of cyclic guanylate monophosphate (cGMP) and/or e) substantially inhibiting any further steps in the reaction induced by cyclic guanylate monophosphate (cGMP), such as protein kinase C.

The activity of C-fibers, A-d-fibers and A-b-fibers on second order nociceptive neurons involves inhibitory neurotransmitter substances. Reduction of activity of C-fibers on second order neurons will normally be performed by administration of an effective amounts of at least one agent which is capable of a) substantially inhibiting the enzymatic degradation of said inhibitory transmitter substance, b) substantially enhancing the release of said inhibitory transmitter substance, c) substantially enhancing the action of said inhibitory transmitter substance and/or substantially activating the relevant receptor for said inhibitory transmitter substance.

Preferred examples of such inhibitory transmitter substances are selected from the group consisting of GABA, galanine, adenosine working through $A^1$ receptors, and norepinephrine.

Agents which can stimulate neuronal transmission mediated by GABA, in the peripheral and/or central nervous system, are capable of a) substantially enhancing the production of GABA, b) substantially inhibiting the enzymatic degradation of GABA, c) substantially enhancing the release of GABA, d) substantially enhancing the action of GABA and/or e) substantially activating receptors for GABA.

An example of a substance with GAB-enhancing activity is benzodiazepines, such as Midazolam (69) and derivatives thereof which are GABA activity enhancers or prodrugs thereof.

Examples of GABA-A receptor agonists are γ-aminobutyric acid derivatives, such as Gabapentin (64) and TACA (65); Isonipecotic acid (66) and Isoguvacine (67); 3-hydroxyisoxazoles, such as THIP (68) and derivatives of any of the above which are GABA-A agonists or prodrugs thereof.

Gabapentin is conventionally known to have GABA-A receptor agonist activity, though this mechanism has been questioned. However, it is presently believed that Gabapentin may also have antagonist effect on glutamate transmission, indirectly or directly, potentially as a non-competitive NMDA receptor antagonist, as mentioned above. It is through this mechanism, in addition to its gabaergic activity, that Gabapentin is presumed to provide a method of treatment of tension-type headache according to the present invention.

Examples of GABA uptake inhibitors are carboxypiperidine derivatives, such as (±)-cis-4-Hydroxynipecotic acid (70); carboxypyridine derivatives, such as Guvacine (71); 3-hydroxyisoxazoles, such as THPO (72); nipecotic acid derivatives, such as SKF 89976-A (73) and Tiagabine (74); guavacine derivatives, such as NO-711 (75) and derivatives of any if the above which are GABA uptake inhibitors or prodrugs thereof.

Examples of GABA transaminase inhibitors are γ-aminobutyric acid derivatives, such as Vigabatrin (76) and derivatives thereof which are GABA transaminase inhibitors or prodrugs thereof.

Agents which can stimulate neuronal transmission mediated by galanine, in the peripheral and/or central nervous system, are capable of a) substantially inhibiting the enzymatic degradation of galanine, b) substantially enhancing the release of galanine, c) substantially enhancing the action of galanine and/or d) substantially functioning as agonists at galanine receptors.

Agents which can stimulate neuronal transmission mediated by adenosine, in the peripheral and/or central nervous system, are capable of a) substantially inhibiting the enzymatic degradation of adenosine, b) substantially enhancing the release of adenosine, c) substantially enhancing the action of adenosine and/or d) substantially functioning as agonists at $A^1$ receptors.

Examples adenosine $A^1$ receptor agonists are adenosine derivatives, such as $N^6$-Cyclopentyladenosine (77);

adeninglucosides, such as Adenosine (78) and derivatives thereof which are A1 receptor agonists or prodrugs thereof.

An example of an enhancer of the action of adenosine is pyrimidine derivatives, such as Dipyridamole (79) and derivatives thereof which are adenosine uptake inhibitors or prodrugs thereof.

Agents which can stimulate neuronal transmission mediated by norepinephrine, in the peripheral and/or central nervous system, are capable of a) substantially inhibiting the enzymatic degradation of norepinephrine, b) substantially enhancing the release of norepinephrine, c) substantially enhancing the action of norepinephrine and/or substantially functioning as agonists at norepinephrine α-2 receptors.

Examples of α-2 receptor agonists are aminoimidazolines, such as Clonidine (84); aminoimidazolines, such as Apraclonidine (85); thiazinamines, such as Xylazine (86); imidazoles, such as Dexmedetomidine (87) and derivatives of any of the above which are α-2 receptor agonists or prodrugs thereof.

Reduction of activity of C-fibers on second order nociceptive neurons can be performed by administration of an effective amount of at least one agent which substantially blocks ion channels for $Na^+$ or $Ca^{2+}$ ions.

Examples of $Na^+$ channel blockers are triazines, such as Lamotrigine (88); diphenylmethylpiperazines, such as Lifarizine (89); hydantoins, such as Phenytoin (90); aminopiperidines, such as Lubelnzole (91); benzthiazoles, such as Riluzole (92); dibenzazepines, such as Carbamazepine (93); phenylamides, such as Lidocaine (94); phenylamides, such as Tocainide (95); aminoethylanisoles, such as Mexiletene (96) and derivatives of any of the above which are $Na^+$ it channel blockers or prodrugs thereof.

Examples of $Ca^{2-}$ channel blockers are diphenylmethylpiperazines, such as Flunarizine (97); arylphosphonic esters, such as Fostedil (98) and derivatives of any of the above which are $Ca^{2+}$ channel blockers or prodrugs thereof.

In accordance with normal usage the tern "agent", as used herein, is intended to designate an active substance per se, whether administered as such or in the form of a prodrug thereof, as well as a pharmaceutical composition comprising the substance or prodrug.

In addition to the specific substances mentioned above, derivatives thereof which show an activity of the same kind as the substance specifically mentioned are also useful for the purpose of the present invention. The kind of derivatives which come into consideration will, of course, depend on the specific character of the substance in question, but as general examples of derivatives which may be relevant for many of the substances may be mentioned introduction of or change of alkylsubstituents (typically with a chain length from one to five carbon atoms on aliphatic chains, cycloalkanes, aromatic and heterocyclic ring systems, introduction of or change of substituents such as halogens or nitro groups, change of ringsize for cycloalkanes, change of aromatic or heterocyclic ringsystems, change of alkylsubstituents on O-and N-atoms change of the alcohol part of ester groups, and bioisosteric replacement of functional groups, especially use of carboxylic acid bioisosteres such as phosphonic acids, phosphinic acids, tetrazoles, 3-hydroxyisoxazoles, sulphonamiders and hydroxyamic acids. Salts of acidic or basic compounds will be equally useful compared to the free acids or free bases. In case of racemic compounds, can racemates as well as pure enantiomeres and diastereoisomeres be used, and in the case of substances interacting with antagonist action be required. Of course, derivatives to be used should be derivatives which, in addition to their desired activity, shown an acceptably low toxicity, and, in general, the derivatives should, just as the substances themselves, be pharmaceutically acceptable.

The agent used according to the invention may be administered as such or in the form of a suitable prodrug thereof. The tern "prodrug" denotes a bioreversible derivative of the drug, the bioreversible derivative being therapeutically substantially inactive per se but being able to convert in the body to the active substance by an enzymatic or non-enzymatic process.

Thus examples of suitable prodrugs of the substances used according to the invention include compounds obtained by suitable bioreversible derivatization of one or more reactive or derivatizable groups of the parent substance to result in a bioreversible derivative. The derivatization may be performed to obtain a higher bioavailability of the active substance, to stabilize an otherwise unstable active substance, to increase the lipophilicity of the substance administered, etc.

Examples of types of substances which may advantageously be administered in the form of prodrugs are carboxylic acids, other acidic groups and amines which may be rendered more lipophilic by suitable bioreversible derivatization. As examples of suitable groups may be mentioned bioreversible esters or bioreversible amides. Amino acids arc typical examples of substances which, in their unmodified form, may have a low absorption upon administration. Suitable prodrug derivatives of amino acids will be one or both of the above-mentioned types of bioreversible derivatives.

For the administration to a patient, a substance having any of the activities as defined above or a prodrug thereof is preferably formulated in a pharmaceutical composition containing one or more substances having any of the activities as defined above or prodrugs thereof and one or more pharmaceutically acceptable excipients.

The substance or substances to be administered may be formulated in the compositions in pharmaceutically acceptable media, the character of which are adapted to the chemical character of the substance. The compositions may be adapted for administration by any suitable method, for example by oral, buccal, sublingual, nasal, rectal or transdermal administration. Substances which are suitable for oral administration may be formulated as liquids or solids such as syrups, suspensions or emulsions, tablets, capsules and lozenges. A liquid compositions will normally comprise a suspension or solution of the substance in a suitable liquid carrier or suitable liquid carriers, for example an aqueous solvent such as water, ethanol or glycerol, or a non-aqueous solvent, such as polyethylene glycol or an oil. The composition may also contain a suspending agent, preservative, flavouring or coloring agent. A composition in the form or a tablet can be made using any suitable pharmaceutical carrier or carriers used for preparing solid formulations, for example pharmaceutical grades of mannitol, lactose, starch, magnesium stearate, sodium saccharin, talcum, cellulose, glucose, sucrose, magnesium carbonate, and the like. For oral administration, a pharmaceutically acceptable non-toxic composition may be formed by incorporating normally used excipients, such as those carriers previously listed, and generally 1–95% of active ingredient that is, a substance used according to the invention or a prodrug thereof, often preferably 25–75% of the substance of the prodrug. A composition in the form of a capsule can be prepared using conventional encapsulation procedures. Thus, e.g., pellets containing the substance or prodrug in question may be prepared using any suitable carriers and then filled into a hard gelatin capsule, or a dispersion or suspension can be prepared using any suitable pharmaceutical carrier or carriers, such as aqueous gums, celluloses, silicates or oils and the dispersion or suspension can be filled into a soft gelatin capsule.

Examples of parenteral compositions are solutions or suspensions of the substances or prodrugs in a sterile aqueous carrier or parenterally acceptable oil, such as polyethylene glycol, polyvinyl pyrrolidene, lecithin, arachis oil or sesame oil. The compositions may contain pharmaceutically acceptable auxiliary substances as required to approximate physiological conditions, such as buffering agents, wetting agents, detergents, and the like. Additives may also include additional active ingredients, e.g. bactericidal agents, or stabilizers. If desired, the solution or suspension can be lyophilized and reconstituted with a suitable carrier such as a sterile aqueous carrier prior to administration.

Compositions for nasal administration can be formulated, e.g., as aerosols, drops, gels and powders. For aerosol administration, the substance or prodrug is preferably supplied in finely divided form along, with a surfactant and propellant. Typical percentages of the substance or prodrug are 0.01–20% by weight, preferably 1–10%. The surfactant must, of course, be non-toxic, and preferably soluble in the propellant. Representative of such surfactants are the esters or partial esters of fatty acids containing from 6 to 22 carbon atoms, such as caproic, octanoic, lauric, palmitic, stearic, linoleic, linoleic, olesteric and oleic acids with an aliphatic polyhydric alcohol or its cyclic anhydride such as, for example, ethylene glycol, glycerol, erythritol, arbitol, mannitol, sorbitol, the hexitol anhydrides derived from sorbitol, and the polyoxyethylene and polyoxypropylene derivatives of these esters. Mixed esters, such as mixed or natural glycerides may be employed. The surfactant may constitute 0.1–20% by weight of the composition preferably 0.25–5%. The balance of the composition is ordinarily propellant. Liquified propellants are typically gases at ambient conditions, and are condensed under pressure. Among suitable liquified propellants are the lower alkanes containing up to 5 carbons, such as butane and propane; and preferably fluorinated or fluorochlorinated alkanes. Mixtures of the above may also be employed. In producing the aerosol, a container equipped with a suitable valve is filled with the appropriate propellant, containing the substance according to the invention and surfactant. The ingredients arm thus maintained at an elevated pressure until released by action of the valve.

Compositions for buccal or sublingual administration are, for example, tablets, lozenges and pastilles, in which the substance or the prodrug is formulated with a carrier such as sugar and acacia, tragacanth; or gelatin and glycerol. Compositions for rectal administration are suitably in the form of suppositories containing a suppository base such as cocoa butter. Compositions for transdermal application are for example ointments, gels and transdermal patches.

The compositions are preferably in unit dosage form such as a tablet, capsule or ampoule. Each dosage unit for oral administration will normally contain from 1 to 500 mg (and for parenteral administration preferably from 0.1 to 25 mg) of a substance used according to the invention or a prodrug therefore calculated as the free active substance.

The physiologically acceptable substances or prodrugs are normally administered in a daily dosage of between 1 mg and 500 mg for a adult person, usually between 10 mg and 400 mg, such as between 10 mg and 250 mg orally, or an intravenous, subcutaneous or intramuscular dose of between 0.1 mg and 100 mg, preferably between 0.1 and 50 mg, such as between 1 mg and 25 mg of the substance. The substance or prodrug is preferably administered 1 to 4 times daily. As mentioned above, the administration is normally aimed at maintaining a therapeutically effective serum concentration of the substance for at least one month, preferably at least two months or at least three months. Controlled release type compositions will often be suitable for maintaining an effective serum concentration with a small number of daily unit dosages.

Abbreviations; V: Trigeminal nerve, C2 and C3: Second and third cervical segment of the spinal cord, PAG: Periaquaductal grey, DRN: Dorsal raphe nuclei, on-cells: cells in ventromedial medulla, which activate pain pathways, for instance by reducing the threshold in the tail flick test. C: C fibers. Ad: A-d-fibers. Ab: A-b-fibers.

FIG. 2 depicts stimulus-response functions in trapezius muscle.

Figure 1:
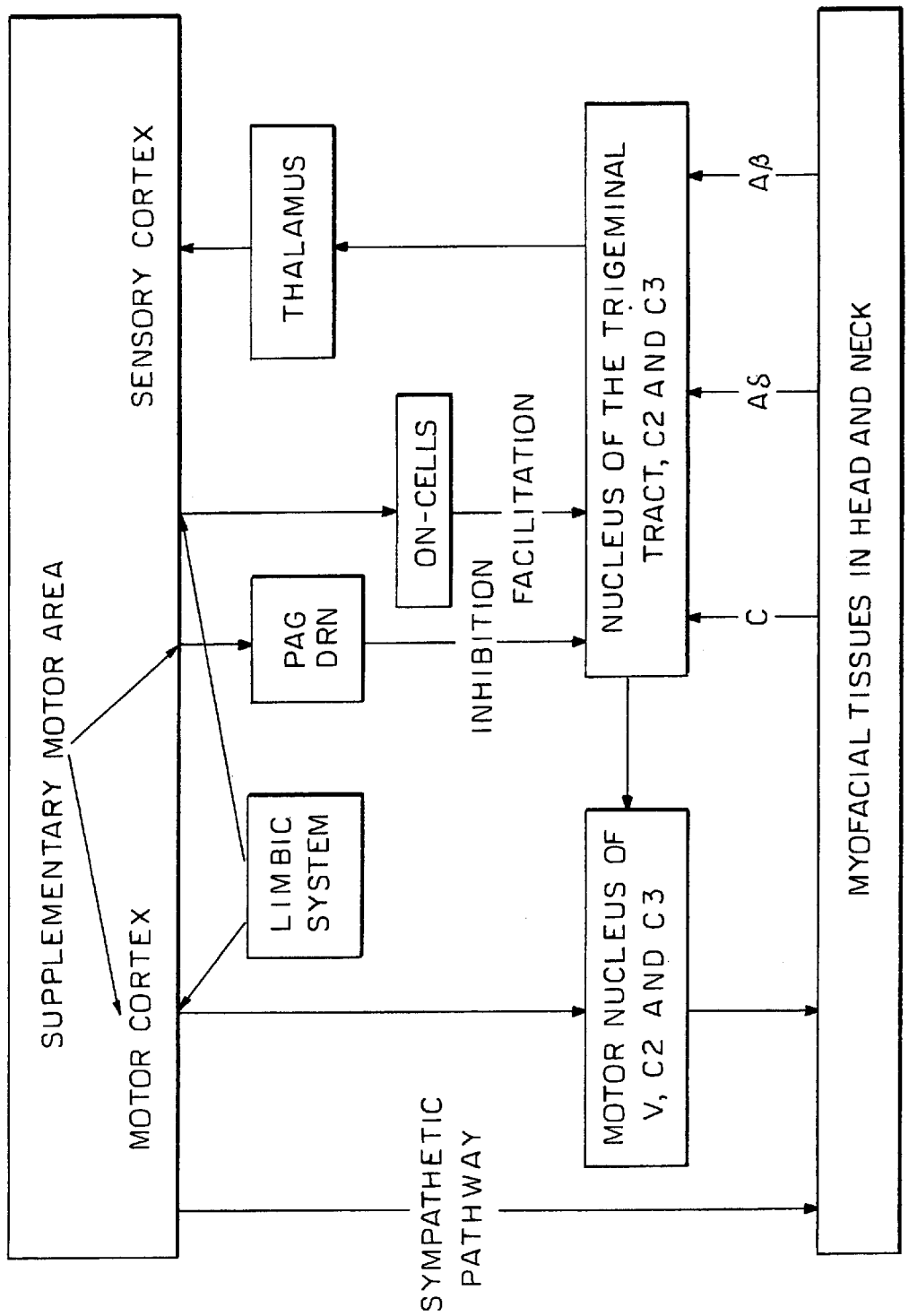
FIG. 1 shows the model for the development or tension-type headache.
Figure 2A:
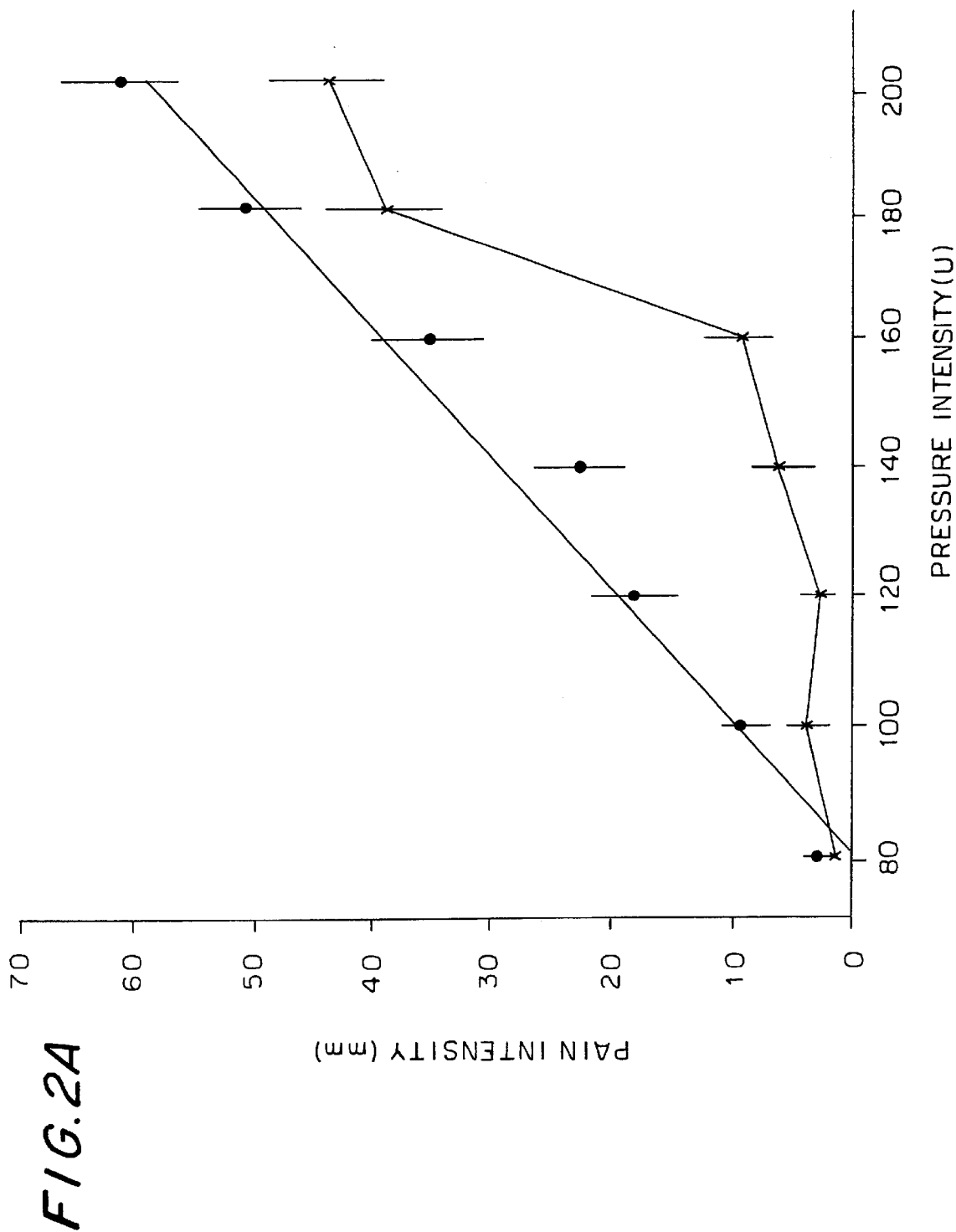
Figure 2B:
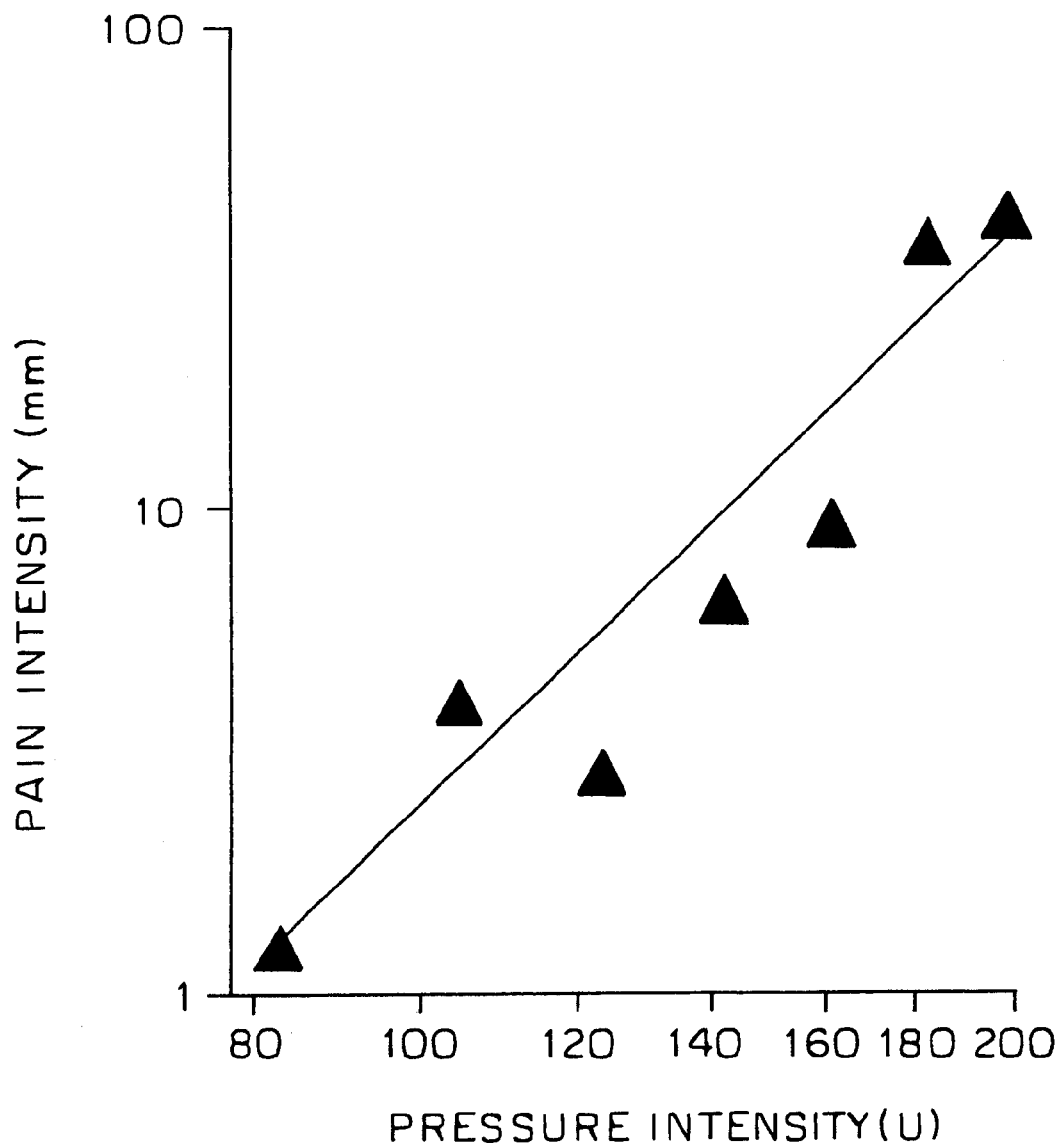

Stimulus-response functions for pressure versus pain in the trapezius muscle in 40 patients with chronic tension-type headache (dots) and in 40 control subjects (triangles) (mean±SE). Patients were significantly more tender than controls. P=0.002. In patients, the stimulus-response function was approximately linear with a slope (b)=0.50±0.04 mm/U, P=0.00004 (FIG. 2A). In contrast pain intensities increased in a positively accelerating fashion with increasing pressure intensities in controls, a relation that was well described by a power function. This was demonstrated by obtaining an approximately linear relation between pressure and pain in a double logarithmic plot, b=3.8±0.61 logmm/logU, P=0.002 (FIG. 2B).

Figure 3A:
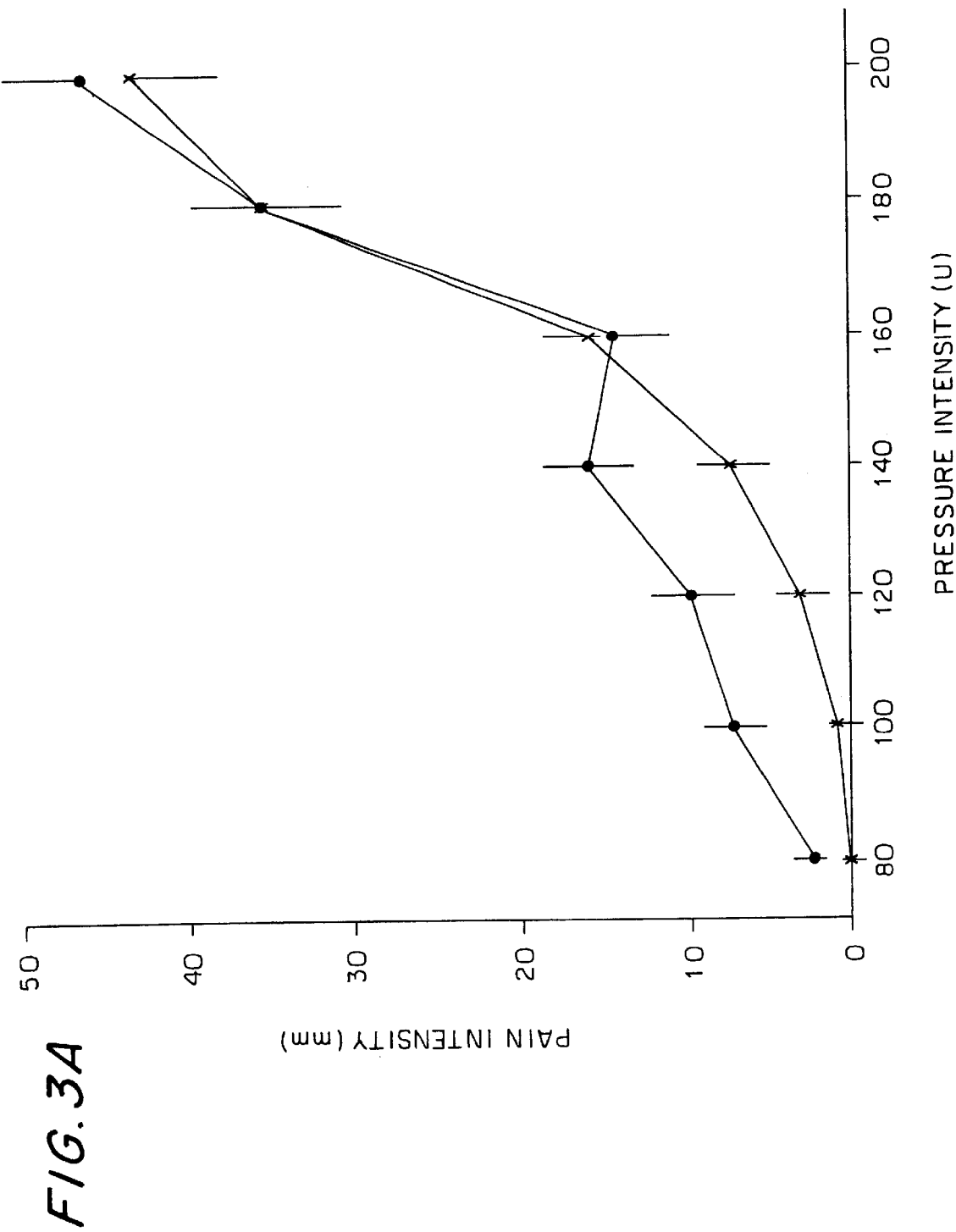

FIG. 3 depicts stimulus-response functions in temporal muscle.

Figure 3B:
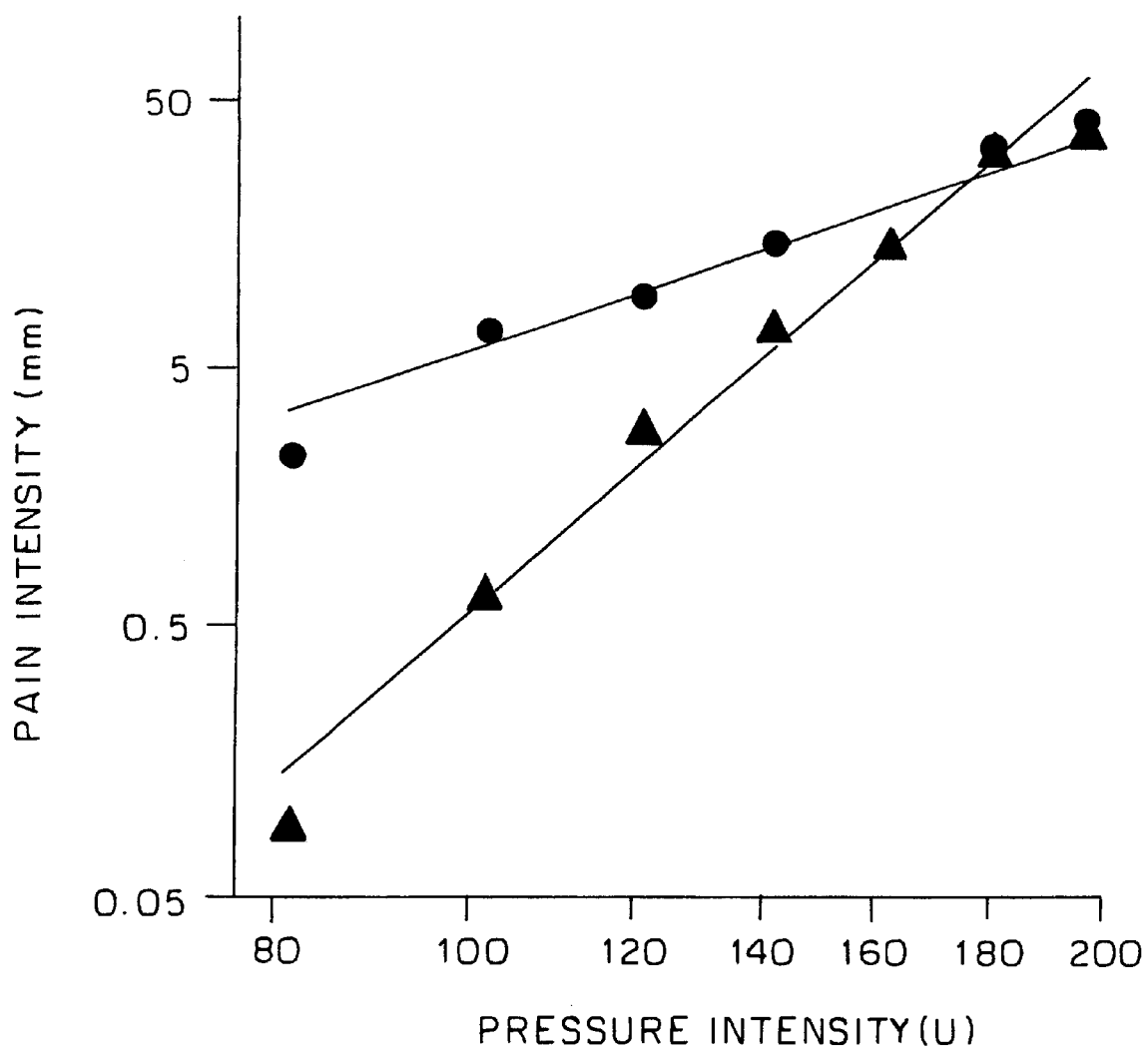

Stimulus-response functions for pressure versus pain in the temporal muscle in 40 patients (dots) and in 40 controls (triangles) (mean±SE) Patients were sightly more tender than controls, but the difference was not statistically significant, P=0.42. In both groups, pain intensities increased in a positively accelerating fashion with increasing pressure intensities (FIG. 3A) This was demonstrated by obtaining approximately linear relations between pressure and pain in a double logarithmic plot: patients b=3, 0=0.36 logmm/logU, P=0.0002; controls b=6, 7=0.36 logmm/log U, P=0.00001 (FIG. 3B).

FIG. 4 depicts stimulus-response functions in trapezius muscle.

Figure 4A:
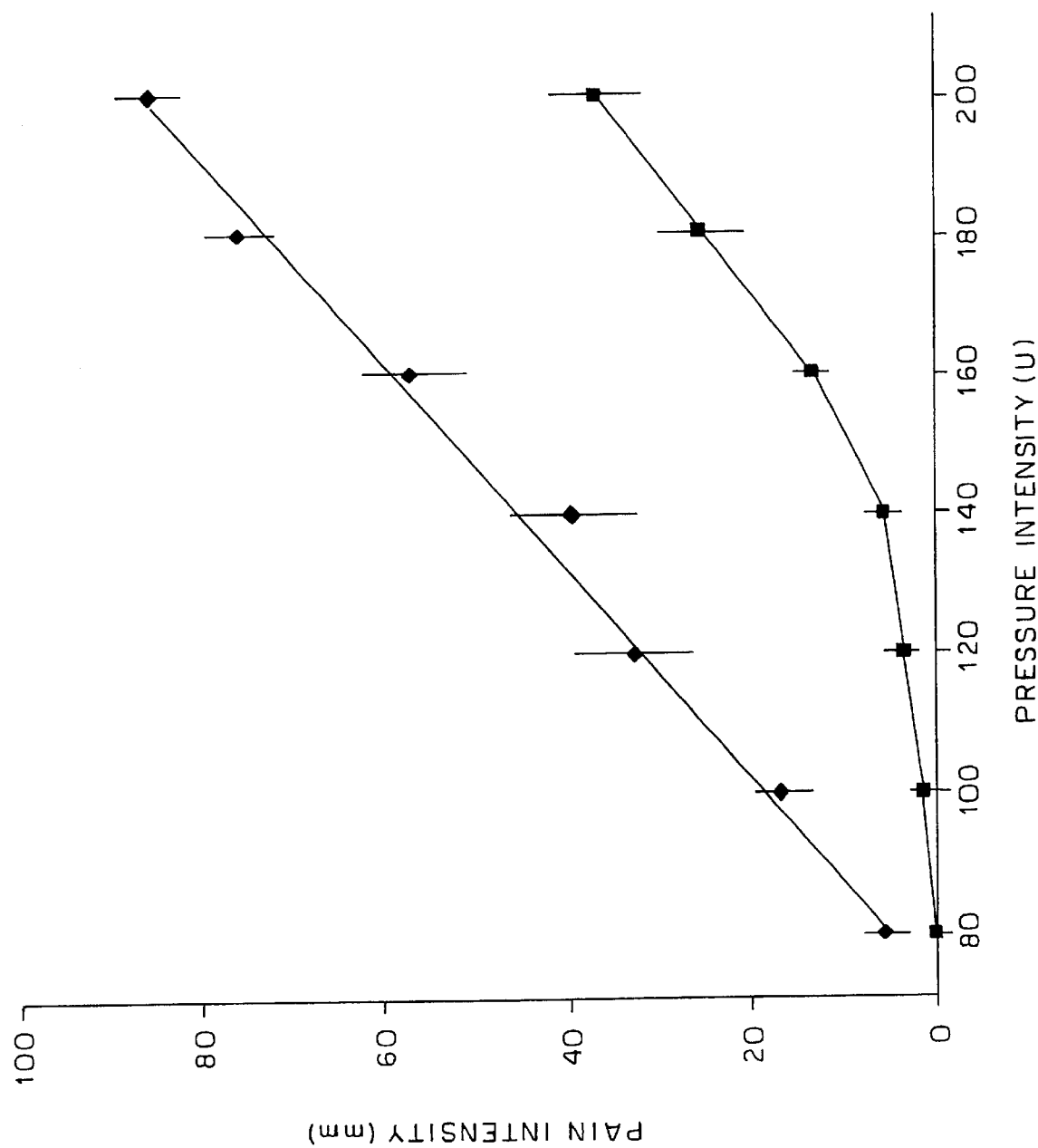
Figure 4B:
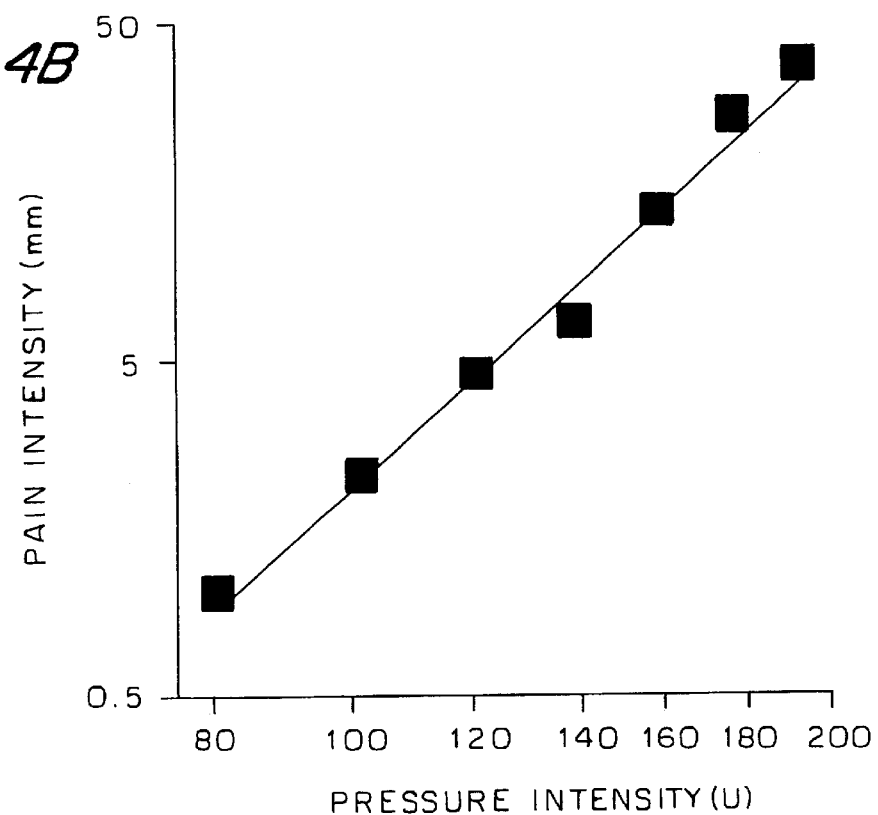

Stimulus-response functions for pressure versus pain in the trapezius muscle in the 20 most tender patients (diamonds) and in the 20 least tender patients (squares) (mean±SE). In the most tender patients, the stimulus-response function was linear, b=0, 69±0.03 mm/U, P<0.00001. In contrast, pain intensities increased in a positively accelerating fashion with increasing pressure intensities in the least tender patients (FIG. 4A). This was demonstrated by obtaining a linear relation between pressure and pain in a double logarithmic plot, b=4, 0±0.18 logmm/logU, P<0.00001 (FIG. 4B).

Figure 5:
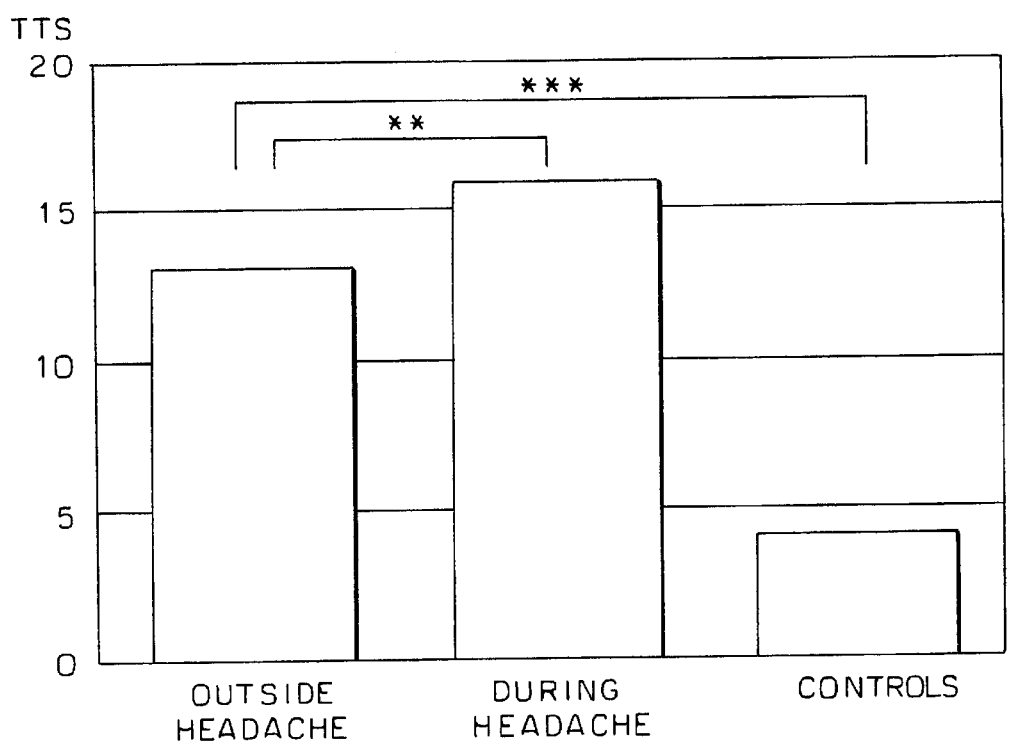

FIG. 5 shows Total Tenderness Scores in patients.

The Total Tenderness Scores (TTS) in patients outside and during a headache episode and in controls. Median values are given (*indicate $p<10^{-5}$ and indicate p=0.01, Wilcoxon's test).

Figure 6:
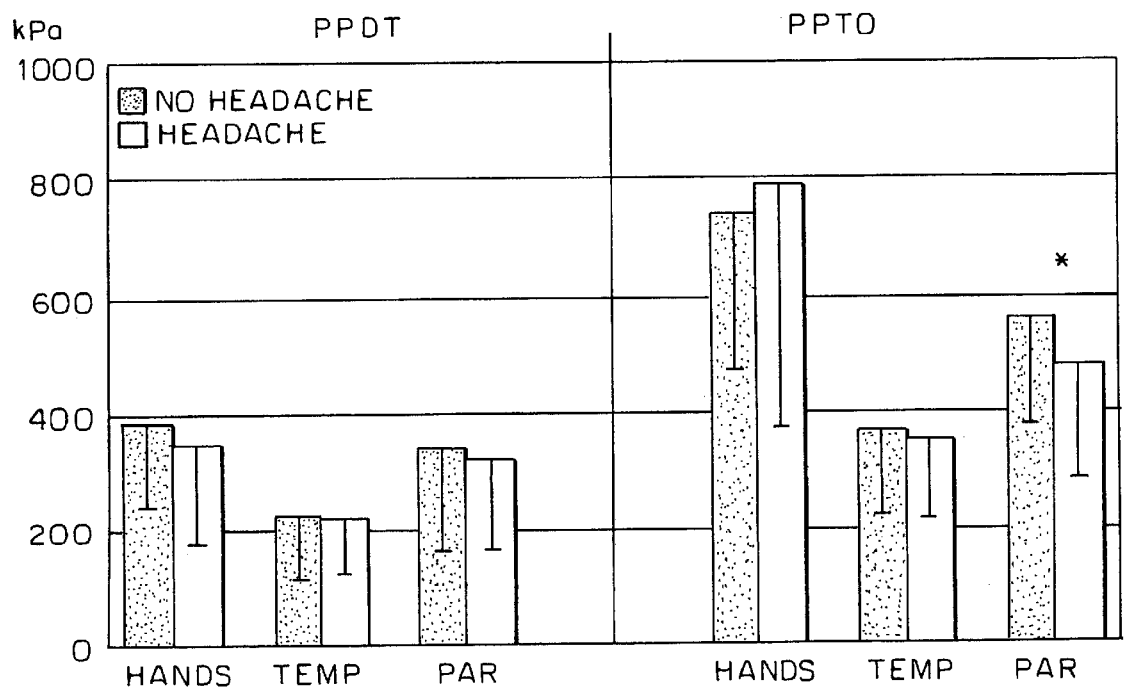

FIG. 6 shows Pressure Pain Thresholds (PPDT) and Pressure Pain Tolerances (PPTO) in patients.

Pressure Pain Thresholds (PPDT) and Pressure Pain Tolerances (PPTO) in patients outside (closed bars) and during a headache episode (open bars). Mean values of left and right side are given in kPa with SD as vertical bars (*indicate $p<0.05$, Wilcoxon's test).

Figure 7:
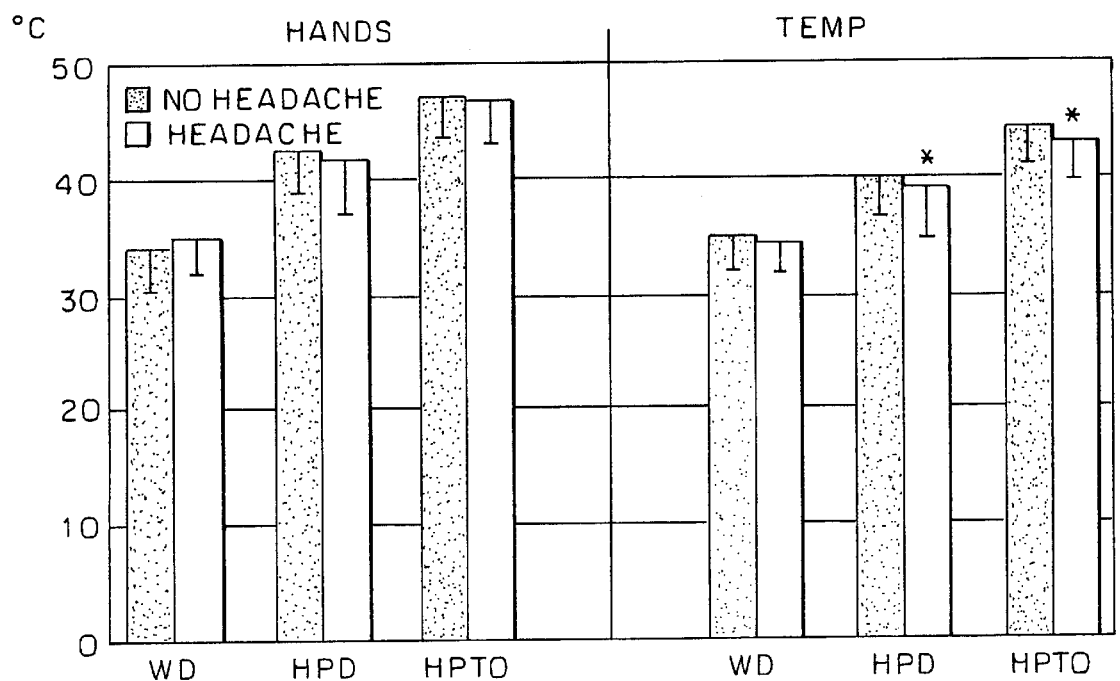

FIG. 7 shows thermal thresholds in the hands and temporal (Temp) regions of patients.

Thermal thresholds in the hands and temporal (Temp) regions of patients outside (closed bars) and during a headache episode (open bars). WD indicate warmth detection, HPD heat pain detection and HPTO heat pain tolerance thresholds. Mean values of left and right side are given in ° C. with SD as vertical bars (*indicate $p<0.05$, Wilcoxon's test).

FIG. 8 depicts EMG-amplitude levels from the temporal and trapezius muscles of patients.

Figure 8A:
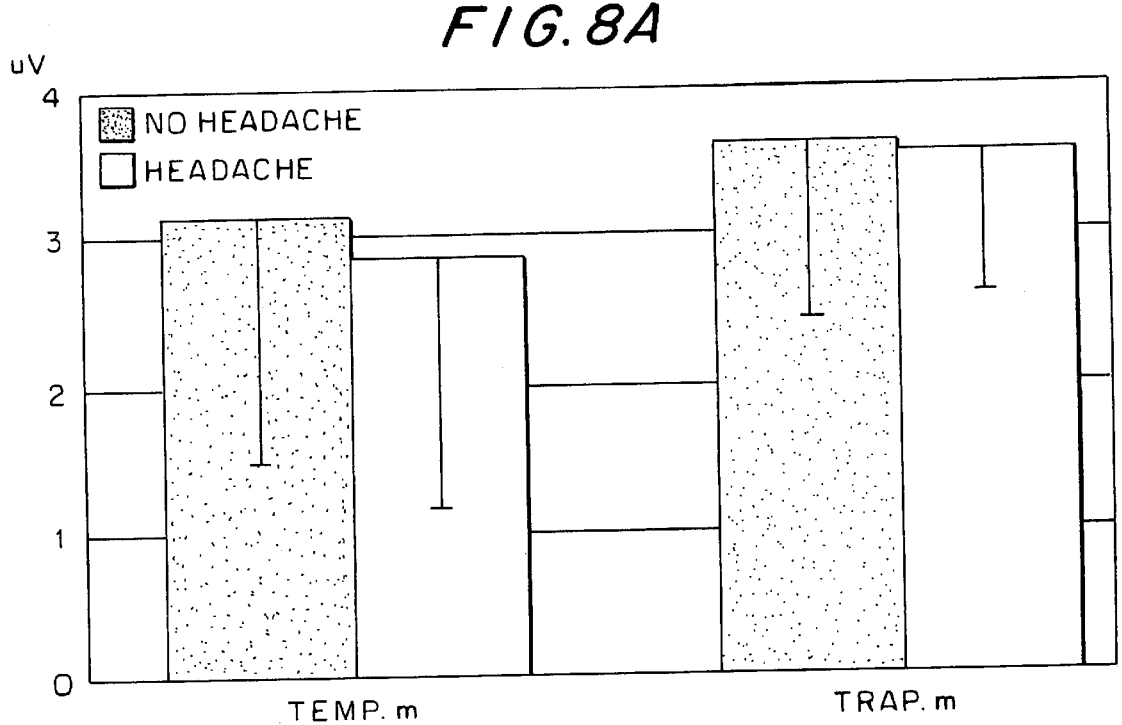
Figure 8B:
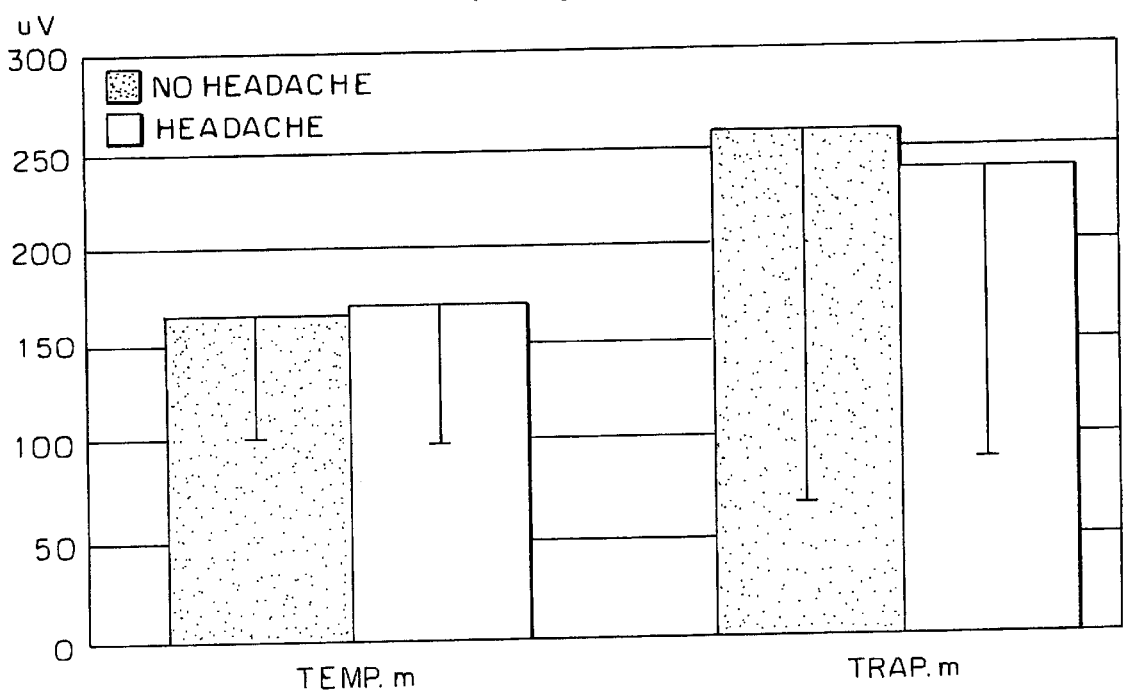

EMG-amplitude levels from the temporal and trapezius muscles of patients outside (closed bars) and during a headache episode (open bars). FIG. 8A indicates the resting condition and FIG. 8B the maximal voluntary contraction Mean values of left and right side are given in uV with SD as vertical bars.

FIG. 9 depicts pain intensities in patients and controls.

Pain intensities in those patients (filled circles) and controls (open circles) who developed tension-type headache after a 30 minutes sustained clenching procedure. The ordinate indicates the mean pain intensity in mm as recorded on a 100 mm visual analogue scale. The abscissa indicates the time after the clenching procedure(*$p<0.05$, Mann-Whitney's test)

Figure 10:
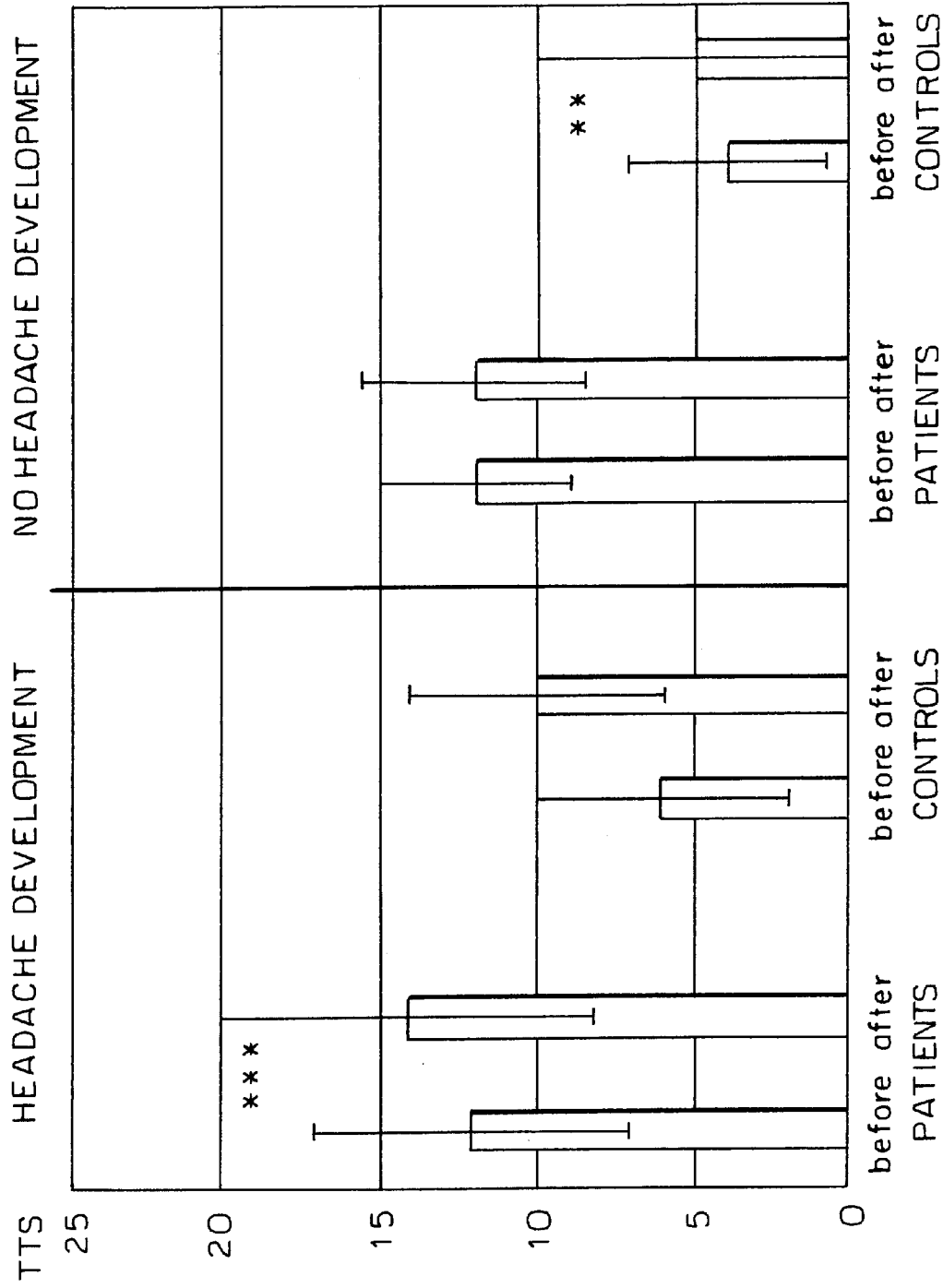

FIG. 10 shows Total Tenderness Scores (TTS) in patients and in controls

Total Tenderness Scores(TTS) in patients and in controls before and 90 minutes after experimental tooth clenching with respect to development of headache. Median values with quartiles are given. (indicate $p<0.01$. *$p<0.001$, Wilcoxon's test).

Figure 11A:
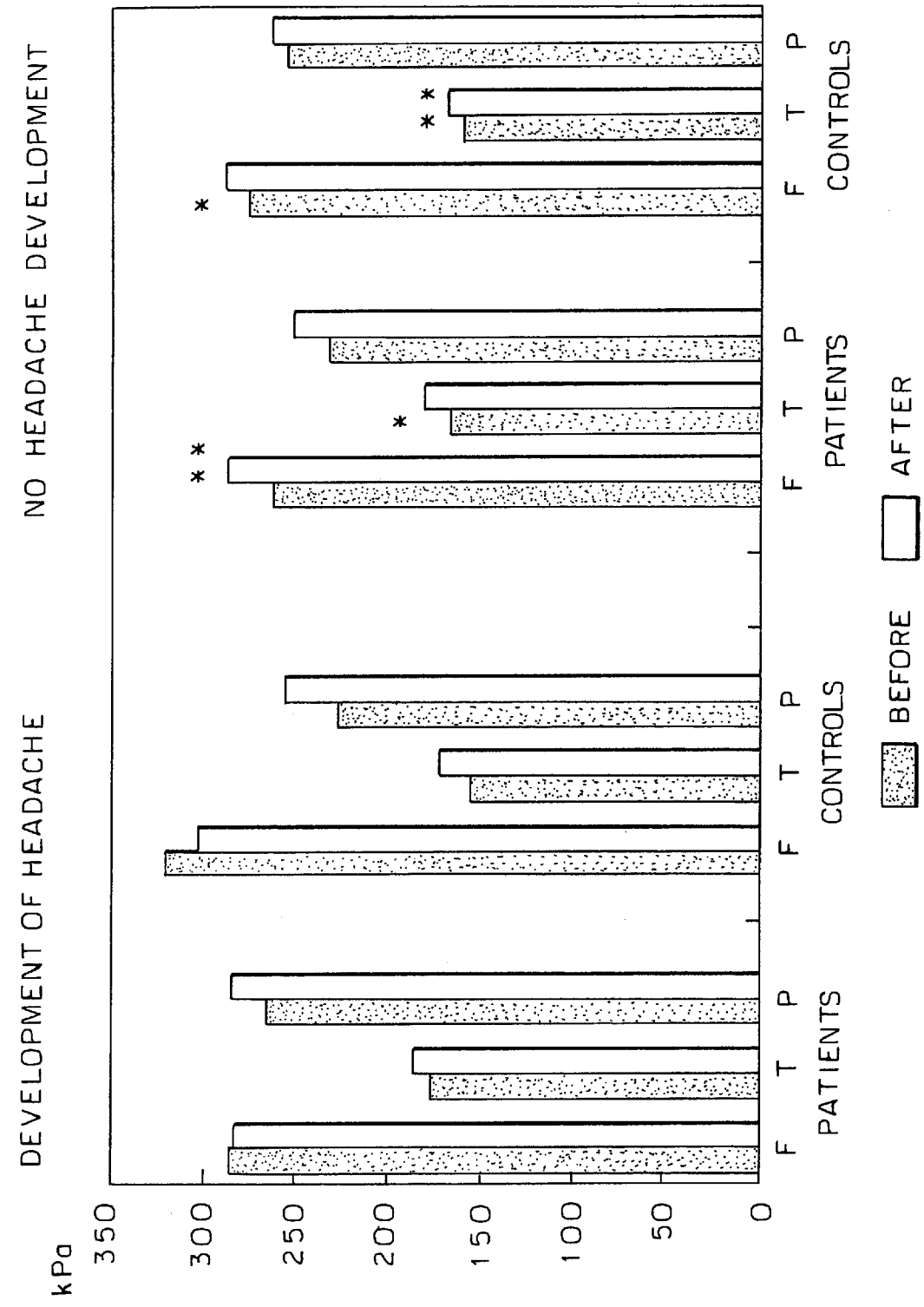

FIG. 11A shows the Pressure Pain Detection Thresholds and Pressure Pain Tolerances in patients and controls.

Figure 11B:
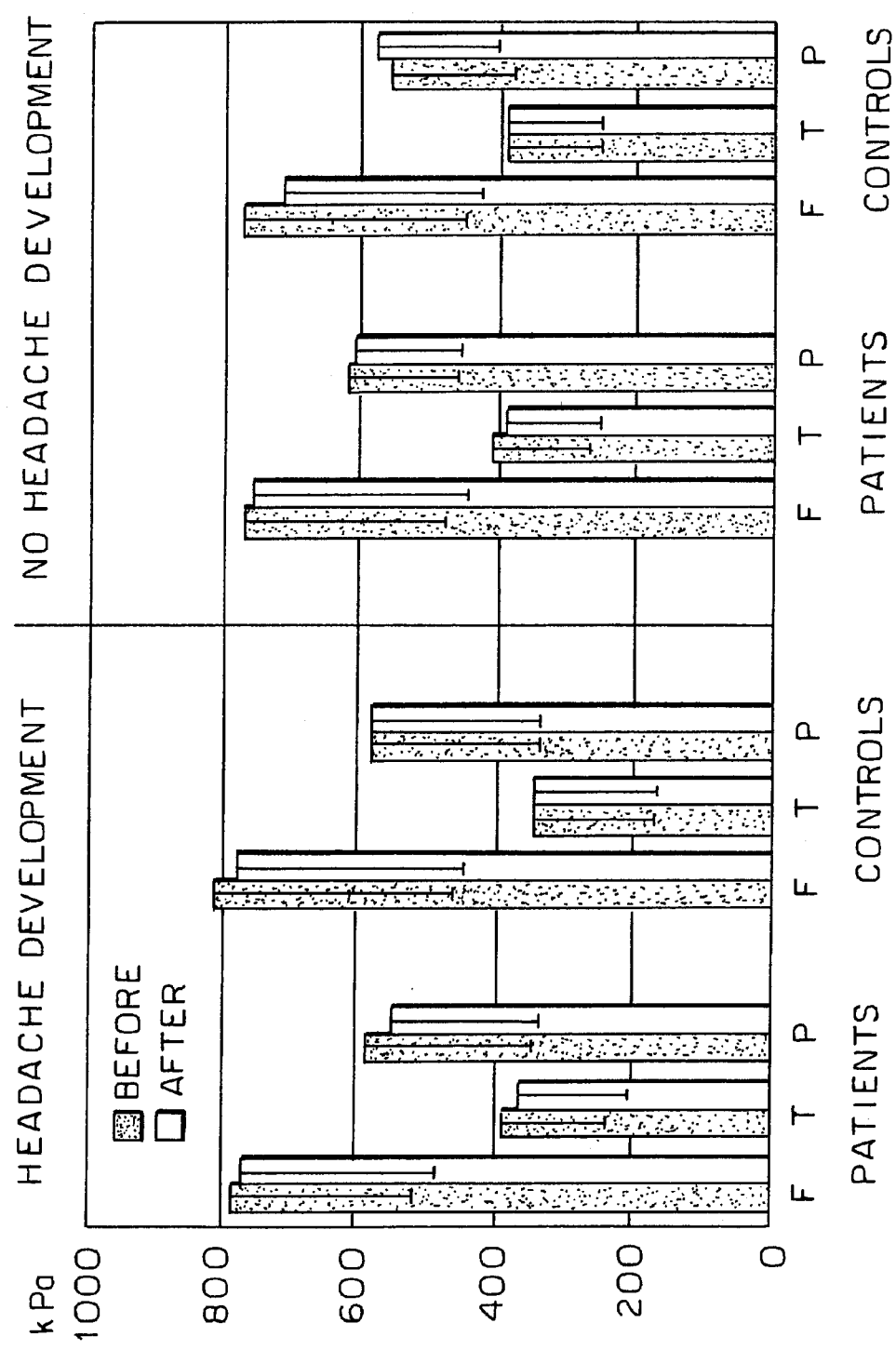

FIG. 11A shows the Pressure Pain Detection Thresholds and FIG. 11B the Pressure Pain Tolerances from fingers (F), temporal (T) and parietal (P) regions from patients and controls before (filled bars) and after clenching (open bars) with respect to development of headache Mean values of right and left side with SD are given in kPa (*indicate $p<0.05$, **$p<0.01$, Wilcoxon's test).

Figure 12:
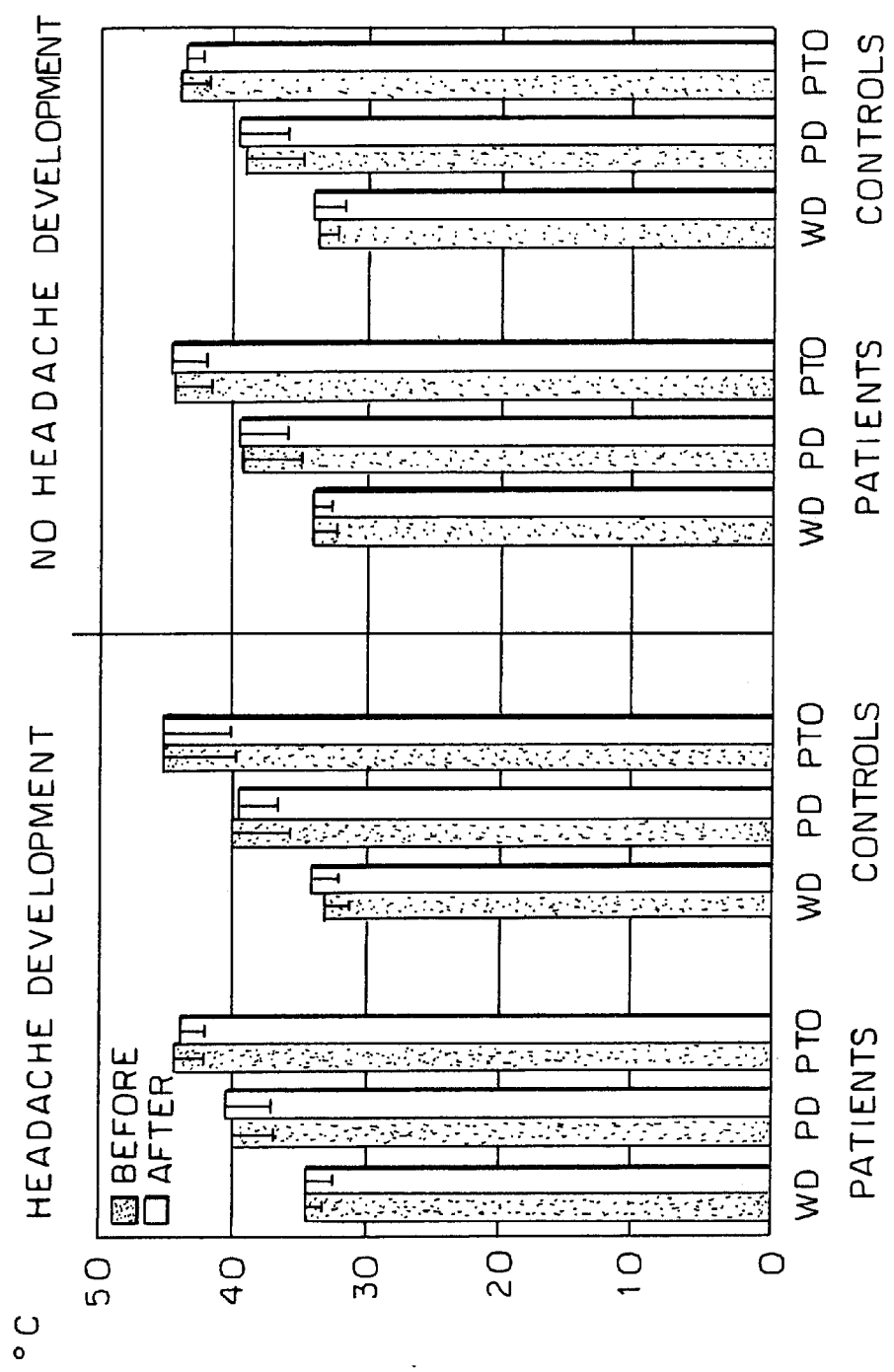

FIG. 12 shows thermal thresholds in the temporal region of patients and controls.

Thermal thresholds in the temporal region of patients and controls before (filled bars) and after clenching (open bars) with respect to headache development. WD indicate warmth detection, PD heat pain detection and PTO heat pain tolerance. Mean values of right and left side pith SD are given in ° C.

FIG. 13 shows the EMG-amplitudes in temporal and trapezius muscles of patients and controls.

Figure 13A:
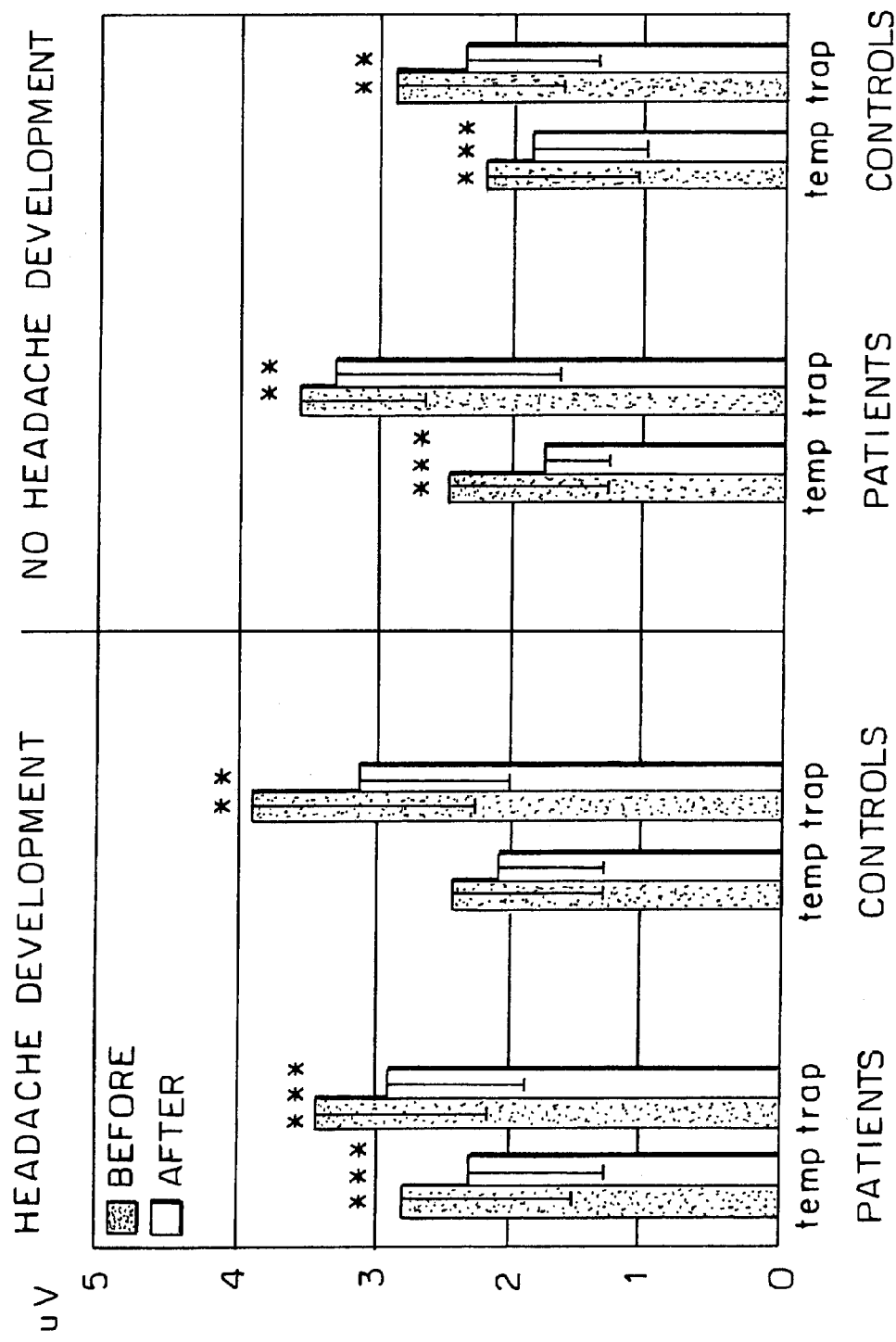
Figure 13B:
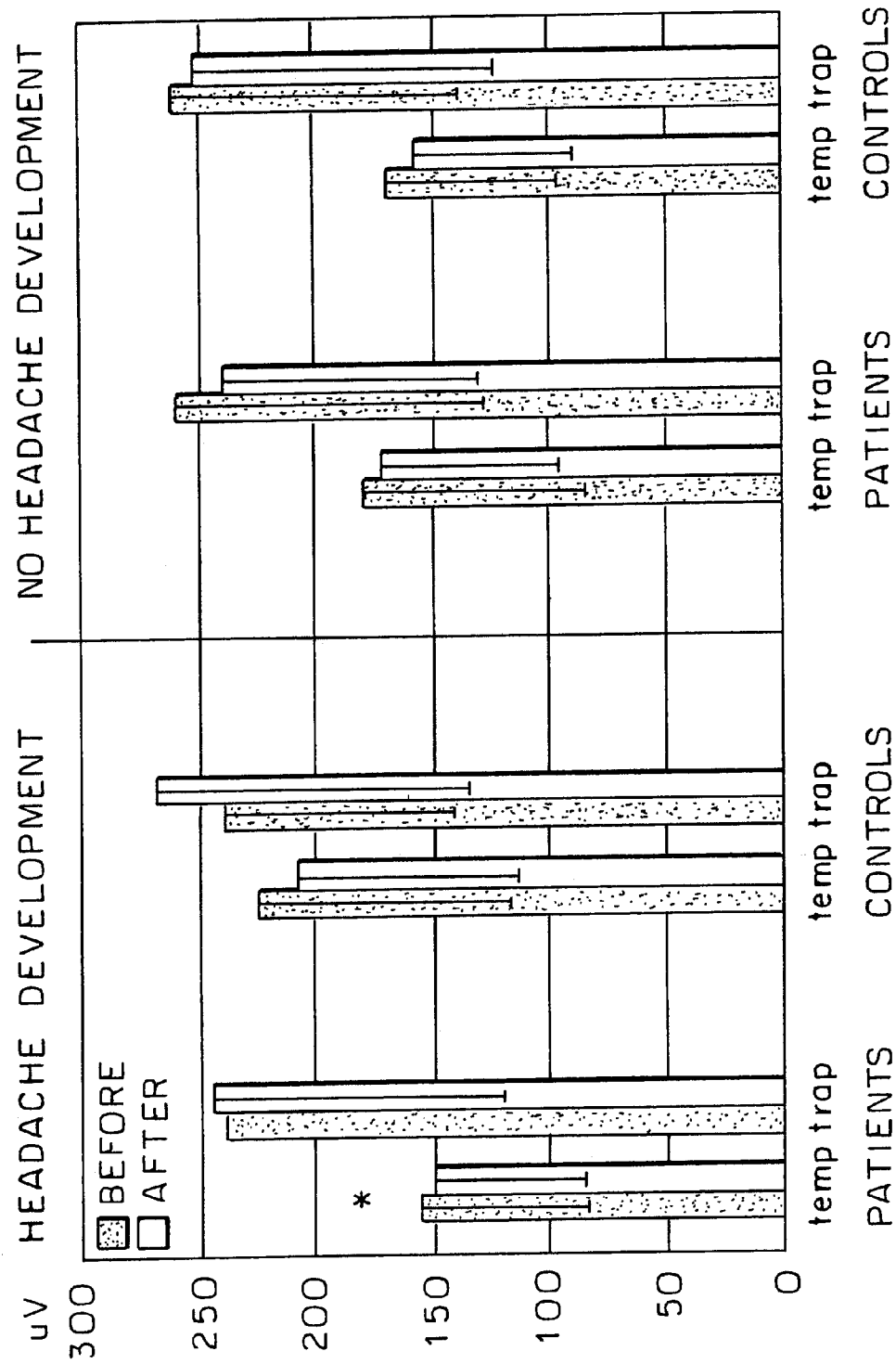

FIG. 13A shows the EMG-amplitudes (Root Mean Square-values) during resting condition and FIG. 13B during the maximal voluntary contraction in temporal (temp) and trapezius (trap) muscles from patients and controls before (filled bars) and after clenching (open bars) with respect to headache development. Mean values of left and right side with SD are given in uV (*indicate $p<0.05$, $p<0.01$ and *$p<0.001$, Wilcoxon's test).

Figure 14:
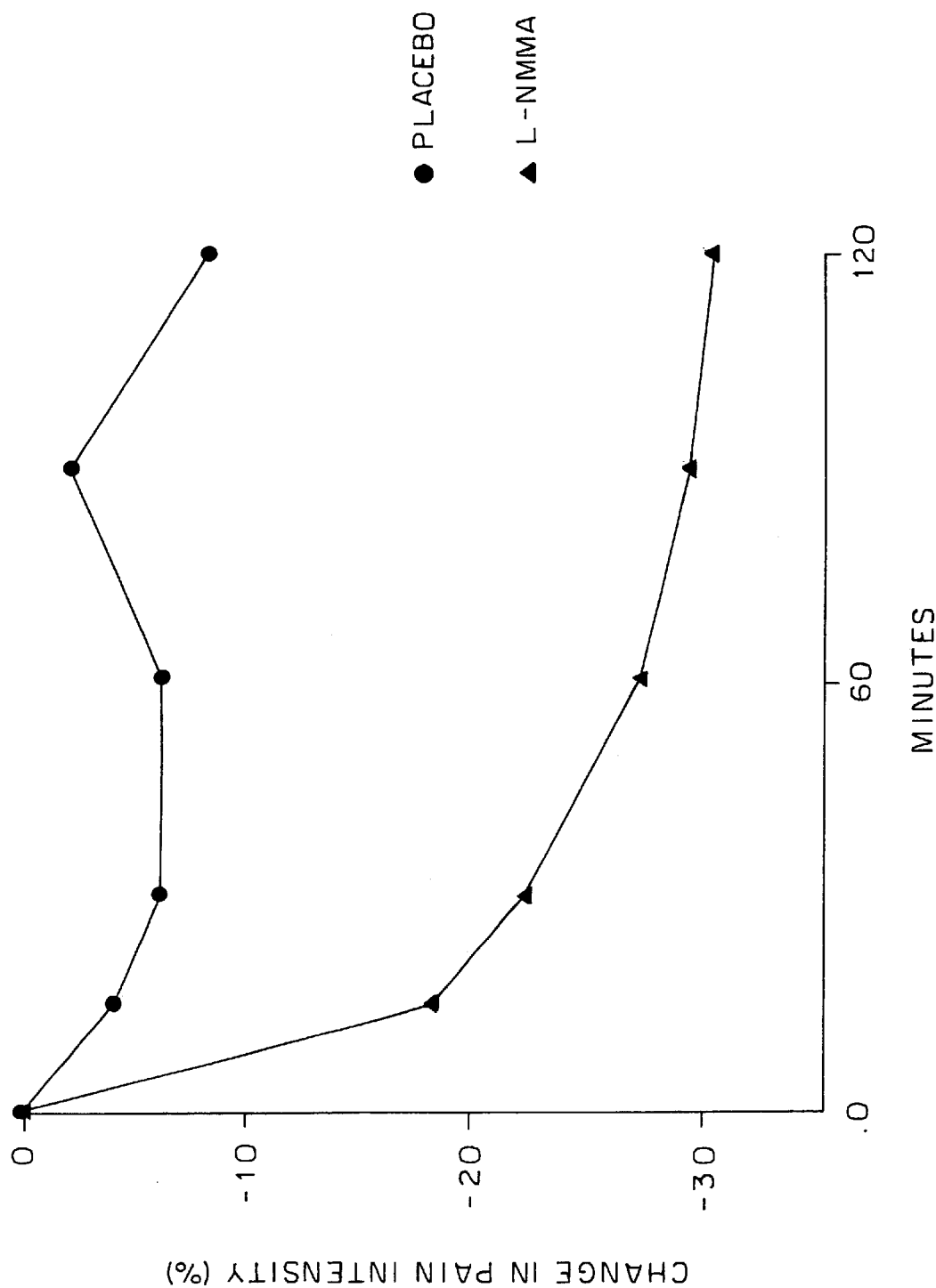

FIG. 14 shows changes in pain intensity after treatment.

Post infusion changes in pain intensity (VAS) relative to pre-treatment pain intensity in 16 patients with chronic pain. L-NMMA reduced pain significantly more than placebo ($p=0.007$).

Figure 15:
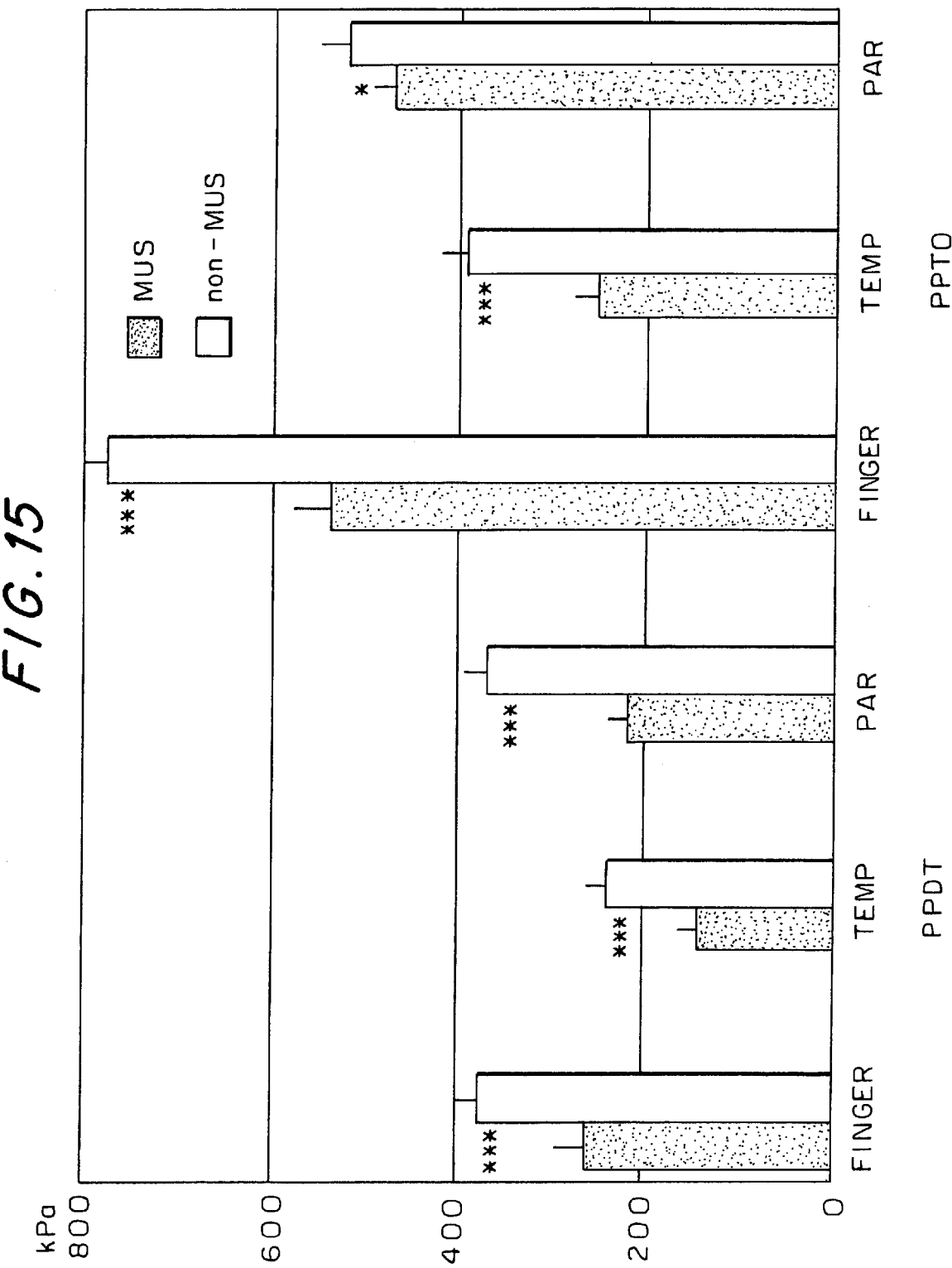

FIG. 15 shows Pressure Pain Thresholds (PPDT) and Pressure Pain Tolerances (PPTO) in patients with chronic tension-type headache associated with muscular disorders (MUS) (filled bars) or unassociated with such disorders (non-MUS) (open bars). Mean values from the fingers, temporal (Temp) and Parietal (Par) regions are given in kPa with SE as vertical bars (***indicate $p<0.001$,*indicate $p=0.04$).

Figure 16:
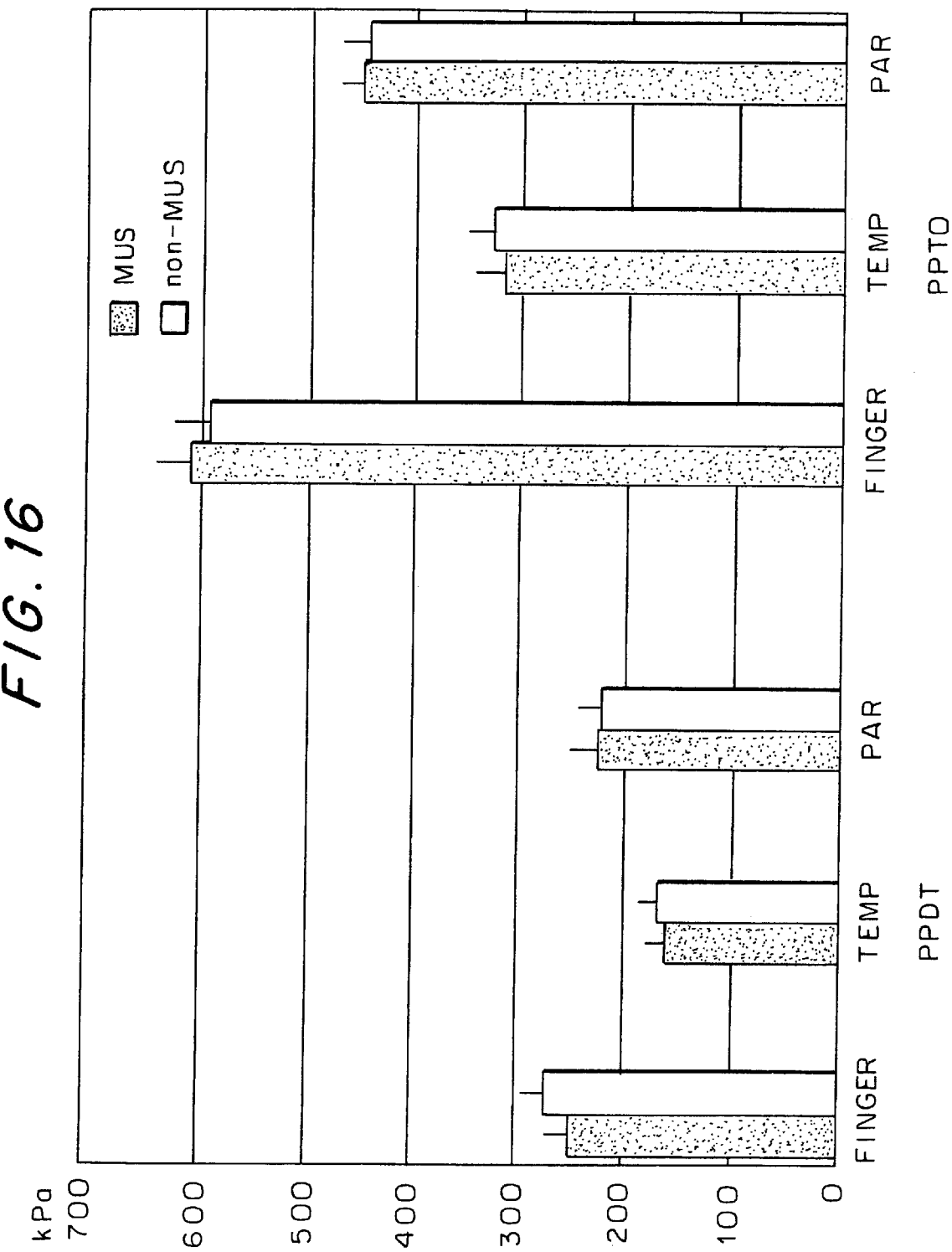

FIG. 16 shows Pressure Pain Thresholds (PPDT) and Pressure Pain Tolerances (PPTO) in patients with episodic tension-type headache associated with muscular disorders (MUS) (filled bars) or unassociated with such disorders (non-MUS) (open bars). Mean values from fingers, temporal (Temp) and Parietal (Par) regions are given in kPa with SE as vertical bars. No significant differences were detected.

Figure 17:
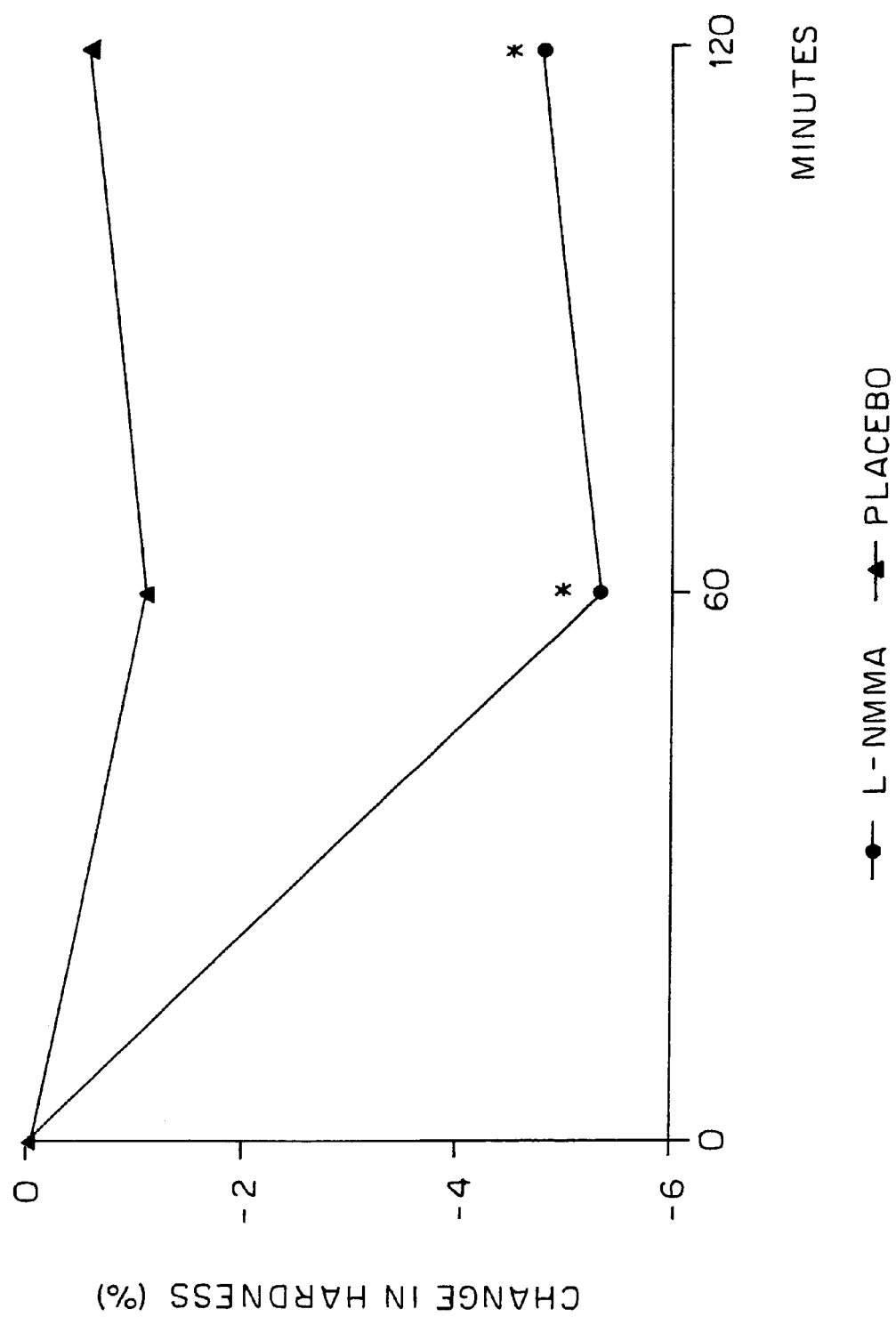

FIG. 17 shows the percentage of change in muscle hardness. Muscle hardness was significantly more reduced following treatment with L-NMMA (dots) than with placebo (triangles) in patients with chronic myofascial pain. * denotes $p<0.05$ compared with baseline (time=0). The plots represent mean scores.

Figure 18:
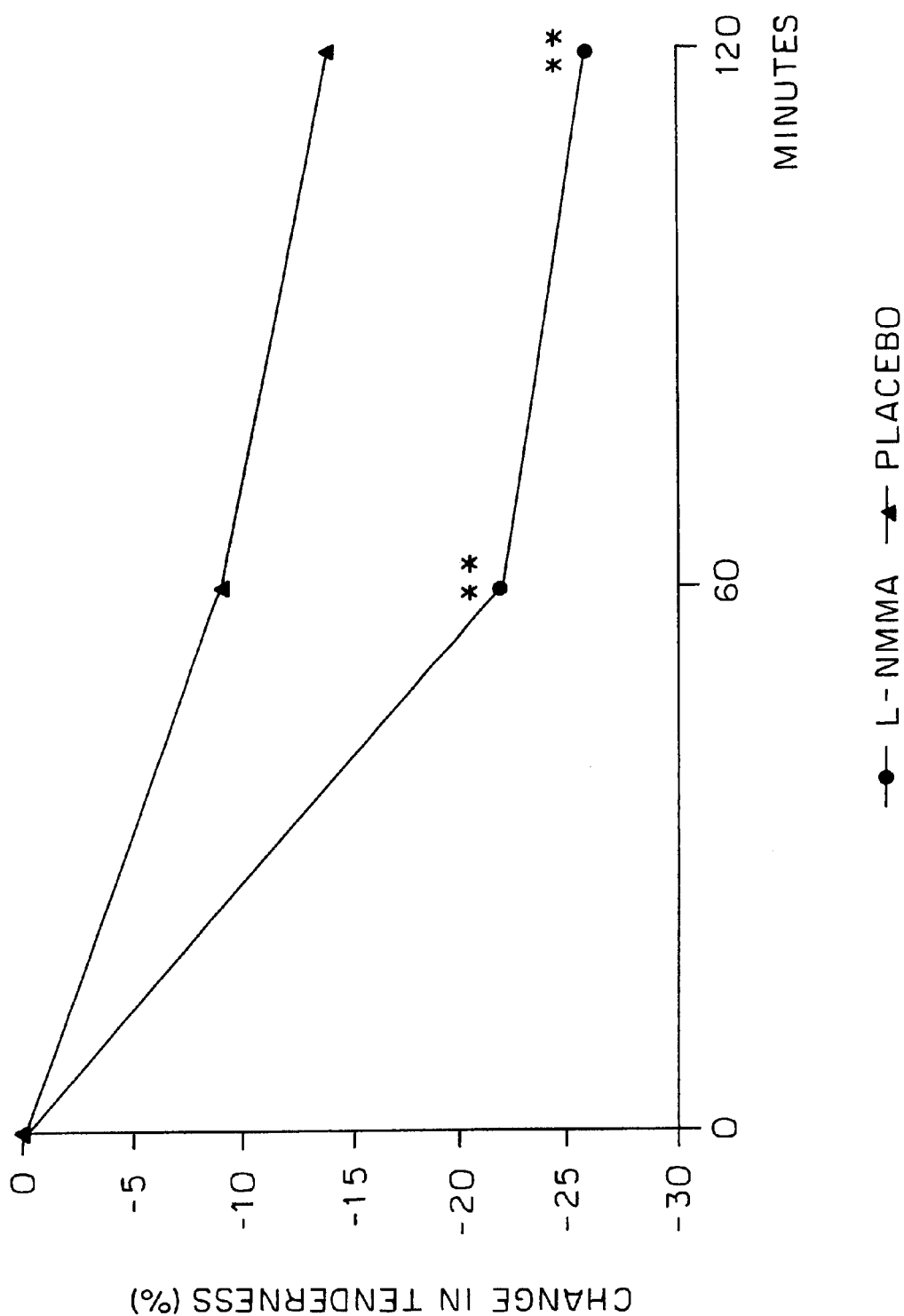

FIG. 18 shows the percentage of change in Total Tenderness Scoring (TTS). The TTS tended to be reduced following treatment with L-NMMA (dots) compared with placebo (triangles) ($p=0.11$). Within each treatment, the TTS was significantly reduced at 60 and 120 minutes after start of the infusion of L-NMMA, while there was no significant changes at any time after treatment with placebo. ** denotes $p<0.01$ compared with baseline (time=0). The plots represent mean scores.

Figure 19:
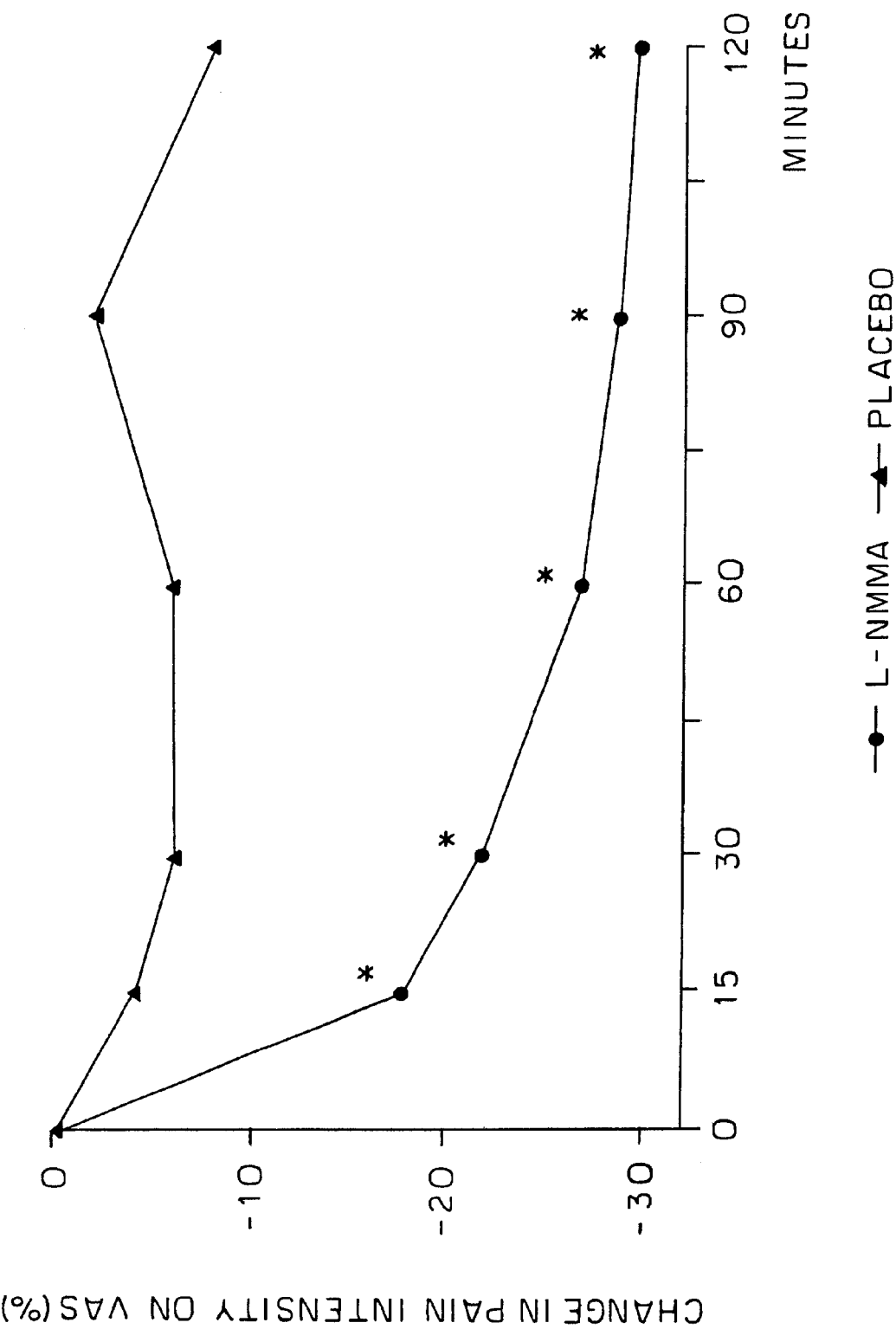

FIG. 19 shows the percentage of change from baseline pain intensity on a 100 mm Visual Analog Scale. The pain intensity was significantly more reduced during treatment with L-NMMA (dots) than with placebo (triangles) ($p=0.006$). * denotes $p<0.05$ compared with baseline (time=0). The plots represent mean scores (copyright from Lancet).

EXAMPLE 1

Experimental Evidence for Central Sensitization in Chronic Myofascial Pain

The study was performed in order to investigate the pathophysiology of myofascial tenderness, which has consistently been reported to be increased in patients with tension-type headache (Lous and Olesen 1982; Langemark and Olesen 1987, Jensen et al. 1993b). Recently, it was suggested that myofascial tenderness may be the result of a lowered pressure pain threshold, a stronger response to pressures in the noxious range (as illustrated by a steeper stimulus-response function) or a combination of both (Jensen 1990b). The aim of the study therefore was to investigate the stimulus-response function for pressure versus pain in patients with tension-type headache. The methods and the results of the study will be described in the following

Materials and Methods

TABLE III

Clinical data en hcadache patients and controls

|  | Patients | Controls |
|---|---|---|
| Number | 40 | 40 |
| Sex (females/males) | 25/15 | 25/15 |
| Age, years | 40.0 (18–60) | 39 8(18–60) |
| Freqency of TH, days/4 weeks | 24.6 (16–28) | <1 |

Patients and Controls

Forty patients with chronic tension-type headache diagnosed according to the criteria of the International Headache Society (1988) were examined during a typical episode of tension-type headache (Table III). Seven patients with coexisting infrequent migraine (<one day/month) were accepted. The patients were recruited from the out-patient headache clinic at Glostrup Hospital without respect to presence or absence, of myofascial tenderness. All patients underwent a general physical and a neurological examination and completed a diagnostic headache diary (Russell et al. 1992) during a 4-week run-in period. The patients were not allowed to take analgesics on the day of examination. Patients suffering from serious somatic or psychiatric diseases and abusers of analgesics were excluded. Forty healthy, age- and sex-matched volunteers served as controls. Only controls who did not have a headache on the day of examination and had less than 12 days With headache a year were used. All subjects gave written informed consent to participate in the study, which was approved by the local ethics committee.

Apparatus

A palpometer (Bendtsen et al. 1994) was used to investigate the stimulus-response function for pressure versus pain. The palpometer consists of a Force Sensing Resistor™ (FSR) connected to a meter, a principle first described by Atkins et al. (Atkins et al. 1992). The FSR is a commercially available polymer film device, which exhibits a decreasing electrical resistance with increasing force applied to the device. If the force is concentrated on a small area the resistance is further decreased, i.e. the properties of tile FSR lies somewhere between a force transducer and a pressure transducer. The FSR is 0.33 mm thick and circular with a diameter of 10 mm. The FSR is attached with thin adhesive tape (micropore®) to the tip of the palpating finger. The force applied to the FSR is displayed on the meter scale, which is divided into arbitrary units from 60 to 200 arbitrary units (U). To improve the readability of the meter, the readout is filtered using a low-pass filter. The relation between the forces applied to the plastic film and the palpometer output is linear in the range from 80 to 200U (Bendtsen et al. 1994). This range is equivalent to a force range from 235 gm to 1550 gm. The intra- and inter-observer variations for recordings of pressure intensity have previously found to be 3.1% and 7.2%, respectively (Bendtsen et al. 1994). Detailed information on the palpometer has been published earlier (Bendtsen et al. 1994).

Methods

The examination was performed in a standardized manner by the same investigator, a trained technician (HA), throughout the whole study. The subjects were examined sitting in a dental chair with headrest.

Total Tenderness

Tenderness of specified pericranial regions was recorded according to the Total Tenderness Scoring system, which has previously proved to be reliable (Bendtsen et al. 1995a). Five pairs of muscles (masseter, temporal, frontal, sternocleidomastoid and trapezius muscles) and three pairs of tendon insertions (coronoid and mastoid processes and neck muscle insertions) were palpated. Palpation was performed with small rotating movements of the observer's second and third fingers. Pressure was sustained for 4–5 seconds. Prior to the study, the palpometer was used to train the observer to exert a palpation pressure of moderate intensity (140 U) The tenderness was scored on a 4-point (0–3) scale as follows: 0=denial of tenderness, no visible reaction; 1=verbal report of discomfort or mild pain, no visible reaction; 2=verbal report of moderate pain, with or without visible reaction; 3=verbal report of marked pain aid visible expression of discomfort. The values from left and right sides were summed to a Total Tenderness Score (maximum possible score=48).

Stimulus-Response Functions

Stimulus-response functions for pressure versus pain were recorded during pressure-controlled palpation. i.e. palpation with controlled pressure intensity by means of the palpometer. Pressure-controlled palpation has previously proved to be a reliable method of tenderness recording (Bendtsen et al. 1995a). Palpation was performed with small rotating movements of the observer's second finger. Pressure was sustained for 4–5 seconds. The subjects were palpated at the trapezius and temporal muscles at the non-dominant side. These muscles have previously been found to represent a highly tender and a largely normal muscle respectively in patients with tension-type headache (Jensen et al. 1993b). Palpation was performed with seven different pressure intensities chosen in random order in the range from 80 to 200 U. At each pressure intensity the subject indicated the corresponding pain intensity on a visual analogue scale blinded for the observer. The visual analogue scale consisted of a 100-mm line with endpoints designated "no pain" and "unbearable pain". The degree of tenderness elicited in each subject was calculated as the area under the stimulus-response curve (AUC) according to the trapezium rule (Matthews et al. 1990).

Statistics

Results are presented as mean±SE. Data were analyzed with Mann-Whitney's test and simple linear regression. Five percent was accepted as level of significance.

Results

Total Tenderness

The Total Tenderness Score in patients was 17.7±1.7 and significantly higher than 3.4±0.53 in controls, P<0.0001.

Stimulus-Response Functions

The stimulus-response functions for pressure versus pain in the trapezius muscle in patients and in controls are shown in FIG. 2. Calculating the area under the stimulus-response functions revealed that patients were significantly more tender (AUC=3370±423 mmU) than controls (AUC= 1693±269 mmU), P=0.002. In controls, pain intensities increased in a positively accelerating fashion with increasing pressure intensities. The stimulus-response function was well described by a power function. This was demonstrated by obtaining an approximately linear relation between pressure and pain in a double logarithmic plot, slope (b)= 3.8±0.61 logmm/logU, P=0.002 (FIG. 2B). In contrast, the stimulus-response function was approximately linear in patients. b=0.50±0.04 mm/U, P=0.00004. Thus, the stimulus-response functions in controls and in patients were qualitatively different.

The stimulus-response functions for pressure versus pain in the temporal muscle are shown in FIG. 3 Patients were slightly more tender (AUC=2139±327 mmU) than controls (AUC=1722±257 mmU, but the difference was not statistically significant, P=0.42. In controls, pain intensities increased in a positively accelerating fashion with increasing pressure intensities. In a double logarithmic plot the relation between pressure and pain was linear, b=6.7±0.36 logmm/logU, P=0.00001 (FIG. 3B). In patients, pain intensities increased in a positively accelerating fashion with increasing pressure intensities. However, the curve was irregular partly resembling a linear function. The regression function was approximately linear in a double logarithmic plot b=3.0±0.36 logmm/logU, P=0.0002 (FIG. 3B).

To explore whether the abnormal stimulus-response function in the trapezius muscle was related to the increased tenderness or to the diagnosis of tension-type headache, the patients were subgrouped on the basis of their degree of tenderness. The stimulus-response functions for the 20 most tender patients (AUC=5359±538 mmU) and for the 20 least tender patients (AUC=1381±176 mmU) are shown in FIG. 4. In the 20 most tender patients, the stimulus-response function was linear, b=0.69±0.03 mm/U, P<0.00001. In contrast, pain intensities increased in a positively accelerating fashion with increasing pressure intensities in the 20 least tender patients. In a double logarithmic plot the relation between pressure and pain was linear, b=4.0±0.18 logmm/logU, P<0.00001 (because none of the patients reported any pain at the lowest stimulus intensity (U=80), a value of 1 mm was added to all pain intensities in order to perform this analysis)(FIG. 4B).

Discussion

Possible physiological mechanisms leading to myofascial pain include: a) sensitization of peripheral myofascial nociceptors, b) sensitization of second order neurons at the spinal/trigeminal level, c) sensitization of supraspinal neurons, and d) decreased antinociceptive activity from supraspinal structures. These mechanisms may be investigated by relating the intensity of mechanical pressure applied to deep tissues to the response recorded from sensor neurons. Such studies on animal models have provided important information on deep tissue pain (Ness and Gebhart 1987; Cervero and Sann 1989; Yu and Mense 1990; Janig and Koltzenburg 1991), but till now the relation between pressure and pain has not been investigated in patients with chronic myofascial pain.

Previously the stimulus-response function for pressure versus pain had been studied in 30 subjects with tender pericranial muscles (15 headache patients and 15 volunteers) (Bendtsen et al. 1995a). In the trapezius muscle, an approximately linear stimulus-response function virtually identical to the one recorded in patients in the present study was found. The finding of almost identical results in two different but comparable populations, obtained by two different observers indicates that the employed method for recording of stimulus-response functions is reliable.

Before the present investigation, the stimulus-response function in normal muscle was expected by the inventors to be qualitatively similar to the stimulus-response function in tender muscle, i.e. linear, but with a less steep slope or with a parallel shift to the right as hypothesized by Jensen (Jensen 1990). Surprisingly, the relation between palpation pressure and pain in normal muscle and in highly tender muscle differed markedly. In the trapezius and temporal muscles of controls, pain intensities increased in a positively accelerating fashion with increasing pressure intensities, a relation that was well described by a power function. The same was found in patients in the temporal muscle which was only slightly to moderately tender. The patients were subgrouped on the basis of their degree of tenderness, the stimulus-response function was linear in the most tender patients, while it was well described by a power function in the least tender patients. Thus, the stimulus-response function becomes increasingly linear with increasing degrees of tenderness and the qualitatively changed stimulus-response function is related to actual tenderness and not to the diagnosis of tension-type headache. The possibility that the linear stimulus-response function was due to a shift to the left of the normal stimulus-response function such that the patients were on the steep part of the curve already at low pressures can be excluded. If so, the patients would have been much more tender than controls also at the lowest stimulus-intensities, which was not the case.

The present finding of a qualitatively altered response to nociceptor stimulation in tender muscle demonstrates for the first time that myofascial pain has a physiological basis and that myofascial pain, at least in part, is caused by qualitative changes in the processing of sensory information. These changes may be located to peripheral nerve endings, to the spinal cord or to higher order neurons.

Spinal dorsal horn neurons that receive input from deep myofascial tissues can be classified as high-threshold mechanosensitive (HTM) neurons requiring noxious intensities of stimulation for activation and as low-threshold mechanosensitive (LTM) neurons, which are activated by innocuous stimuli (Mense 1993) Yu and Mense (Yu and Mense 1990) have shown that HTM dorsal horn neurons have a positively accelerating stimulus-response function, whereas the stimulus-response function of LTM neurons is approximately linear. This indicates that the linear stimulus-response function in tender human muscle ray be caused by activity in LTM afferents. LTM afferents do not normally mediate pain, but strong input from peripheral nociceptors can remodel the circuitry of the dorsal horn by unmasking previously ineffective synapses and by forming novel synaptic contacts between LTM afferents and dorsal horn neurons that normally receive input from HTM afferents (Wall 1977; Wall and Woolf 1984; Cervero and Janig 1992; Hu et al. 1992; Woolf et al. 1992; Mense 1993; McMahon et al. 1993; Mayer and Gebhart 1994; Hoheisel et al. 1994). In this way LTM afferents can mediate pain (Woolf and Thompson 1991), which the above-mentioned studies have been performed on animal models (Torebjörk et al. 1992). Torebjörk et al. have demonstrated similar changes in the central processing of inputs from LTM afferents in humans following intradermal injection of capsaicin. It therefore seems probable that the present findings can be explained by changes in neuronal behavior at the spinal/trigeminal level Support for this explanation was provided by a simultaneous investigation of pain thresholds in the same subjects by means of am electronic pressure algometer. Patients had significantly lower pressure pain detection and tolerance thresholds in fingers than controls (Bendtsen et al. 1996a). This indicates that the pain perception is centrally disturbed. A decrease of the supraspinal descending inhibition probably does not explain the present findings, because it has been reported that the descending inhibition acts via a parallel shift or via a decreased slope of the stimulus-response curve (Ness and Gebhart 1987; Yu and Mense 1990), while it does not change the shape of the stimulus-response curve. Sensitization of normally active peripheral nociceptors would probably induce a quantitative rather than a qualitative change of the stimulus-response curve (Koltzenburg et al. 1992).

The results thus demonstrate for the first time that nociceptive processes are qualitatively altered in patients with chronic tension-type headache, and that the central nervous system is sensitized at the spinal/trigeminal level in these patients.

Recent Studies From the Present Inventors Indicating that the Central Sensitization is Induced by Prolonged Muscle Pain As mentioned above, the information obtained from basic pain research suggests that the central sensitization in chronic tension-type headache is induced and probably maintained by prolonged noxious input from the periphery. Prolonged muscle pain is in particular, likely to induce central sensitization, because input from muscle nociceptors is more effective in inducing prolonged changes in the behavior of dorsal horn neurons than is input from cutaneous nociceptors (Wall and Woolf 1984). Recent research from the present inventors does for the first time support that there is a clear relation between central pain sensitivity and the increased muscle pain; in patients with tension-type headache, and that the increased central pain sensitivity is induced by the increased muscle pain. Thus, it has recently been demonstrated that patients with chronic tension-type headache have decreased pain thresholds to various types of stimuli both at cephalic and at extra-cephalic locations (Bendtsen et al. 1996b), indicating a state of central hypersensitivity, and that there is a significant correlation between cephalic as well as extra-cephalic pain thresholds and the total pericranial tenderness recorded by manual palpation (Bendtsen et al. 1996a). These findings demonstrate that there is a close relationship between the increased pericranial tenderness and the central hypersensitivity in chronic tension-type headache, but it does not reveal the cause and effect relationship between these abnormalities. However, since it is known that patients with episodic tension-type headache have normal pain thresholds (Jensen et al. 1993b) and that chronic tension-type headache usually evolves from the episodic form (Langemark et al. 1988), and since experimentally induced tenderness of masticatory muscles precedes the induced headache by several hours in patients with tension-type headache (Jensen and Olesen 1996), it is most likely that increased myofascial tenderness precedes central hypersensitivity.

EXAMPLE 2

Mechanisms of Spontaneous Tension-Type Headaches.

An Analysis of Tenderness, Pain Thresholds and EMG

Pericranial muscle tenderness, EMG-levels and thermal and mechanical pain thresholds were studied in 28 patients with tension-type headache and in 30 healthy controls. Each patient was studied during as well as outside a spontaneous episode of tension-type headache. Outside of headache muscle tenderness and EMG-level were significantly increased compared to values in controls subjects, while mechanical and thermal pain thresholds were largely normal. During headache muscle tenderness evaluated by blinded manual palpation increased significantly, while pressure pain thresholds remained normal and pressure pain tolerances decreased. Thermal pain detection and tolerance threshold decreased significantly in the temporal region, but remained normal in the hand. EMG-levels were unchanged during headache. The findings indicate that one of the primary sources of pain in tension-type headache may be a local and reversible sensitization of nociceptors in the pericranial muscles. In addition, a segmental central sensitization may contribute to the pain in frequent sufferers of tension-type headache. The present study, for the first time examines the same patients both during headache and outside of a headache episode with the following tests; EMG, pericranial palpation, mechanical and thermal pain thresholds. The aim was to analyze the relative importance of central and peripheral nociceptive factors.

Subjects and Methods

Subjects

Twenty eight patients, 11 males and 17 females with frequent episodic or chronic tension-type headache fulfilling the IHS-criteria (HCCIHS 1988) were included (Table IV). The patients were recruited from the out-patient headache clinic at Gentofte Hospital, Denmark. 9 patients with frequent episodic tension-type headache (EHT)$^3$ 8 days per month and 19 patients with chronic, but not daily, tension-type headache (CTH) (HCCIHS 1988) were included The reason for this selection was that patients had to have frequent headaches as well as frequent days without headache in order to be studied in both states. Further inclusion criteria were frequent headaches during at least one year and an age between 18 and 70 years. The exclusion criteria were: Daily headache, migraine more than 1 day per month, cluster headache or trigeminal neuralgia, other neurological, somatic or psychiatric disorders, concurrent ingestion of major medications including migraine prophylactics, any form of drug abuse or dependency including large amounts of plain analgesics. A diagnostic headache diary had to be filled out during a 4 week run-in period to ensure that patients fulfilled the inclusion criteria. A complete physical and neurological examination was performed before entry. Thirty age- and sex-matched healthy subjects without tension-type headache (<14 days TH/year) were used as controls (Table IV) Informed consent was obtained and the study was approved by the local ethical committee.

Methods

The patients were examined randomly during and outside a typical episode of tension-type headache. The intensity of the headache was recorded initially on a 100 mm Visual Analogue Scale (VAS), where 0 indicated no pain at all and 100 mm indicated the worst imaginable pain. Examinations were separated by at least one week and performed at the same time of the day in order to eliminate diurnal variations. Patients were not allowed to take any medication on the days of examination. Healthy controls were investigated once.

Examination

The examination was performed in a standardized fashion by the same investigators a trained technician(LH), throughout the whole study. The technician was blinded to the subjects' headache history and presence or absence of a possible muscular factor. Before measuring pain thresholds each individual was carefully instructed to apply the same interpretation of 'painful' throughout the study. Initial test sessions were applied to all subjects in order to familiarize them with the test conditions.

Palpation Method

Pericranial tenderness was evaluated by palpation of 9 pairs of muscles and tendon insertions in a standardized way. Each patient was examined by the technician and the physician in random order. Tenderness was scored at each location according to a four point scale from 0 to 3, and scores from all sites were summated. The maximally possible score was thus 54 points. This Total Tenderness Score system (TTS) has previously proved to be reliable (Bendtsen et al. 1996).

Pressure Pain Threshold

The mechanical pain thresholds and tolerances were evaluated bilaterally on the distal dorsal part of the second finger. Similarly, 2 cranial locations, one with interposed muscle, the anterior part of the temporal muscle (temp) and one without interposed muscle, the parietal region (par) were examined (Petersen et al. 1992). A standardized and previously evaluated method was applied using an electronic pressure algometer (Somedic AB, Sweden) with a 0.79 $cm^2$ circular probe (Jensen et al. 1986, Brennum et al. 1989). The Pressure Pain Detection Threshold (PPDT) was defined as the threshold, where the pressure sensation became painful, whereas the Pressure Pain Tolerance (PPTO) was the threshold where the patient would no longer tolerate the pain (Petersen et al. 1992). By pressing a hand-held button the subjects indicated that the pain threshold was reached and the pressure was immediately released. If patients did not activate the button, the experiment was terminated when reaching 800 kPa in the cranial region and 1500 kPa in the fingers. Each threshold was calculated as the median value of 3 consecutive recordings.

Thermal Thresholds

Thermal thresholds were evaluated with a computerized version of the Thermotest (Somedic AB, Sweden) (Fruhstorfer et al. 1976). The thermode consisted of series-coupled Peltier elements and measured 25×50 mm. Two locations, the thermal region of the hand and the anterior part of the temple were examined bilaterally. Three parameters were recorded in each region i.e. the Farm Detection (WD) defined as the lowest temperature detected as warm, the Heat Pain Detection (HPD) defined as the temperature where the heat sensation became painful, and the Heat Pain Tolerance (HPTO) defined as the highest temperature tolerated (Langemark et al. 1989, Jamal et al. 1985). A baseline temperature of 32° C. and a 1.0° C./sec rate of temperature change was used (Langemark et al. 1989). Heat stimulation was terminated when reaching 52° C. if the patients had not responded before. By pressing a hand-held button the subjects indicated, when the thresholds were reached. Thermode was immediately removed from the area, the exact value was recorded in the computer and the stimulator returned to baseline. Each threshold was calculated as the average of 5 determinations performed with intervals of 10–15 seconds.

Electromyography

A standardized, previously described method was used (Jensen et al. 1993a, Jensen et al. 1994). The EMG signals from the temporal and trapezius muscles were recorded bilaterally using a 4-channels electromyograph (Counterpoint, Dantec, Copenhagen). Data were collected during 2 conditions i.e. resting in the supine position in 20 one second periods interrupted by 5 second interval and during maximal voluntary contraction (MVC). The MVC lasted a maximum of 5 seconds and was repeated 5–6 times with 30 second intervals. MVC recording sessions lasting one second were analyzed and the highest value of Root Mean Square (RMS) of the EMG was selected (Jensen et al. 1993a Jensen et al. 1994). The power spectrum of each of the 1 second measurement sessions was calculated for the frequency range 0 to 1 kHz and Mean Frequency was extracted (Jensen et al. 1993a).

Statistics

Wilcoxons rank sum test (Wilc.) was used to compare paired data from headache subjects. Mann-Whitneys test (M-W) was used to compare data between controls and patients. Mean values of right and left sided observations are presented. Five per cent level or significance was used.

Results

Subjects

All the included patients and healthy controls completed the study. There were no significant differences in age and sex-distribution between healthy subjects and patients (Table IV).

Headache

The headaches examined fulfilled the diagnostic criteria for tension-type headache (HCCIHS 1988). Seventy one percent (20/28) had a bilateral headache, whereas 29%(8/28) had a unilateral headache. The median VAS score was initially 35 mm (range 17–75 mm)

Variation Between Observers

The Total Tenderness Scores(TTS) as recorded by the 2 observers (LH, RJ) at the initial examination were comparable in patients (Wilc. p=0.38) and in healthy controls (Wilc. p=0.27).

Side to Side Relation

The side to side variations were tested in patients as well as in controls, and results corresponded to previous methodological studies (Petersen et al. 1992, Jensen et al. 1986, Jamal et al. 1985, Jensen et al. 1993a).

Relation Between Controls and Patients Free of Headache

Tenderness

Median TTS in TH patients free of headache was 13 and significantly higher than 4 in healthy controls (M-W.p<$10^{-5}$) (FIG. 5).

Pressure Pain Thresholds

Pressure Pain Detection Thresholds and Pain Tolerance Thresholds in patients were not significantly different from those in healthy controls in any of the examined regions (Table V).

Thermal Thresholds

The warm detection threshold, the heat pain detection and tolerance thresholds in the hands did not differ between patients and controls. In the temporal regions of headache free patients the warm detection (WD) and heat pain-thresholds (HPD) were increased compared to healthy controls (Table VI) (M-W. W-D:p<0.001;HDP:p=0.047). The heat pain tolerances were similar in the 2 groups (Table VI).

EMG

During rest amplitude-levels were higher in patients in the headache free condition as compared to healthy controls (M-W. m.temp:p<0.001;m.trap p=0.016). No other significant differences or tendencies were detected (Table VII).

Relation to the Headache State

Tenderness

The total tenderness score increased from 13 (range 0–29) outside of headache to 16 (range 1–34) during headache (Wilc.p<0.01) (FIG. 5)

Pressure Pain Thresholds

No significant differences in pressure pain detection thresholds were found when results during headache were compared to the headache free condition. Pressure pain tolerances in the parietal regions decreased significantly during the headache (Wilc.p=0.03), whereas the pressure pain tolerances from other locations were unaffected (FIG. 6).

Thermal Thresholds

Heat pain detection (Wilc.p=0.011) and tolerances (Wilc.p=0.016) were lower in the temporal region during headache as compared to the headache free condition. No differences were seen in the land (FIG. 7).

EMG

No significant variations appeared when EMG parameters during the headache episode were compared to the headache free condition (FIG. 8 A+B).

Discussion

Comparison of Headache-Free Patients and Control Subjects

Myofascial tissue has been considered an important source of nociception in tension-type headache by some investigators (Travell et al. 1983, Drummond et al. 1987), whereas others favor alterations in central pain processing resulting in a state of hypersensitivity to incoming stimuli from myofascial and other cephalic tissues (Schoenen et al. 1991a, Schoenen et al. 1991b). Previous findings of increased cranial and peripheral sensitivity in patients with chronic tension-type headache support such central mechanisms (Langemark et al. 1989, Schoenen et al. 1991b). However, normal cranial pressure pain thresholds have recently been described in subjects with chronic tension-type headache from a general population (Jensen et al. 1993b) and in patients pith episodic tension-type headache from headache clinics (Goebel et al. 1992. Bovim et al. 1992). Comparing groups of headache patients to normal controls involves many confounding factors. These are greatly diminished in studies comparing the headache state and the non-headache state in the same individuals. The same patients mere studied both during and outside of headache. The headache mechanisms were analyzed by means of EMG, pericranial palpation, thermal and mechanical pain sensitivity.

The present study confirms that pericranial muscles of these patients outside of headache are more tender than in healthy subjects (Jensen et al. 1993, Hatch et al. 1992, Langemark et al. 1987). More importantly it is demonstrated, for the first time, that tenderness increases during the headache phase. Are these findings due to central or peripheral hypersensitivity? Normal pressure pain thresholds and pressure pain tolerances outside headache both in the cranial region and in tie hands indicates that central pain perception is not generally affected in these patients. The warm detection and heat pain detection thresholds were increased, not decreased, in the temporal region and normal in the hands. Thus, decreased sensitivity to noxious heat can be due to either a local factor in the skin which decreases the cutaneous receptor sensitivity or central factors inhibiting the incoming stimuli. No studies have addressed this issue before and the finding needs further clarification. Higher EMG-amplitude values during rest were recorded in headache free patients as compared to normal controls. These findings correspond with a recent population study where amplitude levels from the temporal and the frontal muscles were increased in subjects with chronic tension-type headache (Jensen et al. 1994). These findings indicate that the muscles are insufficiently relaxed. Whether this is causative or secondary to the headache has been much debated, but lack of correlation to the pain state(see below) indicates that it may be a secondary, characteristic. In the study presented in example 3 it is described that sustained tooth clenching may be an initiating event of tension-type headache, but the present results suggests that other mechanisms are responsible for maintaining it.

Relation to the Headache State

During headache pericranial tenderness increased, indicating peripheral or central sensitization of myofascial nociception (Jensen et al. 1990). EMG-levels were unchanged during headache which makes it unlikely that pain elicited activity in pericranial muscles can explain the increased tenderness. Pressure pain thresholds were unaffected by the headache state whereas thermal pain detection and tolerance thresholds decreased selectively in the temporal region indicating that the actual headache episode may be associated with a segmental central sensitization and/or a decreased antinociception. A more generally defective central pain modulation, as previously suggested (Schoenen et al. 1991a), is less likely, because pressure pain thresholds and tolerances in the hands were completely normal. A possible segmental disturbance at the spinal/trigeminal level may be transient and reversible since pain tolerances were normal outside of headache. The results are thus in line with the recent experimental studies by Hu et al.(Hu et al. 1992). In these important studies deep craniofacial muscle afferents were stimulated and prolonged facilitatory effects in the trigeminal nociceptive brain-stem neurons of anaesthetized rats were induced. These findings were supported by the recent findings that experimental myositis induces functional reorganization of the rat dorsal horn (Hoheisel et al. 1994). A reversible expansion of the cutaneous mechanoreceptive field was noted by Hu et al. and the spontaneous activity in cutaneous afferents was increased (Hu et al. 1992) in correspondence with previous studies (Coderre et al. 1993, Heppelmann et al. 1987). It is also known that input from deep myofascial tissue is more effective in inducing central sensitization than cutaneous input (Wall et al. 1984, Yu et al. 1993).

The decreased pain tolerances during headache in the present study may indicate a central hyperalgesia. As pain tolerances were normal outside of headache, the central changes are probably reversibly linked to the headache pain in the episodic form, whereas a more frequent activation may induce a permanent pain condition, i.e. the chronic form. The cascade of increased nociceptive activity from deep myofascial tissues may induce secondary changes such as plasticity and sensitization in the spinal dorsal horn/trigeminal nucleus (Hu et al. 1992, Hogeisel et al. 1994, Coderre et al. 1993, Heppelmann et al. 1987). The central nociceptive modulation and perception are thereby disturbed resulting in a prolonged hyperalgesia, which may persist despite disappearance of the peripheral noxious stimulus. When the central sensitization becomes sufficiently strong and widespread, the headache becomes chronic due to self perpetuating disturbances in the pain perception system.

Many of the abnormal findings in previous series of severely affected patients with chronic tension-type headache (Schoenen et al. 1991a, Langemark; et al. 1989, Schoenen et al. 1991b) may be a function of the pain rather than the initial causative factor. It can therefore be recommended to study mechanisms in patients with episodic tension-type headache. Studies comparing the pain state to the pain free state in these patients are likely to be the most informative.

TABLE IV

Clinical characteristics of ihc subjects studied

|  | TH patients | Controls |
| --- | --- | --- |
| Number (a) | 28 | 30 |
| Males | 11 | 12 |
| Females | 17 | 18 |
| Age(years) | 45(28–63) | 42(23–67) |
| Years with TH | 23(1–45) | — |
| Frequency of TH days/28 days | 20(8–27) | — |
| Frequency of migr days/year (n = 14) | 8(2–11) | — |

Mean values with range in brackets are given

TABLE V

Pressure pain thresholds in 28 headache patients free of headache and 30 healthy controls. Mean values of left and right side are given in kPa with SD in brackets.

|  | Pressure pain detection | Pressure pain tolerance |
| --- | --- | --- |
| patients HANDS | 384(161) | 139(211) |
| controls | 358(168) | 785(289) |
| patients TEMPORAL PEG. | 225(97) | 366(141) |
| controls | 203(103) | 387(157) |
| patients PARIETAL REG. | 339(172) | 560(179) |
| controls | 317(194) | 571(201) |

No significant differences between patients and controls.

TABLE VI

Thermal thresholds in 28 headache patients free of headache and 30 healthy controls. Mean values of left and right side are given in ° C. with SD in brackets.

|  | Warm Detection | Pain threshold | Pain tolerance |
| --- | --- | --- | --- |
| patients HANDS | 34.3 (3.1) | 42.3 (3.1) | 47.0 (2.2) |
| controls | 34.4 (1.2) | 42.4 (2.7) | 47.5 (2.2) |
| patients TEMP | ***34.7 (1.6) | *40.1 (2.8) | 44.1 (2.0) |
| controls | 33.8 (0.8) | 39.1 (2.7) | 43.9 (8.5) |

*p < 0.05
**p < 0.001
(Mann-Whitney's test)

TABLE VII

EMG levels in 28 patients free of headache and in 30 healthy controls. REST indicate resting conditions and MVC indicate n,aximal voluntary contraction. Mean values of left and right side are given with SD in brackets.

|  | REST | | MVC | |
| --- | --- | --- | --- | --- |
|  | RMS (uV) | Mean F (Hz) | RMS (uV) | Mean F (Hz) |
| TEMPORAL MUSCLES | | | | |
| patients | **3.1 (2.4) | 81 (25) | 164 (66) | 173 (28) |
| controls | 2.3 (0.9) | 74 (17) | 181 (101) | 155 (30) |
| TRAPEZIUS MUSCLES | | | | |
| patients | *3.6 (1.2) | 40 (10) | 260 (141) | 88 (18) |
| controls | 3.1 (0.9) | 41 (9) | 259 (131) | 88 (16) |

*p < 0.05
**p < 0.01
(Mann-Whitney's test)

EXAMPLE 3

Initiating Mechanisms of Experimentally Induced Tension-Type Headache

To elucidate possible myofascial mechanisms of tension-type headache, the effect of 30 minutes of sustained tooth clenching (10% of maxim-al EMG-signal) was studied in 58 patients with tension-type headache and in 30 age and sex matched controls. Pericranial tenderness, mechanical and thermal pain detection and tolerance thresholds and EMG levels were recorded before and after the clenching procedure. Within 24 hours 69% of patients and 17% of controls developed a tension-type headache. Shortly after clenching, tenderness was increased in the group who subsequently developed headache, whereas tenderness was stable in the group of patients who remained headache free. Mechanical pain thresholds evaluated by pressure algometry remained unchanged in the group which developed headache, whereas thresholds increased in the group which did not develop headache Thermal pain detection and tolerance thresholds remained unchanged in both groups. These findings indicate that, although there may be several different mechanisms of tension-type headache, one of them is sustained muscle contraction. A peripheral mechanism of tension-type headache is therefore possible, whereas a secondary segmental central sensitization seems to be involved in subjects with frequent tension-type headache. Finally, the increase in pressure pain thresholds in patients who did not develop headache suggest that clenching activated their antinociceptive system whereas those developing headache were unable to do so.

Introduction

Tension-type headache is extremely prevalent (Rasmussen et al. 1991) and represents a major health problem (Rasmussen et al. 1992). Nevertheless, its pathogenic mechanisms are largely unknown (Pikoff et al. 1984, Olesen et al. 1991). Sustained involuntary muscle contraction has been suggested as an important source of pain in tension-type headache (Travel et al. 1983). In recent years, central mechanisms have however, been favoured (Schoenen et al. 1991a). Substantial evidence for any of the suggested pathogenetic mechanisms has not yet been available. To study the initiating mechanisms of headache it is valuable to induce it. The time necessary to reach the laboratory makes it impossible to study the initial phase of spontaneous attacks. Furthermore, using a known stimulus to induce headache makes it easier to analyze its mechanisms. Experimental tooth clenching has previously induced mild headaches in migraineurs (Jensen et al. 1985) but has never been studied in subjects with tension-type headache. In the present study tension-type headache was induced by sustained muscle contraction in patients and controls and studied the pre- and post-contraction phase by means of EMG, thermal and pressure pain thresholds as well as headache and tenderness scoring.

Subjects and Methods

Subject

Fifty-eight patients with frequent episodic or chronic tension-type headache fulfilling the IHS-criteria (HCCIHS 1988) were included (Table VIII) Twenty eight patients had frequent episodic tension-type headache $^3$8 days with headache per month and 30 patients had chronic, but not daily, tension-type headache (HCCIHS 1988). The reason for His selection was that patients had to have frequent headaches as well as days without headache in order to be studied in the latter state. Further inclusion criteria were duration of frequent tension-Type headache in at least one year and age between 18 and 70 years. The exclusion criteria were: daily headache, migraine more than 1 day per month, cluster headache, trigeminal neuralgia, other neurological, systemic or psychiatric disorders, ingestion of major medications including migraine prophylactics, any form of drug abuse or dependency as daily ergotamine or large amounts of plain analgesics. The patients were recruited from the outpatient headache clinic at Gentofte Hospital and complete physical and neurological examinations were done before entry. Thirty healthy age- and sex matched subjects (headache<14 days/year) were used as controls (Table VIII). Informed consent was obtained and the study was approved by the local ethical committee.

Procedure

All patients had to fill in a diagnostic headache diary during a 4 week run-in period to ensue that patients fulfilled the inclusion criteria. All subjects, patients and controls, were told to fill out a special diary for at least 24 hours after the study. Patients were examined when free of headache and were not allowed to have taken any analgesics on the day of examination. The EMG-parameters and pain characteristics were recorded twice on the day of examination, immediately before and after the clenching procedure. A 100 mm Visual Analogue Scale (VAS), where 0 mm was no pain at all and 100 nun was the worst imaginable pain was used. Recordings of pain intensity were made before, 30, 60 and 90 minutes after the clenching procedure in the laboratory, as well as after 4, 6, and 24 hours after the clenching in the diary. All subjects were informed that the purpose of the study was to measure variations in muscle tension and pain characteristics during tooth clenching. They were not informed of the risk of developing headache in order to avoid bias.

Examination

The examination was performed in a standardized way by the same person, trained technician, throughout the whole study. The study was blinded as the technician was unaware of the subjects headache history. Before recordings of pain thresholds each individual was carefully instructed to apply the same interpretation of 'painful' throughout the study. Initial test sessions were applied to all subjects in order to familiarize them with the test conditions.

Palpation

Pericranial tenderness was evaluated by palpation of 9 pairs of muscles and tendon insertions by the technician and the physician in a standardized, randomized procedure. Tenderness was scored in each location according to an ordinal scale from 0 to 3 and scores from all sites were summated. The maximum possible score was thus 54 points. This Total Tenderness Score system (TTS) has previous proved to be reliable (Bendtsen et al. 1995).

Pressure Pain Thresholds

The pressure pain thresholds were evaluated bilaterally on the distal dorsal part of the second finger, and in two cranial locations, one with interposed temporal muscle (Temp) and one without interposed muscle, the parietal region (Par). A standardized and previously evaluated method was applied using an electronic pressure algometer (Somedic AB, Sweden) with an 0.79 cm$^2$ circular stimulation probe (Petersen et al. 1992, Jensen et al. 1986. Brennum et al. 1989). Two pain qualities were recorded, the Pressure Pain Detection Threshold (PPDT) defined as the threshold, where the pressure sensation became painful, and the Pressure Pain Tolerance (PPTO) defined as the threshold where the patient would no longer tolerate the pain (Petersen et al. 1992). By pressing a hand held button the subjects indicated that the threshold was reached, and the pressure was released immediately. If patients did not activate the button, the experiment was terminated when reaching 800 kPa in the cranial region and 1500 kPa in the fingers. Each threshold was calculated as the median value of 3 determinations performed with intervals of 10–15 seconds.

Thermal Pain Thresholds

Thermal thresholds were evaluated with a computerized version of the Thermotest (Somedic AB, Sweden) (Fruhstorfer et al. 1976). The thermode consisted of series-coupled Peltier elements and measured 25×50 mm. The thenar region of the hand and the anterior part of the temporal region were examined bilaterally. Three stimulation qualities were recorded; the Warm Detection limit (WD) defined as the lowest temperature detected as warm, the Heat Pain Detection (HPD) defined as the temperature where the heat sensation became painful, and the Heat Pain Tolerance (HPTO) defined as the highest temperature tolerated (Jamal et al. 1985). A baseline temperature of 32° C. and a 1.0° C./sec rate of temperature change was used. Heat stimulation was terminated when reaching 52° C., if the patients had not responded before. By pressing a hand-held button the subjects indicated when the actual threshold was reached. This value was recorded automatically and the stimulator returned to baseline. Each threshold was calculated as the average of 5 determinations performed with intervals of 10–15 seconds.

Electromyography

EMG signals from the temporal and trapezius muscles were recorded bilaterally by a 4-channels electromyograph (Counterpoint, Dantec, Copenhagen)(Jensen et al. 1993a). A standardized, previously described method where the temporal and frontal muscles were investigated were applied (Jensen et al. 1993a). Data were collected during rest in the supine position and during maximal voluntary contractions (MVC) (Jensen et al. 1993a). The RMS voltage was measured. Power spectrum was calculated for the frequency range 0 to 1 kHz and Mean Frequencies (Mean F) were extracted (Jensen et al. 1993a).

Provocation

After tile initial recording series the subjects were instructed to clench their molar teeth and the EMG activist from the temporal muscles was recorded. The subjects were instructed to clench their teeth at 10% of their individual MVC value and to keep this value constant for 30 minutes. The subjects received visual feed back from the EMG-monitor, and were allowed 3 short (<60 sec) rests during the session. Force was not measured.

Statistics

The chi square test was used to test differences in headache characteristics between patients and controls. The sign test was used to compare the frequency of provoked headache with the expected frequency. Wilcoxon's rank sum test (Wilc.) was used for comparing paired data within subjects, and Mann-Whitney's test (M-W.) was used for comparing unpaired data between patients and controls. Five per cent level of significance was used.

Results

All the included patients and healthy controls completed the study. No significant variation in age- and sex distribution between patients and controls appeared (Table VIII). Only two left handed subjects (1 patient, 1 control) were included. Therefore no correction for band dominance was made.

Development of Headache

In total, 69% (40/58) of the patients and 17% (5/30) of the healthy controls developed headache within 24 hours after tooth clenching. The frequency of headache among patients was significantly higher than expected from their usual headache frequency (p=0.016) and higher than in healthy controls (p<0.0001). Twenty-eight percent of patients (16/53) and 7% of controls (2/30) developed headache within the first hour after tooth clenching. The median duration from clenching to development of headache was 1.5 hours in patients (range 0.5–20 hours) and 1.5 hours (range 0.5–6 hours) in controls. All headaches, in patients as well as in controls, fulfilled the diagnostic criteria for tension-type headache (n=7). The headaches were bilaterally located in 85% (34/40) of the patients and in all controls. It was of pressing quality in all subjects. It was not aggravated by physical activity in 85% (34/40) of the patients and in all the controls. No associated symptoms such as nausea, photophobia or phonophobia were reported. Initially, the headache was very mild in both groups, but the intensity increased during the following hours in patients (FIG. 9). Four and 24 hours after clenching those patients who had developed headache had significantly higher mean VAS-scores than those few healthy controls who had developed headache (M-W. p=0.02) (FIG. 9). In patients, the median headache duration was 8 hours (range 1–24 hours) but not significantly different from 3 hours (range 2–24 hours)(M-W. p=0.10) in the small number of controls (n=5) with headache.

Variation Between Observers

The Total Tenderness Scores (TTS) recorded by the 2 observers at the initial examination did not differ significantly within patients (Wilc. p=0.24) nor in healthy controls (Wilc. p=0.2).

Variation Between Left and Right Sided Observations

The side to side variations were tested in patients as well as in controls, and results corresponded to previous methodological studies Petersen et al. 1992, Fruhstorfer et al. 1976, Jensen et al. 1993a, Jensen et al. 1993b) For simplicity mean values of left and right sided observations arc presented in the following.

Relation Between Measurements in Patients and Controls Before Clenching

Tenderness

Initial median TTS in patients was 12 (range 0–29) and significantly higher than the median score of 4 (range 0–10) in healthy controls (M-W.$p<10^{-7}$)

Pressure Pain Thresholds

Pressure Pain Detection Thresholds were increased in the temporal regions of headache patients compared with healthy controls (M-W.p=0.03) (Table IX). No significant variations or tendencies were found in the other locations (M-W.fingers p=0.98; parietal p=0.21)(Table IX).

Pressure Pain Tolerances in patients were not significantly different from those in healthy controls in any of the examined regions (M-W.fingers p=0.87; temp. p=0.45; parietal p=0.69) (Table IX).

Thermal Thresholds

The warm detection threshold was higher in the temporal regions in patients than in healthy controls M-W. p=0.02), while the warm detection in the hands was normal (M-W. p=0.26)(Table X). The heat pain detection and tolerance thresholds were normal in both locations (Table X).

EMG

During rest the EMG-amplitude was significantly increased in the trapezius muscle of patients compared to controls (M-W.

Trap p=0.04). A similar but not quite significant increase was seen in the temporal muscles (M-W.Temp p=0.10)

(Table XI). Frequency values during rest as well as all EMG values during MVC were not different from those of controls (Table XI).

Effect of Clenching on the Measured Tests

Tenderness

The median initial TTS was 12 (range 0–28) in patients who developed headache and was increased significantly to 14 (range 0–33) at the recording 90 minutes after clenching (Wilc.p<0.001) (FIG. 10). The median TTS in patients who remained headache free was also 12 (range 0–24) and remained 12 (range 0–33) after clenching (Wilc. p=0.83). A marked, but not quite significant increase in TTS from 6 to 10 was seen in the few control subjects who developed headache (Wilc p=0.06), whereas TTS only increased from 4 to 5 in controls who remained headache free (Wilc.p=0.0015)(FIG. 10).

Pressure Pain Thresholds

Pressure Pain Detection Thresholds in fingers and in the temporal regions remained constant in those subjects (patients as well as controls) who developed headache, whereas a significant increase of pain detection thresholds was seen in subjects who did not develop headache (Wilc. Patients fingers p=0.01; temp p=0.024; Controls fingers p=0.04; temp p=0.01)(FIG. 11A).

Pressure Pain Tolerance decreased in the parietal region in patients who developed headache after clenching (Wilc.p=0.009), whereas the tolerances remained stable in patients who remained headache free. Pressure Pain Tolerances in the same region increased in controls who remained headache free after stimulation (Wilc.p=0.003)(FIG. 11B). Pressure Pain Tolerance was stable in the hand and the temporal region in all subjects without regard to headache development (FIG. 11B).

Thermal Thresholds

In patients as well as in controls, no significant differences in thermal thresholds were seen between those, who developed headache and those who did not (FIG. 12).

EMG

During resting condition a significant decrease in amplitude value was seen in the temporal and the trapezius muscles after clenching both in patients (Wilc. Temp. p<0.001, Trap. p<0.01) and in controls (Wilc. Temp.p<0.001, Trap. p<0.01). This decrease was similar in those who developed headache and in those who did not (FIG. 13A). In contrast, only the group of patients who developed headache showed decreased amplitude values in the temporal muscle during MVC (Wilc. p=0.011) (FIG. 13B).

Discussion

Studies in a general population and in specialized headache clinics have revealed that increased muscle tenderness and frequent tooth clenching are consistent findings in subjects with tension-type headache (Jensen et al. 1993b, Jensen et al. in prep., Wanmann et al. 1986, Langemark et al. 1987, Lous et al. 1982). Whether these relations are causal or secondary to the pain has not yet been clarified. However, if there is a causal connection it should be possible to create an experimental headache model by interfering with these systems. Although several attempts to make experimental pain in the chewing muscles have been made (Christensen et a. 1981, Clark et al. 1991, Bakke et al. 1989), only few studies have focused specifically on headache (Jensen et al. 1985, Magnusson et al. 1984). Jensen et al. reported that 54% of 48 migraineurs developed a muscle-contraction like headache after shortlasting sustained clenching (Jensen et al. 1985). These findings indicate that headache subjects in general are more susceptible to develop headache after sustained muscle contraction.

Relation Between Measurements in Patients and Controls Before Clenching

Tenderness

The finding of increased muscle tenderness by manual palpation as the most significant difference between headache patients and healthy controls supports previous findings in a general population (Jensen et al. 1993b). When selecting psycho-physiological measures it is important to consider the information carried by the particular measure. Local tenderness as recorded by manual palpation is assumed to indicate increased nociception from the free nerve endings in the connective tissue of muscles, fascia and tendons (Jensen et al. 1990, Torebjork et al. 1984). Such increased nociception is probably due to a sensitization of nociceptors by bradykinin, prostaglandines, substance P. 5-HT, histamine and potassiu (Mense et al. 1992, Jensen et al. 1992). Reduced muscle blood flow leading to ischemia has been suggested as the cause of tenderness (Myers et al. 1983), but recently normal blood flow in the temporal muscles of patients with chronic tension-type headache has been demonstrated (Langemark et al. 1990).

Pressure Pain Thresholds

A decreased pressure pain detection threshold indicates a state of allodynia, i.e. pain elicited by stimuli which normally are non-noxious. A decrease in pressure pain tolerance threshold indicates a state of hyperalgesia, i.e. increased sensitivity for supra threshold noxious stimuli which may and may not coexist with allodynia (Jensen et al. 1990). Identification of allodynia and hyperalgesia may therefore be of special interest in the study of central and peripheral mechanisms of nociception. In addition, we have studied responses from the hands and the cranial regions in order to determine a possible anatomical variation in the response to pain stimulation. We also wanted to study the muscular contribution and recorded thresholds from two neighboring cranial regions one with and one without interposed muscle. The fact that pressure pain detection thresholds and tolerances were lower in the temporal region than in the nearby parietal region indicates that myofascial nociception contributes considerably to the recorded responses. However, the finding of largely normal thresholds and tolerances in headache free patients indicates that the general pain sensitivity in the cranial region is not permanently disturbed as previously suggested (Schoen et al. 1991a, Langemark et al. 1989).

Thermal Thresholds

Thermal warm detection represents the activity in unmyelinated C-fibers (Campbell et al. 1989) whereas the heat pain detection represents activation of cutaneous C-fibers responsive to mechanical and heat stimuli and their central modulation (Campbell et al. 1989). In addition, the myelinated A mechano heat fibers type I may be activated when the heat pain tolerance is tested. If central pain perception is increased, decreased warmth and heat pain thresholds are expected. However, thermal pain detection and tolerances were normal in the headache patients suggesting normal pain sensitivity as discussed above. The present findings differ from a previous finding of decreased heat pain detection thresholds in patients with chronic tension-type headache (Langemark et al. 1989). In the prior study patients were, however, more severely affected and most of them had daily headaches and long lasting drug overuse (Langemark et al. 1989). It is likely that chronic pain may induce central sensitization to incoming nociceptive signals, and the previously described decrease in noxious thresholds in severely affected headache patients may, therefor, be an effect of chronic pain rather than its cause.

EMG

It has been a widely held view that tension-type headache is caused by involuntary contraction of cranial muscles. The slightly increased amplitude values during rest indicate that the pericranial muscles are insufficiently relaxed (Jensen et al. 1994). However, this increase in EMG level was unaffected by the presence or absence of headache, and is therefore not likely to be a primary cause of pain (Jensen et al. 1994). The decreased amplitude values during maximal voluntary contraction in patients developing headache and not in controls indicate that in some other way a muscular factor may be involved (Jensen et al. 1994).

Effect of Clenching on Headache and the Measured Tests

The present results indicate that sustained muscle contraction can induce headache although the recordings have not been repeated during a similar placebo provocation. An important finding is the increased tenderness in subjects who developed headache. Headache had not developed in the majority of subjects at 90 minutes after provocation, when the increased tenderness was recorded. This suggests that clenching causes tenderness, that tenderness precedes headache and that tenderness may be one of the causes of the subsequent headache. A similar increase in tenderness scores during spontaneous attacks of tension-type headache has recently been shown (Jensen et al. in press). Muscle tenderness usually requires several hours to develop (Christensen et al. 1981). A further increase in tenderness would therefore probably have been detected if we had continued to record tenderness several hours after clenching. In the present study, the experimental headache occurred with a lag time of one to several hours. In addition, the pain was mild initially and gradually, in the course of hours, reached its peak. In contrast, the intensity of headache in control subjects did not increase after onset. The very low VAS-score in controls may represent discomfort rather than clinical relevant pain as reported by the patients. This indicates that the antinociceptive system may be deficient in headache patients. The exact degree of clenching seems to be of minor importance. Approximately the same percentage of subjects developed headache with 10% of maximal contraction in the present study and with 5% or 30% of maximal contraction in the previous migraine study (Jensen et al. 1985).

Mechanisms of Tension-Type Headache Suggested by the Present Results

The pressure pain detection thresholds remained stable in patients who developed headache but increased in subjects who did not develop headache. We also found decreased pain tolerances in patients who developed headache, unchanged values in the remaining patients and increased values in controls, suggesting that headache patients do not activate their antinociceptive system or that it is less effective in these patients (Le Bars et al. 1979). On the other hand, their central antinociceptive suppression is not so permanently and severely affected that it is reflected in permanent hyperalgesia, since the noxious thresholds and tolerances were normal outside of a headache episode. In addition, as the thermal thresholds remained unaffected of the headache state, no evidence for a general hypersensitivity to pain was found. The similar decreases in EMG-levels in both groups after clenching indicate that the increased EMG-levels in patients free of headache may be a secondary characteristic. This is supported by similar findings in a recent study of patients during and outside of spontaneous tension-type headache attacks (Jensen et al. in press). Based on the present findings, results from previous studies (Jensen et al. 1993b, Jensen et al. 1994, Jensen et al. in press) and results from recent animal studies (Mense et al. 1993, Le Bars et al. 1919) on peripheral and central pain mechanisms we suggest the following mechanism of tension-type headache: involuntary contraction of muscles, due to mechanical or psychological stress, causes activation and chemical sensitization of the myofascial mechano receptors and their afferent fibers. This increased peripheral input may result in sensitization and functional reorganization of second order sensory neurons in the dorsal horn (Hoheisel et al. 1994) as stimuli in the deep myofascial tissues are much more effective, in this respect than stimuli in the cutaneous tissues (Wall et al. 1984, Yu et al. 1993). Normally, increased peripheral nociceptive input is counteracted by increased activity in the antinociceptive system and no headache arises. However, in some individuals and under certain circumstances this homeostatic mechanism does not function. An abnormal sensitization arises and combined with an impaired central antinociceptive mechanism, an episode of tension-type headache may develop. However, the relative importance of peripheral and central sensitization and of the antinociceptive system remain further elucidation. In conclusion, the results obtained be the present inventors suggest that muscular factors play an important role in the initiation of a headache episode. However, the further development and transition into the chronic pain state is probably due to a central sensitization with or without impairment of the central antinociceptive system.

TABLE VIII

Clinical characteristics of the subjects studied

|  | TH patients | Controls |
| --- | --- | --- |
| Number (n) | 58 | 30 |
| Males | 22 | 12 |
| Females | 36 | 18 |
| Age(years) | 45(21–63) | 42(23–67) |
| Years with TH | 23(1–45) | — |
| Frequency of TH days/28 days | 17(8–27) | — |
| Frequency of migraine days/year (n = 28) | 7(2–12) | — |

Mean values with range in brackets are given. TH indicates tension-type headache

TABLE IX

Pressure pain detection thresholds (PPDT) and tolerances (PPTO) in 58 headache patients free of headache and 30 healthy controls. Mean values of left and right side with SD in braclets are given in kPa.

|  | PPDT | PPTO |
|---|---|---|
| FINGER | | |
| patients | 353(137) | 779(294) |
| controls | 358(165) | 785(289) |
| TEMPORAL REGION | | |
| patients | *220(76) | 399(146) |
| controls | 203(103) | 387(157) |
| PARTETAL REGION | | |
| patients | 323(146) | 600(190) |
| controls | 317(195) | 571(201) |

*$p<0.05$

TABLE X

Thermal thresholds in 58 headache patients free of headache and in 30 healthy controls. Mean values of left and right side with SD in brackets are given in °C.

|  | Warm detection | Pain threshold | Pain tolerance |
|---|---|---|---|
| HANDS | | | |
| patients | 34.5 (1.2) | 42.3 (3.0) | 47.2 (2.3) |
| controls | 34.4 (1.2) | 42.4 (2.7) | 47.5 (2.2) |
| TEMPORAL REGION | | | |
| patients | *34.2 (1.7) | 39.6 (2.7) | 44.0 (2.0) |
| controls | 33.8 (0.8) | 39.1 (2.7) | 43.9 (2.9) |

*$p < 0.05$

TABLE XI

EMG levels in 58 patients free of headache and in 30 healthy controls during rest and maximal voluntary contraction(MVC). Mean values of left and right side with SD in brackets are given; RMS indicate root mean square values of amplitudes (uV) and Mean F indicate mean frequency (Hz).

|  | REST | | MVC | |
|---|---|---|---|---|
|  | RMS | Mean F | RMS | Mean F |
| TEMPORAL MUSCLES | | | | |
| patients | 2.7 (1.9) | 78 (22) | 164 (81) | 164 (32) |
| controls | 2.3 (0.9) | 74 (17) | 181 (101) | 155 (30) |
| TRAPEZIUS MUSCLES | | | | |
| patients | *3.5 (1.2) | 39 (9) | 246 (124) | 88 (16) |
| controls | 3.1 (0.9) | 40 (9) | 259 (131) | 88 (16) |

*$p < 0.05$

EXAMPLE 4

A Nitric Oxide Synthase Inhibitor is Effective in Chronic Tension-Type Headache and is Counteracting Central Sensitization

Introduction

Nitric oxide (NO) is an almost ubiquitous molecule that probably plays an important role in the modulation and transmission of pain (Meller and Gebhart 1993). NO is assumed to be of particular importance for the development of central sensitization, i.e. increased excitability of neurons in the central nervous system (McMahon et al. 1993; Meller and Gebhart 1993). In this way NO may contribute to the development of chronic pair. The synthesis of NO is catalyzed by the enzyme NO synthase (NOS) (Moncada et al. 1991). Recent animal studies have shown that NOS inhibitors reduce central sensitization in persistent pain models (Haley et al. 1992; Hao and Xu 1996; Mao et al. 1997). Chronic tension-type headache responds poorly to analgesics and new treatments are badly needed (Rasmussen et al. 1991). The aim of the present study was to evaluate whether intravenous infusion of the NOS inhibitor, L-N$^G$ methyl arginine hydrochloride (L-NMMA), is effective in the treatment of this disorder.

Materials and Methods

Subjects

Sixteen patients With a diagnosis of chronic tension-type headache according to the criteria of the International Headache Society, (headache Classification Committee 1988) were recruited from the out-patient headache clinic at Glostrup Hospital. There were 12 women and 4 men with a mean age (range) of 38.5 (23–52) years. Five patients with coexisting infrequent migraine (£ one day/month) were accepted. All patients completed a diagnostic headache diary during a 4-week run-in period (Russell et al. 1992). At screening, a full physical and neurological examination, including 12-lead ECG were carried out. Blood samples for routine haematological and biochemical testing, and urine sample for urine analysis were taken. The patients were not allowed to take analgesics 12 hours prior to the treatment. Exclusion criteria were: daily medication (including prophylactic headache therapy but not oral contraceptives); pregnant or breast feeding women; abuse of analgesics (corresponding to>2 gm of aspirin/day) or alcohol, serious somatic or psychiatric diseases including depression (Hamilton Depression Score $^3$17 (Hamilton 1960)); ischemic heart disease; a supine diastolic blood pressure >90 mmHg or heart rate <50 beats per minute at study entry. All patients gave written informed consent to participate in the study, which was approved by The local ethics committee and conducted in accordance with the Declaration of Helsinki.

Procedures

Using a double-blind crossover design, the patients were randomized to receive 6 mg/kg L-NMMA (Clinalfa, Switzerland) or placebo (isotone glucose) on two days with a typical episode of tension-type headache separated by at least one week. Randomization (Med.Stat) and drug preparation were performed by staff not involved in the study. The medication was given over 15 minutes into an antecubital vein (Braun Perfusor). The following parameters were measured at baseline and 15, 30, 60 and 120 minutes post administration: headache intensity on a 100-mm Visual Analog Scale (VAS) (0-no headache and 100-worst imaginable headache) and on a Verbal Rating Scale (VRS) from 0–10 (0-no headache; 5-moderate headache; 10-worst imaginable headache). Blood pressure and pulse rate were measured 5 minutes prior to administration of treatment and at 5, 10, 15, 20, 25, 30, 60, 90 and 120 minutes post administration. Twelve-lead ECG was monitored continuously. Any adverse events were recorded. Patient with unrelieved headache at 120 minutes post treatment were allowed to take rescue medication. All patients were asked to record details of the following on a diary card at 4, 8, 12, 16, 20 and 24 hours post administration, headache intensity on VRS, any medication taken and adverse events. Between 4–7 days after each treatment, the patients returned to the clinic, the diary cards were collected and any adverse events were noted.

Data Analysis and Statistics

Primary endpoint was the reduction of pain intensity over time on active treatment compared to placebo. The secondary endpoints were reduction of pain intensity at 30, 60, 90 and 120 minutes post dosing on VAS and VRS compared to pre-treatment pain score within each treatment. Comparison of pain intensity on VAS, blood pressure and pulse rate over time between treatments were performed With ANOVA. Paired-Samples T Test was used to compare pre-treatment pain score on VAS with pain score at 30, 60, 90, 120 minutes post dosing within each treatment. The sum of differences between the pre-treatment VRS score and the VRS score at 30, 60, 90, 120 minutes post dosing was calculated in order to obtained a summary measure of pain score for each treatment (Matthews et al. 1990). These sums of differences for each treatment were compared by Wilcoxon Signed Rank test. Five percent was accepted as level of significance.

Results

Treatment Efficacy

L-NMMA reduced pain intensity (VAS) over time significantly more than placebo (p=0.007). Relative per cent changes in pain intensity from baseline are shown in FIG. 14. Pain score was significantly reduced after 30, 60, 90 and 120 minutes post treatment with L-NMMA (Table XII). There was no significant reduction in pain intensity following treatment with placebo at any time points. The pain intensity on VRS was significantly lower after treatment with L-NMMA than after treatment with placebo (p=0.02).

Adverse Events and Rescue Medication

The mean arterial blood pressure (MAP) and pulse rate changed significantly over time during treatment with L-NMMA compared with placebo (p=0.0001 and p=0.0001). The maximum increase in MAP was 12±2% and occurred 15 minutes post dosing. The maximum decrease in pulse rate was 16±2% and occurred 10 minutes post dosing. The increase in MAP and decrease in pulse rate are consistent with known pharmacological properties of L-NMMA. Patients were unaffected by these changes. Seven patients reported subjective symptoms in relation to the L-NMMA infusion These were: tiredness (2), dryness of the mouth (3), drowsiness (1), exhaustion (1), nausea (1) and a feeling of tingling in arm (1). Four patients reported subjective symptoms in relation to placebo treatment. These were: a feeling of tingling in arm (2) and shoulder (2), dryness of the mouth (1), warm sensation in the body (1) and drowsiness (1). No patients withdrew from the study because of side effects. Three patients treated with L-NMMA and 7 patients treated with placebo used simple analgesics as rescue medication.

Discussion

There is ample experimental evidence showing that persistent activity in peripheral nociceptors may lead to sensitization of spinal dorsal horn neurons partly via activation of N-methyl-D-aspartate (NMDA) receptors (Coderre et al. 1993). Since many of the effects of the NOVA receptor activation are mediated through production of NO, it seems probable that NO plays an important role in the hyperalgesia in the spinal cord (Meller and Gebhart 1993). In support for this, animal models have shown that NOS inhibitors reduce spinal dorsal horn sensitization induced by continues painful input from the periphery (Haley et al. 1992; Hao and Xu 1996; Roche et al. 1996). However, the efficacy NOS inhibitors have not previously been examined in patients.

Recently, it has been demonstrated that spinal dorsal horn sensitization due to prolonged nociceptive input from pericranial myofascial tissues probably plays an important role in the pathophysiology of chronic tension-type headache (Bendtsen et al. 1996a, 1996b; Jensen et al. 1997). Thus, it is likely that the analgesic effect of L-NMMA in chronic tension-type headache is due to reduction of central sensitization at the level of the spinal dorsal horn.

In conclusion, the present study provides the first evidence of an effect of NOS inhibitors in human chronic pain, and indicates that the effect of NO is via reduction of central sensitization probably at the level of the dorsal horn/trigeminal nucleus,

TABLE XII

Pain scores on VAS before treatment and at 30, 60, 90 and 120 minutes post dosing. Mean values (SD) are given.

| | Baseline | 30 minutes | 60 minutes | 90 minutes | 120 minutes |
|---|---|---|---|---|---|
| L-NMMA | 49 ± 16 | 38 ± 18* | 35 ± 18* | 34 ± 21* | 33 ± 21* |
| Placebo | 44 ± 14 | 41 ± 17$^{NS}$ | 40 ± 17$^{NS}$ | 42 ± 16$^{NS}$ | 40 ± 17$^{NS}$ |

*$p < 0.05$ and NS = not significant compared with pretreatment values (Paired-Samples T Test).

EXAMPLE 5

Muscular Factored are of Importance in Tension-Type Headache

Introduction

A recent study from by the present inventors demonstrated for the first time that chronic tension-type headache has a physiological basis and is caused at least partly by qualitative changes in the central processing of sensory information (Bendtsen et al, 1996b). It was suggested that muscular disorders are of primary importance for the development of central sensitization. To test this hypothesis, the present study of the psychophysical tests suggested in the IHS classification (Headache Classification 1988) as well as thermal pain sensitivity was conducted. The primary aim was to compare the mechanical and the thermal pain sensitivity in tension-type headache patients with and without disorders of pericranial muscles. The secondary aim was to study the clinical characteristics of those patients.

Patients and Methods

Patients

Fifty-eight patients with tension-type headache fulfilling the IHS-criteria (Headache Classification 1988) were included (Table XIII). Twenty-nine patients had frequent episodic tension-type headache (ETH) and 29 patients had chronic tension-type headache (CTH). The patients were recruited from the out-patient headache clinic at Gentofte Hospital and complete physical and neurological examinations were done before entry. According to the primary aim patients with restricted tenderness in the pericranial muscles were favoured, since the percentage of patients associated with muscular disorders is 80–90% in consecutive populations (Jensen et al., 1996, Langemark et al., 1988). Further inclusion criteria were duration of tension-type headache for at least one year and age between 18 and 70 years. The exclusion criteria were: migraine more than 1 day per month, cluster headache, trigeminal neuralgia, other neurological, systemic or psychiatric disorders, ingestion of major medications including prophylactics for migraine or other headaches, any form of drug abuse or dependency as daily ergotamine or large amounts of plain analgesics.

Thirty healthy subjects (12 males and 18 females) with a mean age of 42 years (range 23–67 years) and without tension-type headache (<14 days tension-type headache/year) were used as controls. Informed consent was obtained and the study was approved by the local ethical committee. The present study was a part of a multifaceted study of tension-type headache, of which other parts have been published previously (Jensen, 1996, Jensen and Olesen, 1996).

Procedure

All patients had to fill in a diagnostic headache diary during a 4 week run-in period to ensure that they fulfilled the inclusion criteria. Patients were instructed to fulfill the diary at the end of each day with headache and to record the mean intensity on a 0–3 scale, where 0 was no pain and 3 was severe incapacitating pain that requires bed rest (Russel et al., 1992). The approximate start and disappearance of headache and the total intake of analgesics or other medications should also be recorded. A standard dose of analgesics was defined as a dose equivalent to 1000 mg of aspirin All patients were examined When free of headache and were not allowed to have taken any analgesics on the day of examination.

Examination

The examination was performed in a standardized way, which has been described previously (Jensen, 1996, Jensen and Olesen, 1996). All recordings were performed by the same observer, the technician, throughout the entire study and the observer was blinded for the following subdivision of patients. Before recordings of pain thresholds each individual was carefully instructed to apply the same interpretation of 'painful' throughout the study. Initial test sessions were applied to all subjects in order to familiarize them with the test conditions, Palpation Pericranial tenderness was evaluated by palpation of 9 pairs of pericranial muscles and tendon insertions by the technician in a standardized randomized procedure (Langemark and Olesen, 1989, Jensen et al., 1993b, Bendtsen et al., 1995a). Tenderness was scored in each location according to an ordinal scale from 0 to 3, and scores from all sites were summated. The maximum possible score was thus 54 points. This Total Tenderness Score system(TTS) (Langemark and Olesen, 1987) has previously proved to be reliable (Bendtsen et al., 1995). We have previously demonstrated that the most ideal cut-off point for separating tension-type headache subjects from non-headache subjects with respect to muscle tenderness was the 75% quartile of TTS obtained from a general population, whereas pressure algometry and EMG provided no further information (Jensen et al., 1996). In the following, TTS is used as the only criteria for further subdivision patients with TTS above 9 (equal to the 75% quartile of TTS from healthy controls) was classified as having an association with muscular disorder (MUS), whereas those with TTS value at 9 or below were classified as unassociated with such a disorder (non-MUS).

Pressure Pain Thresholds

The pressure pain thresholds were evaluated bilaterally on the distal dorsal part of the second finger, and in two cranial locations, one with interposed temporal muscle(Temp) and one Without interposed muscle in the parietal region (Par). A standardized and previously evaluated method was applied using an electronic pressure algometer (Somedic AB, Sweden) with an 0.79 $cm^2$ circular stimulation probe (Petersen et al., 1992, Jensen et al., 1986, Brennum et al., 1989). Two pain qualities were recorded, the Pressure Pain Detection Threshold (PPDT) defined as the threshold, where the pressure sensation became painful, and the Pressure Pain Tolerance (PPTO) defined as the threshold where the patient would no longer tolerate the pain (Petersen et al., 1992). By pressing a hand held button the subjects indicated that the threshold was reached, and the pressure was released immediately. If patients did not activate the button, the experiment was terminated when reaching 800 kPa in the cranial region and 1500 kPa in the fingers. Each threshold was calculated as the median value of 3 determination performed with intervals of 10–15 seconds, and mean values of left and right sided recordings are presented in the following.

Thermal Pain Thresholds

Thermal thresholds were evaluated with a computerized version of the Thermotest (Somedic AB, Sweden) (Fruhstorfer et al., 1976, Yanrnitsky et al., 1995). The thermode consisted of series-coupled Peltier elements and measured 25×50 mm. The thenar region of the hand and the anterior part of the temporal region were examined bilaterally. Three stimulation qualities were recorded; the Warm Detection limit (WD) defined as the lowest temperature detected as warm, the Heat Pain Detection (HPD) defined as the temperature where the heat sensation became painful, and the Heat Pain Tolerance (HPTO) defined as the highest temperature tolerated (Jensen et al., 1996, Jensen and Olesen, 1996). A baseline temperature of 32° C. and a 1.0° C./sec rate of temperature change was used. Heat stimulation was terminated when recording 52° C., if the patients had not responded before. By pressing a hand-held button the subjects indicated when the actual threshold was reached. This value was recorded automatically and the stimulator returned to baseline. Each threshold was calculated as the average of 5 determinations performed with intervals of 10–15 seconds, and mean values of left and right sided recordings are presented in the following.

Electromyography

EMG signals from the temporal and trapezius muscles were recorded bilaterally by a 4-channels electromyograph (Counterpoint, Dantec, Copenhagen). A standardized, previously described method was applied (Jensen et al., 1993). Data were collected during rest in the supine position and during maximal voluntary contractions (MVC) (Jensen et al., 1996). The root mean square (RMS) voltage was measured, Power spectrum was calculated for the frequency range 0 to 1 kHz and Mean Frequencies (Mean F) were extracted (Jensen et al., 1996).

Statistics

Clinical data are presented as mean values with range (Table XIII and XIV) and the psychophysical data as mean values±SE. Mann-Whitney's U test was used for testing unpaired observations in patients with and without association with muscular disorders. Analysis of variance was used to control for the variations in sex distribution among the groups. Spearman's test was used for calculation of coefficients of correlation. Five percent was accepted as level of significance.

Results

Two patients (a male with the episodic and a male with the chronic subform) were excluded from the present study due to deficient diaries. The remaining 56 patients, 28 with CTH and 28 with ETH completed the study and detailed clinical data with respect to their association with muscular disorder are presented in Table XIII and Table XIV. Fourteen patients with chronic tension-type headache had a history of coexisting migraine with a mean value of 7.3 days with migraine per year, not significantly different from the 15 ETH patients, who had a history of 7.7 days with migraine per year. Similarly, there was no significant difference between the prevalence of migraine in patients with muscular disorders compared to those without such disorder. No significant variations in the clinical characteristics between patients with and without disorders of pericranial muscles could be detected (Table XIII, XIV).

Tenderness Recorded by Manual Palpation

According to the prior definition of association with muscular disorders, CTH patients associated with muscular disorder (MUS) had, as expected, significantly higher TTS at 18.5 compared to 6.2 in those without such an association (non-MUS)(<0.0001). Similarly, ETH patients with MUS had significantly higher TTS at 15.3 compared to 4.3 in those without such an association ($p<0.0001$).

Pressure Pain Thresholds

Pressure pain detection and tolerance thresholds were significantly lower in CTH patients associated with MUS compared to non-MUS patients in all the examined locations (PPDT $p<0.001$; PPTO $p<0.05$) (Table XV) (FIG. 15).

In patients with ETH, there were no significant differences in the pressure pain thresholds and tolerances between subjects with or without association with muscular disorders in any of the examined locations (Table XVI) (FIG. 16).

Thermal Pain Thresholds

There were no significant differences in heat detection, heat pain and heat pain tolerance thresholds from the hands and the temporal regions between CTH patients with and without a muscular disorder. Similarly, no significant variations in thermal thresholds could be detected in ETH patients with and without a muscular disorder.

Relation Between Tenderness and Pain Thresholds

In CTH patients, the Total Tenderness Score (TTS) was highly correlated to the mechanical pain thresholds at the temporal region (Temp: TTS vs PPDT:r=0.61, $p<0.001$; TTS vs PPTO:r=0.65, $p<0.001$), and a similar tendency was seen at the parietal region (TTS vs PPDT r=0.59, $p=0.003$; TTS vs PPTO r=0.24, $p=0.27$) and at the extracephalic region (Hands: TTS vs PPDT r=0.36. $p=0.06$, TTS vs PPTO, r=0.48, $p=0.02$). No such relations could be detected in ETH patients in any of the examined locations. When TTS was correlated to thermal thresholds no significant relations appeared either in the chronic or the episodic form.

EMG

When EMG levels were recorded from the temporal and the trapezius muscles under resting conditions and during maximal voluntary contraction, CTH patients with association to muscular factors had significantly higher RMS values in their trapezius muscles during resting condition compared to non-MUS patients ($p=0.02$). No other significant differences between the 2 subgroups in neither CTH nor ETH patients appeared.

Relation to Healthy Controls

Tenderness by Manual Palpation

The mean Total Tenderness Score(TTS) in the 30 healthy controls was 4.7 (quartiles 0–9) and was significantly lower than 9.8 (quartiles 4–15) in those 28 patients with ETH ($p=0.002$). In CTH patients TTS was 14.1 (quartiles 4–15) and significantly higher than in ETH patients ($p=0.03$) and in healthy controls ($p<0.0001$).

Pressure Pain Thresholds

Compared to healthy controls, CTH patients with non-MUS had significantly higher pressure pain thresholds and tolerance thresholds in all the examined locations ($p<0.01$), whereas the mechanical tolerances tended to be significant lower in CTH patients with MUS (fingers PPTO, $p=0.07$; Temp PPTO $p=0.05$). No significant differences could be detected in the parietal regions or in pressure pain detection thresholds from the other locations. When pressure pain detection and tolerance thresholds from the 2 subgroups of ETH patients were compared to those from healthy controls no significant differences appeared.

Thermal Pain Thresholds

When the thermal thresholds were compared to healthy controls, significantly higher values of all the tested qualities were noted in cephalic locations in those 10 CTH patients without association with muscular disorders, whereas only warm detection values were higher on the hands of these patients (Temporal:WD $p=0.02$, WPDT $p=0.04$,WPTO $p=0.028$; Hands:WD $p=0.02$). No significant variations in thermal thresholds could otherwise be detected in relation to healthy controls.

EMG

Only CTH patients associated with muscular factors had significantly higher RMS values in the temporal ($p=0.008$) and the trapezius muscles during rest ($p=0.004$) than healthy controls. No other differences between patients and controls were noted.

Discussion

Relation Between Tenderness and Pain Thresholds

In the present study highly significant inverse correlations between TTS, pressure pain detection and tolerance thresholds were found in patients with CTH corresponding with our recent study (Bendtsen et al, 1996). Others have reported relatively small and clinically insignificant relations (Schoenen et al. 1991a, Jensen et al, 1996, Sandrini et al., 1994), and the pressure pain thresholds provided only limited diagnostic value (Jensen et al., 1996). This discrepancy may be due to the fact that the pressure pain threshold represents the lower end, and the pressure pain tolerance the upper end of a pain stimulus response curve. Tenderness obtained by manual palpation elicit pain intensities between these extremes where the difference between patients and controls is largest as discussed recently it Bendtsen et al (Bendtsen et al., 1996b, Bendtsen et al., 1996c). The diagnostic tests given in the IHS classification were previously assessed in a study from a highly specialized headache clinic (Snadrini et al., 1994) and in subjects from a general population (Jensen et al., 1996). In the latter study, 87% of subjects with chronic, and 66% of subjects with episodic tension-type headache had a disorder of the pericranial muscles (Jensen et al., 1996). In the former, Sandrini et al reported that 61% of patients with episodic, and 66% of patients with chronic tension-type headache had disorder of pericranial muscles. An earlier study, where only EMG and pressure algometry were assessed, 72% were found to be associated with disorders of pericranial muscles (Schoenen et al., 1991). Tenderness determined by manual palpation was previously found to be the most sensitive and specific test for disorder of pericranial muscles (Jensen et al., 1996) and was therefore applied as the only test to separate the 2 subforms in the present study.

Pathophysiological Mechanisms of the Disorders of Pericranial Muscles

It has been uncertain whether the increased, pericranial myofascial tenderness was the cause or the effect of the pain. A recent experimental study indicated, however, that tenderness precedes the induced headache by several hours when tension-type headache is induced by tooth clenching (Jensen et al., 1996). Possible mechanisms for the tenderness include 1) sensitization of peripheral myofascial nociceptors; 2) sensitization of second order neurons at the spinal/trigeminal level; 3) impaired central modulation of the nociceptive activity. As tension-type headache is a disease in man and not known in animals, experimental animal models are of limited value for evaluation of these mechanisms. Fortunately, quantitative analysis of mechanical and thermal pain thresholds in humans can be used for this purpose. Thermal pain- and tolerance thresholds are normal in most of these patients, which indicates that pain mediated by C-fibers is registered and modulated normally. The present finding of markedly increased tenderness, slightly decreased mechanical but normal thermal thresholds at cephalic and extracephalic locations in CTH patients associated with muscular disorder, strongly indicates a hyperalgesic response to mechanical stimulation in these patients in line with previous studies (Bendtsen et al., 1196c, Schoenen et al., 1991b, Langemark et al., 1999). This is also supported by our findings of a highly significant inverse relation between tenderness and mechanical threshold. It has recently been demonstrated that due to central sensitization, pain in CTH and in fibromyalgia may be mediated via low-threshold mechanosensitive afferents projecting to dorsal horn neurons (Bendtsen et al., 1996c, Bendtsen et al. in press). This is supported by prior observations by Bendtsen et al., where an abnormal qualitative stimulus response function was found only in those 20 CTH patients with the most pronounced tenderness whereas 20 patients without abnormal tenderness exhibited a fairly normal stimulus response curve (Bendtsen et al., 1996c). A further support for myofascial involvement is the finding of increased EMG amplitude levels only from the pericranial muscles of CTH patients associated with muscular disorders, whereas EMG levels otherwise were similar to those in controls. The mechanisms of pain in tension-type headache without association with a muscular disorder cannot be explained by simple allodynia and/or hyperalgesia as both mechanical and thermal pain thresholds from these patients were significantly increased compared to healthy controls, indicating a higher pain tolerability. Therefore, other mechanisms, probably in the central modulation of pain, must be considered. As the clinical features examined in the present study were fairly similar between the 2 subgroups in both the episodic and the chronic form it is very likely, however, that several pathophysiological mechanisms are shared and further documentation about the fairly rare patients with tension-type headache without association with muscular disorders are highly needed. Taken together our data strongly suggest that central sensitization is of key importance in chronic tension-type headache with disorders of pericranial muscles, whereas other mechanisms must be considered in patients without such disorders.

Relationship Between Episodic and Chronic Tension-Type Headache

The present study is the first study which have examined this wide variety of clinical characteristics and psychophysical tests in both episodic and chronic tension-type headache. A marked difference in nociceptive mechanical thresholds between the 2 subgroups in the chronic, but not in the episodic form was demonstrated, whereas tenderness recorded by manual palpation was highly increased in both the episodic and the chronic tension-type headache. A hypothesis of the pathophysiological evolution of tension-type headache can therefore be created. In ETH patients with disorder of pericranial muscles, the most likely mechanism is a slightly increased input from myofascial nociceptors projecting to a widely normal central pain perception system. As chronic tension-type usually evolves from the episodic form (Langemark et al., 1989) it is suggested that prolonged painful input from the periphery may sensitize the central nervous system and that the pain in CTH associated with muscular disorder thus may be due to a central misinterpretation of the incoming signals at the dorsal horn or trigeminal level. Such mechanisms have been demonstrated in animal models (Coderre et al., 1993, Mense et al., 1993, Hu et al., 1992, Hoheisel et al., 1994), and irritative stimuli from myofascial, deep tissues are found to be much more effective for induction of central sensitization than cutaneous stimuli (Yu et al., 1993). Muscular disorders may therefore be of major importance for the conversion of episodic into chronic tension-type headache. As the most frequently reported precipitating factors leading to tension-type headache are stress, mental tension and tiredness (Rasmussen et al., 1993, Clark et al., 1995. Ulrich et al., 1996), central supraspinal involvement is undoubtedly also involved, although precipitating factors may be different from causative factors. Whether the precipitating factors and the evolution of pain vary between the patients with and with disorders of pericranial muscles remains to be elucidated.

In conclusion, the present data indicate that the fine balance between peripheral nociceptive input and their central modulation seems to be disturbed in the majority of patients with tension-type headache, namely those associated with muscular disorders. An a central misinterpretation of the incoming peripheral stimuli may be the result, a vicious circle is started and is probably maintained long time after the primary clinching stimuli/stressor had stopped. Disorders of pericranial muscles may therefore be of major importance for the conversion of episodic into chronic tension-type headache, whereas other mechanisms should be considered for those patients without such disorders. The present study supplements the understanding of the interaction between peripheral and central changes in tension-type headache, and thereby, hopefully, will lead to a better understanding, prevention and treatment of the most prevalent type of headache.

TABLE XIII

Clinical characteristics of patients with chronic tension-type headache (N = 28)

|  | Patients with MUS | Patients without MUS |
| --- | --- | --- |
| Number (n) | 18 | 10 |
| Males/females | 7/11 | 7/3 |
| Age(years) | 48.1 (34–64) | 49.4 (37-59) |
| Years-with TH | 24.8 (1–45) | 26.2 (2–50) |
| Frequency of TH (days/28 days) | 22.6 (15–28) | 23.7 (15-28) |
| Intensity (0–3 scale) | 1.7 (1–2.5) | 1.4 (1-2) |
| Duration (hours) | 11.3 (4.2-24) | 9.5 (2.9-24) |
| Medication (doses/day) | 1.6 (0-3.1) | 1.8 (0-4.1) |

Mean values with range in brackets are given. MUS indicate association with muscular disorder as defined in the text, and without MUS indicate no such association. TH indicates tension-type headache.

TABLE XIV

Clinical characteristics of patients with episodic tension-type headache (N = 28)

|  | Patients with MUS | Patients without MUS |
| --- | --- | --- |
| Number (n) | 14 | 14 |
| Males/females | 1/13 | 5/9 |
| Age(years) | 39.8 (20–56) | 42.6 (21–59) |
| Years with TH | 20.2 (2–40) | 19.6 (8–30) |
| Frequency (days/28 days) | 9.6 (5–14) | 10.0 (6–14) |
| Intensity (0–3 scale) | 1.7 (1.0–2.1) | 1.8 (1.4–2.2) |
| Duration (hours) | 9.7 (4.7–18) | 8.6 (3.3–24) |
| Medication (doses/day) | 1.0 (0–2) | 0.8 (0–1.4) |

Mean values with range in brackets are given. MUS indicate association with muscular disorder as defined in the text, and without MUS indicate no such association. TH indicates tension-type headache.

TABLE XV

Pressure pain detection and tolerance thresholds in patients with chronic tension-type headache (N = 28). Mean values are given in kPa with SE in brackets.

|  | Patients with MUS (n = 18) | Patients without MUS (n = 10) | p-value |
| --- | --- | --- | --- |
| Pain detection thresholds |  |  |  |
| Fingers | 262 (17) | 374 (23) | p < 0.001 |
| Temporal region | 143 (9) | 241 (18) | p < 0.0001 |
| Parietal region | 217 (18) | 368 (28) | p < 0.001 |
| Pain tolerance thresholds |  |  |  |
| Fingers | 535 (32) | 776 (50) | p < 0.001 |
| Temporal region | 252 (17) | 394 (23) | p < 0.0001 |
| Parietal region | 471 (38) | 521 (27) | p = 0.04 |

TABLE XVI

Pressure pain detection and tolerance thresholds in patients with episodic tension-type headache (N = 28). Mean values are given in kPa with SE in brackets.

|  | Patients with MUS (n = 14) | Patients without MUS (n = 14) | p-value |
| --- | --- | --- | --- |
| Pain detection thresholds |  |  |  |
| Fingers | 247 (12) | 269 (18) | p = 0.14 |
| Temporal region | 162 (10) | 169 (10) | p = 0.72 |
| Parietal region | 223 (16) | 221 (16) | p = 0.89 |
| Pain tolerance thresholds |  |  |  |
| Fingers | 610 (34) | 595 (50) | p = 0.47 |
| Temporal region | 317 (18) | 327 (23) | p = 0.98 |
| Parietal region | 453 (23) | 449 (30) | p = 0.85 |

EXAMPLE 6

Gabapentin has a Prophylactic Effect in Chronic Tension-Type Headache

Introduction

GABA is an important inhibitory transmitter in the central nervous system and it has been suggested that the encoding of low-threshold mechanical threshold stimuli depends upon the presence of a tonic activation of intrinsic glycine and/or GABAergic neurons (Yaksh and Malmberg 1994). Gabapentin was synthesized to be a systemically active GABA analogue and was found to have anticonvulsant effect. Although initially employed in humans to control seizures, recent clinical cases indicated that the agent showed efficacy in treating human neuropathic pain states (Rosner et al 1996), and a considerably effect in several experimental pain models (Hwang and Yaksh 1996, Xiao and Bennett 1996). The exact mechanism is not fully understood, but several Mechanisms have been suggested. Binding studies fail to show affinity for either GABA A or GABA B, although Gabapentin can increase the rate of GABA synthesis and release. Furthermore, Gabapentin showed binding affinity to the alpha-2-subunit of a calcium channel (Gee et al. 1996), and these calcium channels are recently reported to play a very exciting role in the genetic studies of migraine disorders. As the side effect profile of Gabapentin is favorable, the prophylactic effect of Gabapentin in a small open labeled pilot study in patients with chronic tension-type headache was evaluated.

Materials and Methods

Three patients with a diagnosis of chronic tension-type headache according to the International Headache society (Headache Classification Committee 1988) were recruited from the outpatient headache clinic at Glostrup Hospital. The patients were males with a mean age of 42 years (range. 35–49). The mean life time duration of chronic tension-type headache was 16 years (range 7–21). Two patients had a coexisting but infrequent migraine. Exclusion criteria were: daily major medication (including prophylactic headache therapy); abuse of analgesics or alcohol; serious somatic or psychiatric diseases including depression.

Procedures

Using an open labeled design, patients fulfilled a diagnostic headache diary during at least 4 weeks run-in period to ensure the diagnostic criteria. Thereafter, the patients received Gabapentin (Neurontin®) tablets, initially 300 mg (one tablet) per day on day one, increasing with 300 mg (1 tablet) per day to 900 mg (3 tablets) on day 3. The treatment period lasted 4% weeks, and during this period patients were asked to continue with headache diaries, and record headache intensity, frequency, duration, any medication taken and any possible adverse events. At a follow, up visit at day 29–32, diaries were collected and any adverse events and evaluation of the treatment were recorded. Duo to the low number of patients, no statistical analysis were done. The primary efficacy parameters were headache intensity frequency and duration, and the mean values from the run-in period were compared to those obtained during the treatment period, Results All patients completed the study. Headache intensity decreased 35%, namely from 5.5 on a 0–10 VAS intensity scale during run-in period to 3.6 during active treatment. Duration of the individual headache episode was reduced by 8%, and frequency of headache decreased by 45%, namely from 23.5 days per 4 weeks during run-in period to 13 days per 4 weeks during the active treatment period. The mean daily intake of analgesics decreased by 72% from 1.1 dose per day to 0.3 dose per day. One patient had excellent effect of Gabapentin with complete relief of the headache after 2 days treatment, another patient had a moderate effect on headache intensity and frequency, and the third patient had no significant effect on any of efficacy parameters. Those two subjects with good or excellent effect reported no side effects, whereas the third patient who had no beneficial effect of Gabapentin complained of sedation, vertigo and slight nausea. These side effects disappeared completely after cessation of the drug intake.

Discussion and Conclusion

The present results suggest a positive prophylactic effect of Gabapentin in chronic tension-type headache, which is in accordance with the predictions made from the model involving central sensitization provided by the present invention. Although the exact mechanism of action of gabapentin is not fully elucidated, the preliminary experimental evidence are highly in favor of a pathophysiological explanation of chronic tension-type headache, as caused by central sensitization,

EXAMPLE 7

Dextromethorphan has a Prophylactic Effect in Chronic Tension-Type Headache

Introduction

The common role played by NMDA antagonism in preclinical models is consistent with the observation that systemic ketamine reduces the allodynia, hyperalgesia and after sensation present in patients with peripheral pain injury, and the magnitude of the relief is, in general, proportional to dose. Dextromethorphan has been shown to reduce the after sensation induced by repetitive stimuli in human volunteers (Price et al 1994). Furthermore, the NMDA receptors are shown to act on the neuronal excitability via opening or closing of ion channels. The increase in intracellular calcium by such opening of the ion channels is believed to initiate a cascade of biochemical events, including pain. Effective blockade of these events is possible by NMDA antagonists, which are also highly effective in various human pain conditions related to central sensitization (Persson et al 1995). The major problem In this treatment strategy is, however, the central side effects of most NMDA antagonists. Dextromethorphan has been known for decades as a cough suppressant and has a very favorable side effect profile. Therefore the prophylactic effect of Dextromethorphan was evaluated in a small, open labeled pilot study in patients with chronic tension-type headache.

Materials and Methods

Five patients with a diagnosis of chronic tension-type headache according to the International Headache Society (Headache Classification Committee 1988) were recruited from the outpatient headache clinic at Glostrup Hospital. There were 2 males and 3 females, and the mean age was 45.4 years (range 39–48). The mean life time duration of chronic tension-type headache was 12.2 years (range 4–25). One patient had coexisting but infrequent migraine. Exclusion criteria were; daily major medication (including prophylactic headache therapy); abuse of analgesics or alcohol; serious somatic or psychiatric diseases including depression.

Procedures

Using an open labeled design, patients fulfilled a diagnostic headache diary during at least 4 weeks run-in period to ensure the diagnostic criteria. Thereafter, the patients received Dextromethorphan (Dexofan®) tablets at 30 mg each, three times per day. The treatment period lasted 4 weeks, and during this period patients were asked to continue Faith headache diaries: and record headache intensity, frequency, duration, any medication taken and any possible adverse events. At a follow up visit at day 29–32, diaries were collected and possible adverse events and evaluation of the treatment were recorded. Due to the restricted number of patients, no statistical analysis were done. The efficacy parameters were headache intensity, frequency and duration, and intake of simple analgesics. Mean values from the run-in period were compared to those obtained during the treatment period.

Results

All patients completed the study. The intensity of headache was reduced 18% namely from 4.4 on a 0–10 VAS intensity scale during the run-in period to 3.6 during active treatment. Duration of the individual headache episode was reduced by 11%, and frequency of headache decreased by 4%, namely from 28 days per 4 weeks period during run-in to 27 days per 4 weeks period during active treatment. Intake of analgesics decreased by 72% from a mean intake at 1.8 dose per day during run-in period to 0.5 dose per day during active treatment. Two patients reported a marked effect with considerable relief of headache intensity and duration within very few days of treatment, one patient had a slight relief of headache intensity and two patients reported no effect at all Four patients reported no side effects, and marked side effects with sedation was reported in one patient, the patient with best clinical response. These side effects diminished considerably after a dose reduction to 40 mg per day.

Discussion and Conclusion

The present results suggest a positive prophylactic effect of Dextromethorphane in chronic tension-type headache. The lack of effect in some patients may be due to a relatively small dosage. Although the exact mechanism of Dextromethorphane is not fully elucidated, the preliminary evidence in experimental pain model is in favor of an effect according to the present, pathophysiological model of chronic tension-type headache, i.e. the central sensitization model of the present invention.

EXAMPLE 8

Possible Mechanisms of Action of Nitric Oxide Synthase Inhibitors in Chronic Myofascial Pain Pain from the musculoskeletal system is probably the most common type of chronic pain (Magni et al. 1990). Progress in basic pain research has increased our knowledge about the mechanisms underlying chronic myofascial pain (Mense 1993). Thus, substantial experimental evidence indicates that central sensitization generated by prolonged nociceptive input from the periphery plays an important role in the pathophysiology of chronic pain particularly from myofascial tissues (Woolf 1983; Hu et al. 1992; Woolf and Doubell 1994; Bendtsen et al. 1996a). The freely diffusible gas nitric oxide (NO) is assumed to be of importance for the development of central sensitization (McMahon et al. 1993; Meller and Gebhart 1993). Thus, nitric oxide synthase (NOS) inhibitors reduce central sensitization in animal models of persistent pain (Haley et al. 1992; Hao and Xu 1996; Mao et al. 1997). We recently demonstrated that NOS inhibition has an analgesic effect in patients with chronic myofascial pain (Ashina et al. 1993a). However; the mechanisms of this effect have so far been unknown. The aim of the present study was to investigate whether the NOS inhibitor, L-$N^G$ methyl arginine hydrochloride (L-NMMA), modulates muscle hardness (Sakai et al. 1995) and myofascial tenderness (Jensen et al. 1998) in patients with chronic myofascial pain.

Materials and Methods

Subjects

Sixteen patients with a diagnosis of chronic tension-type headache according to the criteria of the International Headache Society (Headache Classification Committee 1988) were included (Table XVII). Five of the patients had coexisting infrequent migraine (<four days/year). The patients were recruited from the out-patient headache clinic at Glostrup University Hospital without respect to presence or absence of myofascial tenderness. All patients underwent a general physical and a neurological examination and completed a diagnostic headache diary during a 4-week run-in period (Russell et al. 1992). Exclusion criteria were: daily medication (including prophylactic headache therapy but not oral contraceptives); abuse of analgesics (corresponding to>2 gm of aspirin/day); serious somatic or psychiatric diseases including depression (Hamilton Depression Score #17 (Hamilton 1960)). Patients were examined and treated during a typical day of tension-type headache. All patients gave written consent to participate in the study, which was approved by the Danish Board of Health and the local ethics committee. The study was conducted in accordance with the Declaration of Helsinki.

Apparatus

Muscle hardness. The muscle hardness of the trapezius muscle was measured with a hardness meter, which has previously been described in detail (Horikawa et al. 1993). In brief, the hardness meter consists of a laser distance sensor and a pressure terminal with a surface area of 1 $cm^2$. The muscle hardness is estimated by recording the relation between the applied pressure and the displacement of the skin over the muscle. All calculations are performed by a software-program in order to avoid observer bias. Hardness is expressed in kPa/cm. We have previously demonstrated that the hardiness meter can measure muscle hardness reliably if the same observer is used throughout a study (Ashina et al. 1998b).

Pressure pain thresholds. An electronic pressure algometer (Somedic AB, Stockholm, Sweden) was used to measure pressure pain thresholds. The algometer has been described in detail elsewhere (Jensen et al. 1986). A circular stimulation probe (0.50 $cm^2$) and a pressure loading rate of 22 kPa/s (1 kPa=$10^3$ $N/m^2$) were used.

Methods

The recordings were performed in a standardized manner by the same observer, a trained technician (HA), throughout the study. All parameters were recorded at baseline, 60 and 120 minutes after start of infusion. The trial was designed as a double blind, placebo controlled, crossover study. The first part of the study examined the analgesic effect of L-NMMA and has previously been described in detail (Ashina et al. 1998a). Briefly, patients were randomized to receive 6 mg/kg L-NMMA (Clinalfa, Switzerland) or placebo (isotonic glucose) over 15 minutes into an antecubital vein on two days separated by at least one week. The patients were not allowed to take analgesics 12 hours prior to the examination. Headache intensity was measured on a 100 mm Visual Analog Scale (VAS) (0-no headache and 100-worst imaginable headache) before, during and after start of infusion.

Muscle hardness. The muscle hardness was measured at a standard anatomical point on the trapezius muscle On the non-dominant side, as previously described (Ashina et al. 1998b). Briefly, the point was located on the center of the descending part of the trapezius muscle midway between the processus spinosus of the seventh cervical vertebra and the acromion. The muscle hardness was calculated as the mean of five consecutive determinations. All recordings were stored in the computer, and they were not analyzed before the study was completed.

Total tenderness. Tenderness of pericranial myofascial tissues was recorded according to the Total Tenderness Scoring system (Langemark and Olesen 1987),which has previously proved to be reliable (.Bendtsen et al. 1995). Eight pairs of muscles and tendon insertions (masseter, temporal, frontal, sternocleidomastoid and trapezius muscles, coronoid and mastoid processes, and neck muscle insertions) were palpated. Tenderness was scored on a 4-point (0–3) scale at each location (local tenderness score) and values from left and right sides were summed to a Total Tenderness Score (TTS) (maximum possible score=48).

Pressure pain thresholds Pressure pain detection thresholds (PPDTs) were measured at the dorsum of the second finger (middle phalanx) and at a fixed point at the anterior part of the temporal muscle as previously described (Bendtsen et al. 1996b). Measurements were performed at the non-dominant side. The PPDT was defined as the pressure at which the sensation changed from pressure alone to pain. The subject indicated that the pain threshold was reached by pressing a handheld button. The algometer display was thereby Afrozen@ and the pressure was immediately released. Each threshold was calculated as the mean of five consecutive determinations performed with intervals of approximately 30 seconds.

Data Analysis and Statistics

Results are presented as means SDs. For each of the variables, the sum of the differences between the pretreatment value and each of the post-treatment values was calculated in order to obtain a summary measure of effect for each treatment (Matthews et al 1990). The summary scores calculated for active treatment and placebo were compared by use of the Wilcoxon Signed Ranks test Within each treatment pre-treatment values were compared with values at 60 and 120 minutes post dosing by use of the Wilcoxon Signed Ranks test. Five percent was accepted as level of significance.

Results

Muscle hardness The summary scores of muscle hardness of the trapezius muscle was reduced significantly more following treatment with L-NMMA compared with placebo (p=0.04) (FIG. 17). Compared to baseline, hardness was significantly reduced at 60 and 120 minutes after treatment with L-NMMA (p=0.04 and p<0.05, respectively). There was no significant reduction in muscle hardness at any time after treatment with placebo (Table XVIII).

Tenderness. The summary of tenderness score tended to be reduced more following treatment with L-NMMA than with placebo, but the difference was not statistically significant (p=0.11) (FIG. 18). However, compared to baseline TTS was significantly), reduced at 60 and 120 minutes after treatment with L-NMMA compared with pre-treatment values (p=0.007 and p=0.008, respectively). There was no significant reduction in TTS at any time after treatment with placebo (Table XVIII).

Pressure pain thresholds. There was no significant difference between PPDTs recorded during treatment with L-NMMA and placebo (finger: p=0.78 and temporal region: p=0.77). There were also no changes in PPDTs at 60 and 120 minutes after treatment with L-NMMA compared with pre-treatment values neither in the finger nor in the temporal region (Table XVIII). Compared to baseline PPDT decreased significantly in the finger (p=0.04), but not in the temporal region following treatment with placebo (Table XVIII).

Pain intensity. Pain intensity was significantly more reduced following treatment with L-NMMA than following treatment with placebo (FIG. 19) as previously reported (Ashina et al. 1998a). Pain scores were significantly reduced at each time point after treatment with L-NMMA, while there was no significant reduction in pain intensity at any time point after treatment with placebo (FIG. 19).

Discussion

In the present study, chronic tension-type headache was used as a model for chronic myofascial pain, since nociception from myofascial tissues probably plays an important role in the pathophysiology of chronic tension-type headache. Thus, several studies have consistently reported increased myofascial tenderness as the most prominent abnormal finding in patients with chronic tension-type headache (Langemark and Olesen 1987; Jensen et al. 1993; Jensen et al. 1998; Bendtsen et al. 1996b; Lipchik et al. 1997; Ashina et al. 1998b). A further support for myofascial involvement is the recent findings of increased muscle hardness (Sakai et al. 1995) and a positive correlation between muscle hardness and tenderness in chronic tension-type headache (Ashina et al. 1998b). The mechanisms contributing to the increased tenderness and muscle hardness are unknown. Recently it has been suggested that the increased tenderness in patients with chronic tension-type headache and fibromyalgia may be due to central sensitization of spinal dorsal horn neurons induced by prolonged nociceptive input from myofascial tissues (Bendtsen et al. 1996a, 1997; Jensen et al. 1998). An investigation of myofascial tenderness and muscle hardness in patients with chronic tension-type headache may therefore contribute to our understanding of myofascial pain.

Animal experiments have suggested that NO is an important transmitter in pain pathways of the spinal cord and that sensitization of these pathways may be caused by or associated with activation of NOS and the generation of NO (Haley et al. 1992; Meller et al. 1992; Meller and Gebhart 1993). In support for is, it has recently been shown in animal models of persistent pain that NOS inhibitors reduce spinal dorsal horn sensitization induced by continues painful input from the periphery (Meller et al. 1994; Roche et at, 1996; Mao et al. 1997). In addition, we have recently demonstrated that NOS inhibition has an analgesic effect in patients with chronic myofascial pain (Ashina et al. 1998a). In the latter study we found that headache intensity was significantly reduced during treatment with L-NMMA compared with placebo. The present study provides important information about the mechanisms of the antinociceptive action of NOS inhibition in chronic myofascial pain. We found that both muscle hardness and tenderness were significantly reduced at each time point after treatment with L-NMMA, while there was no significant reduction in muscle hardness or tenderness at any time after treatment with placebo. Although the tenderness was significantly reduced, the reduction of tenderness compared to placebo was not significant. This may be due to lack of statistical power. The muscle hardness was significantly reduced following treatment with L-NMMA compared to placebo. Although statistically significant, the reduction of hardness was very small. This is understandable because the increased hardness is a rather stable feature (Ashina et al. 1998c) which is not easy to change in an acute experiment. Similar arguments apply to myofascial tenderness (Jensen et al. 1998). Long term treatment could perhaps result in larger changes. The importance of the present results lies in the proof of concept not in the magnitude of the effect. The pressure pain detection thresholds in the finger and temporal region were largely unchanged following treatment with L-NMMA. This indicates that L-NMMA did not significantly alter general pain sensitivity. The questions are what mechanisms leading to the increased muscle hardness and tenderness; how L-NMMA modulates muscle hardness and tenderness; and whether the effects of L-NMMA observed in the present study are due to an action in muscle or in the CNS? It has been shown that the central neuroplastic chances may increase the drive to motor neurons both at the supraspinal and the segmental level (Woolf 1983). In this way it is possible that sustained muscle contraction due to increased hypersensitivity in CNS contributes to increased muscle hardness and tenderness in chronic tension-type headache. This is supported by recent findings of increased tenderness and muscle activity in patients with chronic tension-type headache was found not only on days with headache but also on days without headache (Lipchik et al. 1997; Ashina et al. 1998b; Jensen et al. 1998). Furthermore, muscle hardness recorded in patients on days with headache did not differ from hardness recorded on days without headache (Ashina et al. submitted 1998b). Collectively, these results indicate that permanently altered muscle hardness, tenderness and muscle activity may reflect an increased input from myofascial nociceptors with subsequent sensitization of second order neurons. L-NMMA inhibits all three types of NOS (endothelial NOS, neuronal NOS and inducible NOS) (Southern and Szabo 1996) and rich sources of nNOS are present not only in nervous tissue but also in all striated muscles of mammals (Grozdanovic et al. 1995). In addition to nNOS, skeletal muscles also contain eNOS. Recent study has demonstrated that NO has important physiological functions in skeletal muscles such as promoting relaxation and modulating increases in contraction (Kobzik et al. 1994). Interestingly, contractile function of muscles was enhanced by blockers of NO synthase (Kobzik et al. 1994). Because of this inverse correlation between contractile function and nNOS activity, one could expect that L-NMMA will induce the contraction of muscle with subsequent increase of muscle hardness and tenderness. However, in the present study we observed the reduction of muscle hardness and tenderness following treatment with L-NMMA. Thus, the effects of L-NMMA observed in the present study may be due to reduction of sensitization of second order neurons receiving input from myofascial tissues and locating at the level of the spinal dorsal horn/trigeminal nucleus.

The increased muscle hardness and tenderness may reflect a tissue oedema or metabolic alterations due to microcirculatory disturbance (Henriksson et al. 1993). It is possible that L-NMMA acts directly in myofascial tissues or nociceptors located in such tissues. Thus, the ability of NOS inhibitors to cause vasoconstriction (Rees et al. 1990) may prevent inflammatory mediators and algogenic substances involved in hardness and tenderness from reaching their site of action Haley et al. 1992). In addition, it has been demonstrated that NOS inhibitors have antinociceptive effect after peripheral administration (Haley et al. 1992; Kindgren-Milles and Arndt 1996; Nakamura et al. 1996). However, the exact role of NO in the periphery is still far from understood, and additional research is needed to clarify whether NO may activate or sensitize peripheral nociceptors. The antinociceptive effect of NOS inhibition might also result from non-specific effects elicited by L-NMMA, such as changes in blood pressure and pulse rate. Mean arterial blood pressure and pulse rate were continuously monitored in the present study. We found that the peak increase in mean arterial blood pressure (12%) and maximum decrease in pulse rate (16%) occurred 15 and 10 minutes respectively after treatment with L-NMMA. The difference in the mean arterial blood pressure and pulse rate between L-NMMA and placebo disappeared 60 minutes after start of infusion (Ashina et al. 1998a). In contrast, the antinociceptive effect on headache intensity and the reduction of muscle hardness and tenderness lasted at least 120 minutes after start of infusion. It therefore seems unlikely that the observed effects of L-NMMA were caused by hypertensive effects of the agent. In conclusion, the present study indicates that the NOS inhibitor L-NMMA elicits its antinociceptive effect in myofascial pain by modulation of nociceptive information from myofascial tissues. This antinociceptive effect is probably caused by reduction of central sensitization at the level of the spinal dorsal horn/trigeminal nucleus.

Table XVII

Clinical data on patients.

| | Patients |
|---|---|
| Number | 16 |
| Females/males | 12/4 |
| Age, years | 39 (23–52) |
| Headache frequency, days/4 weeks | 22 (15–28) |

Mean values with range given within parentheses.

Table XVIII

Muscle hardness, Total Tenderness Score (TTS) and pressure pain detection thresholds (PPDT) in the finger and the temporal region (TR) recorded before and 60 and 120 minutes after start of the infusion of L-NMMA or placebo.

| | | Baseline | 60 minutes | 120 minutes |
|---|---|---|---|---|
| Muscle hardness | L-NMMA | 107 ± 17 | 101 ± 17* | 101 ± 17* |
| | Placebo | 106 ± 18 | 104 ± 17$^{NS}$ | 105 ± 22$^{NS}$ |
| TTS | L-NMMA | 18 ± 11 | 15 ± 11** | 14 ± 11** |
| | Placebo | 17 ± 12 | 16 ± 13$^{NS}$ | 15 ± 13$^{NS}$ |
| PPDT/finger | L-NMMA | 455 ± 155 | 436 ± 129$^{NS}$ | 449 ± 144$^{NS}$ |
| | Placebo | 457 ± 141 | 435 ± 143$^{NS}$ | 420 ± 130* |
| PPDT/TR | L-NMMA | 279 ± 108 | 264 ± 86$^{NS}$ | 277 ± 95$^{NS}$ |
| | Placebo | 274 ± 104 | 271 ± 109$^{NS}$ | 262 ± 95$^{NS}$ |

Mean values (± SDs) are given. Post treatment values compared with pre-treatment values (Wilcoxon Signed Ranks test).
**= $p < 0.009$, *= $p < 0.05$ and NS = not significant.

REFERENCES

Atkins, C. J., Zielinski, A., Klinkhoff, A. V., Chalmers, A., Wade, J., Williams, D., Schulzer, M. and Della Cioppa, G., An electronic method for measuring joint tenderness in rheumatoid arthritis, Arthritis Rheum, 35(1992) 407–410.

Ashina, M., Bendtsen, L., Jensen, R., Sakai, F. and Olesen, J., The measurement of muscle hardness: a methodological study, Cephalalgia 18, (1998a): 106–111.

Ashina, M., Bendtsen, L., Jensen, R., Sakai, F. and Olesen, J., Muscle hardness in patients with chronic tension-type headache: relation to actual headache state, Submitted 1998c.

Bakke M, Michler L, Hansen K E, Møller E. Clinical significance of isometric force versus electrical activity in temporal and masseter muscles. Scand J Dent Res (1989); 97:539–51.

Bendtsen, L. Jensen, R., Jensen, N. K. and Olesen, J., Muscle palpation with controlled finger pressure: new equipment for the study of tender myofascial tissues, Pain, (1994); 59:235–239.

Bendtsen L, Jensen R, Jensen N K, Olesen J. Pressure controlled palpation: a new technique which increases the reliability of manual palpation. Cephalalgia, (1995a); 15:205–210.

Bendtsen L, Jensen R, Olesen J., Quantitatively changed noxious thresholds in chronic tension-type headache, Cephalalgia, (1995b); 15:143

Bendtsen, L., Jensen, R., Brennum, J., Arendt-Nielsen, L. and Olesen, J., Exteroceptive supression of temporalis muscle activity is normal in patients with chronic tension-type headache and not related to actual headache state, Cephalalgia, (1996a); 16:251–256

Bendtsen, L., Jensen, R. and Olesen, J., Decreased pain detection and tolerance thresholds in chronic tension-type headache, Arch Neurol, (1996b); 53;373–376.

Bendtsen, L., Jensen, R. and Olesen, J., Qualitatively altered nociception in chronic myofascial pain, Pain, (1996c); 65:259–264.

Bendtsen, L., Jensen, P and Olesen, J., A non-selective (amitriptyline), but not a selective (citalopram), serotonin reuptake inhibitor is effective in the prophylactic treatment of chronic tension-type headache, J Neurol Neurosurg Psychiatry, 61(1996d)285–290.

Bendtsen L, Nørregaard J, Jensen R, Olesen J. Evidence for a qualitative altered nociception in fibromyalgia. Arthritis Rheumatism, (1997); 40:98–102

Boivie, J., Central pain. In: P. D. Wall and R. Melzack (Eds.), Textbook of pain, Third Edition, Churchill Livingstone, Edinburgh (1994) pp 871–902.

Bovim G. Cervicogenic headache, migraine and tension-type headache. Pressure pain thresholds measurements. Pain (1992); 51:169–173.

Brennum J, Kjeldsen M, Jensen K, Jensen T S. Measurement of human pressure-pain thresholds on fingers and toes. Cephalalgia (1989); 9:131–132.

Brennum, J., Kjeldsen, M. and Olesen, J., 5-HT-like agonist sumatriptan has a significant effect in tension-type headache. Cephalalgia (1992); 12:375–379

Brennum, J., Brinck, T., Schriver, I., Wanscher, B., Soelberg Sorensen, P., Tfelt-Hansen, P., Olesen, J., Sumatriptan has no clinically relevant effect in episodic tension-type headache. Eur J Neurol. (1996); 3:23–28

Campell J N, Srinivasa N R, Cohen R H, Manning D C, Khan A A, Meyer R A. Peripheral neural mechanisms of nociception. In: Wall P D, Melzack R eds. Textbook of Pain. Churchill Livingstone, Edinburgh 1989;22–45.

Cervero, F. and Sann, H., Mechanically evoked responses of afferent fibers innervating the guinea-pig's ureter: an in vitro study, J Physiol (Lond), (1989); 412:245–266.

Cervero, F. and Janig, W., Visceral nociceptors: a new world order? Trends Neurosci, (1992); 15:374–378.

Christensen L V. Jaw muscle fatigue and pains induced by experimental tooth clenching: a review. J Oral Rehab (1981); 8:27–36.

Clark G T, Adler R C, Lee J J. Jaw pain and tenderness during and after repeated sustained maximum voluntary protrusion. Pain (1991); 45:17–22.

Clark C T, Sakai S, Merrill R, Flack V F, McCreary C. Cross-correlation between stress, pain, physical activity, and temporalis muscle EMG in tension-type headache. Cephalalgia 1995;15:511–8

Coderre T J, Katz J, Vaccarino A L, Melzack R. Contribution of central neuroplasticity to pathological pain: review of clinical and experimental evidence. Pain (1993); 52.259–285.

Dickenson, A H., Pharmacology of pain transmission and control. In: J. Cambell (Ed.), Pain 1996—An updated review, IASP Press. Seattle. (1996) pp 113–121.

Drummond P D. Scalp tenderness and sensitivity to pain in migraine and tension headache. Headache (1987); 27:45–50.

Dubner, R. and Ruda, M. A., Activity-dependent neuronal plasticity following tissue injury and inflammation, Trends Neurosci, 15(1992)96–103.

Fields, H. L. and Basbaum, A. I., Central nervous system mechanisms of pain modulation. In: P. D. Wall and R. Melzack (Eds.), Textbook of pain, Third Edition, Churchill Livingstone, Edinburgh (1994) pp 243–257.

Fruhstorfer H, Lindblom U, Schmidt W G. Method for quantitative estimation of thermal thresholds in patients. J Neurol Neurosurg Psychiat (1976); 39:1071–1075.

Gee N S, Brown J P, Dissanayakake V U, Offord J, Thurlow R, Woodruff G N. The novel anticonvulsant drug gabapentin (neurontin) binds to alpha-2-delta subunit of a calcium channel. J Biol Chem 1996;90:164.

Goebel H, Weigle L. Kropp P, Soyka D. Pain sensitivity and pain reactivity of pericranial muscles in migraine and tension-type headache. Cephalalgia (1992); 12:142–151.

Grozdanovic, Z., Nakos, G., Dahrmann, G., Mayer, B. and Gossrau, R., Species-independent expression of nitric oxide synthase in the sarcolemma region of visceral and somatic striated muscle fibers, Cell Tissue Res, 281(1995) 493–499.

Haley J E, Dickenson A H, Schachter M. Electrophysiological evidence for a role of nitric oxide in prolonged chemical nociception in the rat. Neuropharmacology 1992;31:251–258.

Hamilton M. A Rating Scale for Depression. J Neurol Neurosurg Psychiatry 1960;23:56–62.

Hao, J. -X., Xu, X. -J., Aldskogius, H., Seiger, Å. and Wiesenfeld-Hallin, Z., Photochemically and induced transient spinal ischemia induces behavioral hypersensitivity to mechanical cold stimuli, but not to noxious-heat stimuli, in the rat, Experimental Neurology, 118(1992) 157–194.

Hao J-X, Xu X-J. Treatment of chronic allodynia-like response in spinally injured rats: effects of systemically administered nitric oxide synthase inhibitors. Pain 1996;66:313–319.

Hatch J, Moore P, Cyr-Provost M, Boutros N, Seleshi E, Borcherding S. The use of electromyography and muscle palpation in the diagnosis of tension-type headache with and without pericranial muscle involvement. Pain (1992); 4:175–178.

Headache Classification Committee of the International Headache Society. Classification and Diagnostic criteria for headache disorders, cranial neuralgias and facial pain. Cephalalgia (1988);8 suppl.7.

Heppelman B. Hebert M K, Schaible H G, Schmidt R F. Morphological and physiological characteristics of the innervation of cat's normal and arthritic knee joint. In: Hubols L S, Sessle B J, Liss A R eds. Effect of the injury of the trigeminal and spinal somatosensory system. Alan R Liss, New York 1987; 19–27.

Hoheisel U, Koch K, Mense S. Functional reorganization in the rat dorsal horn during an experimental myositis. Pain (1994); 59:111–118.

Horikawa, M., Ebihara, S., Sakai, F. and Akiyama, M., Non-invasive measurement method for hardness in muscular tissues, Medical & Biological Engineering & Computing, 31 (1993) 623–627.

Howell, J. N., Chleboun, G. and Conatser, R., Muscle stiffness, strength loss, swelling and soreness following exercise-induced injury in humans, J Physiol (Lond), 464(1993)183–196.

Hu, J W, Sessle, B J, Raboisson, P, Dallel, R and Woda, A, Stimulation of craniofacial muscle afferents induces prolonged facilitatory effects in trigeminal nociceptive brainstem neurons, Pain, (1992); 48:53–60.

Hwang J, Yaksh T L. The effect of intrathecal gabapentin on tactile evoked allodynia in a surgically induced neuropathic pain model in the rat. Regional Anaest 1997, in press.

Hylden, J. L., Nahin, R. L., Traub, R. J. and Dubner, R., Expansion of receptive fields of spinal lamina I projection neurons in rats with unilateral adjuvant-induced inflammation: the contribution of dorsal horn mechanisms, Pain, 37(1989)229–243.

Jamal G A, Hansen S. Weir A I, Ballantyne J P. An improved automated method for the measurement of thermal thresholds. 1. normal subjects. J Neurol Neurosurg Psychiat (1985); 48:354–360.

Jensen K, Bülow P, Hansen H. Experimental toothclenching in common migraine. Cephalalgia (1985); 5:245–51.

Jensen K, Andersen H O. Olesen J, Lindblom U. Pressure-Pain Threshold in Human Temporal Region. Evaluation of a new Pressure Algometer. Pain (1986); 25:313–323.

Jensen K. Quantification of tenderness by palpation and use of pressure algometer. Adv Pain Res Ther (1990); 17:165–181.

Jensen, K., Tuxen, C., Pedersen Bjergaard, U., Jansen, I., Edvinsson, L. and Olesen, J., Pain and tenderness in human temporal muscle induced by bradykinin and 5-hydroxytryptamine, Peptides, 11(1990)1127–1132.

Jensen K, Norup M. Experimental pain in human temporal muscle induced by hypertonic saline, potassium and acidity. Cephalalgia (1992); 12:101–106.

Jensen R, Fuglsang-Frederiksen A, Olesen J. Quantitative surface EMG of the pericranial muscles. Reproducibility and variability. Electroenceph clin Neurophysiol. (1993a); 89:1–9.

Jensen R, Rasmussen B K, Pedersen B, Olesen J. Cephalic muscle tenderness and pressure pain threshold in headache. A population study. Pain (1993b); 52:193–199.

Jensen R, Fuglsang-Frederiksen A, Olesen J. Quantitative surface EMG of pericranial muscles in headache. A population study. Electroenceph clin Neurophysiol. (1994); 93:335–344.

Jensen, R., Variation in pain thresholds and tenderness during spontaneous tension-type headache, Cephalalgia, (1995a); 15:148.

Jensen, R., Mechanisms of spontaneous tension-type headaches. An analysis of tenderness, pain thresholds and EMG, Pain, (1995b); 64:251–256.

Jensen, R. and Olesen, J., Initiating mechanisms of experimentally induced tension-type headache, Cephalalgia, (1996A); 16:175–182.

Jensen R. Mechanisms of spontaneous tension-type headaches. An analysis of tenderness, pain thresholds and EMG. Pain, (1996B); 64:251–256

Jensen, R. and Rasmussen, B. K., Muscular disorders in tension-type headache [see comments], Cephalalgia, 16(1996)97–103.

Jensen R, Rasmussen B K, Olesen J. Muscular disorders in tension-type headache. Interrelations between manual palpation, pressure pain threshold and EMG levels in a general population. Cephalalgia (1996C); 16:97–103.

Jensen R, Bendtsen L, Olesen J. Importance of muscular factors in tension-type headache. 8th Congress of The International Headache Society. Amsterdam 1997a Jensen R, Bendtsen L, Olesen J. Muscular factors are of importance in tension-type headache. Abstract. 39th Annual Scientific Meeting of American Association for the Study of Headache, New York 1997b, Jensen R, Bendtsen L, Olesen J. Muscular factors are of importance in tension-tape headache. Accepted, Headache 1997c.

Jensen, R., Bendtsen, L. and Olesen, J., Muscular factors are of importance in tension-type headache, Headache, 38 (1998) 10–17.

Jänig, W. and Koltzenburg, M., Receptive properties of sacral primary afferent neurons supplying the colon, J Neurophysiol, (1991); 65:1067–1077.

Kindgen-Milles D, Arndt J O. Nitric oxide as a chemical link in the generation of pain from veins in humans. Pain 1996;64:139–142.

Kobzik, L., Reid. M. B., Bredt, D. S. and Stamler, J. S., Nitric oxide in skeletal muscle, Nature, 372 (1994) 546–548.

Koltzenburg, M., Kress, M. and Reeh, P. W., The nociceptor sensitization by bradykinin does not depend on sympathetic neurons, Neuroscience, (1992); 46:465–473, Laird, J. M. A., de la Rubia, P. G. and Cervero, F., Excitability changes of somatic and viscero-somatic nociceptive reflexes in the decerebrate-spinal rabbit: role of NMDA receptors, J Physiol (Lond), 1(1995)545–555.

La Motte R H, Simone D A, Baumann T K, Shain C N, Alreja M Hypothesis for novel classes of chemoreceptors mediating chemogenic pain and itch. In: Dubner R, Gebhart G F, Bond M R, eds Proceedings of the fifth world congress of pain. Elsevier Amsterdam 1988:529–535.

Langemark M, Olesen J. Pericranial tenderness in tension headache. Cephalalgia (1987); 7:249–255.

Langemark, M., Olesen, J., Poulsen, D. L. and Bech, P., Clinical characterization of patients with chronic tension headache, Headache, (1988); 28:590–596.

Langemark M, Jensen K, Jensen T S, Olesen J. Pressure pain thresholds and thermal nociceptive thresholds in chronic tension-type headache. Pain (1989); 38:203–210.

Langemark M, Jensen K, Olesen J. Temporal muscle blood flow in chronic tension-type headache, Arch Neurol (1990); 47:654–658.

Le Bars D, Dickerson A H, Besson J M. Diffuse noxious inhibitory controls (DNIC). I. Effects on dorsal horn convergent neurons in the rat. Pain (1979); 6:283–304.

Levine, J. and Taiwo, Y., Inflammatory pain. In: P. D. Wall and R. Melzack (Eds.), Textbook of pain, Third Edition, Churchill Livingstone, Edinburgh (1994) pp 45–56.

Lipchik, G., Holroyd K A, France C R, Kvaal S A, Segal D, Cordingly G E, Rokicki L A, McCool H R, Central and peripheral mechanisms in chronic tension-type headache. Pain (1996); 64:467–475.

Lipchick, G. L., Holroyd, K. A., Talbot, F. and Greer, M., Pericranial muscle tenderness and exteroceptive suppression of temporalis muscle activity: A blind study of chronic tension-type headache, Headache, 37 (1997) 368–376.

Lous I, Olesen J. Evaluation of pericranial tenderness and oral function in patients with common migraine, muscle contraction headache and combination headache. Pain (1982); 12:385–393

Magerl, W., Wilk, S. H. and Treede, R. -D., Secondary hyperalgesia and perceptual wind-up following intradermal injection of capsaicin in humans, Pain, 74(1998) 257–268.

Magni, G., Caldieron, C., Rigatti Luchini, S. and Merskey, H., Chronic musculoskeletal pain and depressive symptoms in the general population. An analysis of the 1st National Health and Nutrition Examination Survey data, Pain, 43 (1990) 299–307.

Magnusson T, Enbom L. Signs and symptoms of mandibular dysfunction after introduction of experimental balancing side interferences. Acta Odontol Scand (1984); 42:129–135.

Mao J, Price D D, Zhu J, Lu J, Maser D J. The inhibition of nitric oxide-activated poly (ADP-ribose) synthase attenuates transsynaptic alteration of spinal cord dorsal horn neurons and neuropathic pain in the rat. Pain 1997;72:355–366.

Matthews, J. N., Altman, D. G., Campbell, M. J. and Royston, P., Analysis of serial measurements in medical research, BMJ, (1990); 300:230–235.

McMahon, S. B., Lewin, G. R. and Wall, P. D., Central hyperexcitability triggered by noxious inputs, Curr Opin Neurobiol, (1993); 3:602–610.

Meller, S. T., Dykstra, C. and Gebhart, J. F., Production of endogenous nitric oxide and activation of soluble guanylate cyclase are required for N-methyl-D-aspartate-produced facilitation of the nociceptive tail-flick reflex, Eur J Pharmacology, 214 (1992) 93–96.

Meller, S. T. and Gebhart, G. F., Nitric oxide (NO) and nociceptive processing in the spinal cord, Pain, (1993); 52:127–136.

Meller, S. T., Cummings, C. P., Traub, R. J. and Gebhart, G. F., The role of nitric oxide in the development and maintenance of the hyperalgesia produced by intraplantar injection of carrageenan in the rat, Neuroscience, 60 (1994) 367–374.

Mense S. Nociception from skeletal muscle in relation to clinical muscle pain. Pain (1993); 54:241–289.

Meyer R A, Cambell J M, Srinivasa N R, Peripheral neural mechanisms of nociception, in Textbook of pain (1994); 13–14.

Mayer, E. A. and Gebhart, G. F., Basic and clinical aspects of visceral hyperalgesia, Gastroenterology, (1994); 107:271–293.

Moncada S, Palmer R M, Higgs E A. Nitric oxide: physiology, pathophysiology, and pharmacology. Pharmacol Rev 1991;43:109–142.

Myers D E, McCall W D. Head pain as a result of experimental ischemic exercise of the temporalis muscle. Headache (1983); 23:113–116

Nakamura, A., Fujita, M. and Shiomi, H., Involvement of endogenous nitric oxide in the mechanism of bradykinin-induced peripheral hyperalgesia, Br J Pharmacol, 117 (1996) 407–412.

Ness, T. J. and Gebhart, G. F., Quantitative comparison of inhibition of visceral and cutaneous spinal nociceptive transmission from the midbrain and medulla in the rat, J Neurophysiol, (1987); 58:850–865, Nørregaard, J., Bendtsen, L., Lykkegaard, J. and Jensen, R., Pressure and heat pain thresholds and tolerances in patients with fibromyalgia, 3 of Musculoskeletal Pain, 5(1997)43–53.

Olesen J, Jensen R. Getting away from simple muscle contraction as a mechanism of tension-type headache. Pain (1991); 46:123–124.

Pedersen, J. L., Andersen, O. K., Arendt-Nielsen, L. and Kehlet, H., Hyperalgesia and temporal summation of pain after heat injury in man, Pain, 74(1998)189–197.

Persson J, Axelsson G, Hallin R G, Gustafsson L L. Beneficial effects of ketamine in a chronic pain state with allodynia, possibly due to central sensitisation. Pain 1995;60:217–22.

Petersen K L, Brennum J, Olesen J. Evaluation of pericranial myofascial nociception by pressure algometer. Reproducibility and factors of variation. Cephalalgia (1992); 12:33–37

Pfaffenrath, V., Diener, H. C., Isler, H., Meyer, C., Scholz, E., Taneri, Z., Wessely, P., Zaiser Kaschel, H., Haase, W. and Fischer, W., Efficacy and tolerability of amitriptylinoxide in the treatment of chronic tension-type headache: a multi-center controlled study, Cephalalgia, 14(1994) 149–155.

Pikoff H. Is the muscular model of headache still viable? A review of conflicting data. Headache (1984); 24:186–198.

Price D D, Mao J, Frank H, Macer D J. The N-methyl-D-aspartate receptor antagonist dextromethorphan selectively reduces temporal summation of second pain in man. Pain 1994;59:165–74.

Rang, H. P., Bevan, S. and Dray A., Nociceptive peripheral neurons: cellular properties. In: P. D. Wall and R. Melzack (Eds.), Textbook of pain, Third Edition, Churchill Livingstone, Edinburgh (1994) pp 57–78.

Rasmussen B K, Jensen R, Schroll M, Olesen J. Epidemiology of headache in a general population—A prevalence study. J Clin Epidemiol (1991); 44:1147–57.

Rasmussen B K, Jensen R, Olesen J. Impact of headache on sickness absence and utilization of medical services: a Danish population study. J Epidemiol Community Health (1992); 46:443–446.

Rasmussen B K. Migraine and tension-type headache in a general population: precipitating factors, female hormones, sleep pattern and relation to lifestyle. Pain 1993;53:65–72.

Rees, D. D., Palmar, R. M. J., Schulz, R, Hodson, H. F. and Moncada, S., Characterization of three inhibitors of endothelial nitric oxide synthase in vitro and in vivo, Br J Pharmacol, 101 (1990) 746–752.

Roberts, M. H. T., 5-hydroxytryptamine in nociception and antinociception. In: J. Olesen and P. R. Saxena (Eds.), 5-hydroxytryptamine mechanisms in primary headaches, Raven Press, New York (1992) pp 69–76.

Roche A K, Cook M, Wilcox G L, Kajander K C. A nitric oxider synthesis inhibitor (L-NAME) reduces licking behavior and Fos-labeling in the spinal cord of rats during formalin-induced inflammation. Pain 1996;66:331–341.

Rosner H, Rubin L, Kestenbaum A. Gabapentin, adjunctive therapy in neuropathic pain states. Clin J Pain 1996;12:56–58.

Russell, M. B. Rasmussen, B. K., Brennum, J., Iversen, H. K., Jensen, R. A. and Olesen, J, Presentation of a new instrument: the diagnostic headache diary, Cephalalgia, (1992); 12:369–374.

Sandrini G, Antonaci F, Pucci E, Bono G, Nappi G. Comparative study with EMG, pressure algometry and manual palpation in tension-type headache and migraine. Cephalalgia 1994;14:451–457.

Sakai, F., Ebihara, S., Akiyama, M. and Horikawa, M., Pericranial muscle hardness in tension-type headache, Brain, 118 (1995) 523–531.

Schoenen, J., Jamart, B., Gerard, P., Lenarduzzi, P. and Delwaide, P. J., Exteroceptive suppression of temporalis muscle activity in chronic headache, Neurology, (1987); 37:1834–1836.

Schoenen J, Gerard P. De Pasqua V, Sianard-Gainko J. Multiple clinical and paraclinical analyses of chronic tension-type headache associated or unassociated with disorder of pericranial muscles. Cephalalgia (1991a); 11:135–139.

Schoenen J, Bottin D, Hardy F, Gerard P. Cephalic and extracephalic pressure pain thresholds in chronic tension-type headache. Pain (1991b); 47:145–149.

Shimoyama N, Shimoyama M, Davis A M, Inturrisi C E, Elliot K J. Spinal gabapentin is antinociceptive in the rat formalin test. Neurosci. Lett. (1997); 222:65–67

Southan, G. J. and Szabo, C., Selective pharmacological inhibition of distinct nitric oxide synthase isoforms, Biochemical Pharmacology, 4 (51) (1996) 383–394.

Torebjörk H E, La Motte R H, Robinson C J. Peripheral neural correlates of magnitude of cutaneous pain and hyperalgesia: simultaneous recordings in humans of sensory judgments of pain and evoked responses in nociceptors with C-fibers. J Neurophysiol (1984); 51:325–339.

Torebjörk, H. E., Lundberg, L. E. and LaMotte, R. H., Central changes in processing of mechanoreceptive input in capsaicin-induced secondary hyperalgesia in humans, J Physiol (Lond), (1992); 448:765–780.

Travell J G, Simons D G. Myofascial pain and dysfunction. The trigger point manual. Baltimore: Williams & Wilkins 1983.

Ulrich V, Russell M B, Jensen R. Olesen J. A comparision of tension-type headache in migraineurs and in non-migraineurs: a population-based study. Pain 1996;67:501–506.

Wall, P. D., The presence of ineffective synapses and the circumstances which unmask them, Philos Trans R Soc Lond Biol, (1977); 278:361–372.

Wall P D, Woolf C J. Muscle, but not cutaneous C-afferent input produces prolonged increases in the excitability of the flexion reflex in the rat. J Physiol (1984); 356:453–458.

Willer, J. C., Roby, A. and Le Bars, D., Psychophysical and electrophysiological approaches to the pain-relieving effects of heterotopic nociceptive stimuli, Brain, 107 (1984)1095–1112.

Woolf, C. J., Evidence for a central component of post-injury pain hypersensitivity, Nature, (1983); 306:686–688.

Woolf C J, King A E. Dynamic alterations in the cutaneous mechanoreceptive fields of dorsal horn neurons in the rat spinal cord. J Neurosci (1990); 10(8):2717–2726.

Woolf, C. J. and Thompson, S. W., The induction and maintenance of central sensitization is dependent on N-methyl-D-aspartic acid receptor activation; implications for the treatment of post-injury pain hypersensitivity states, Pain, (1991); 44:293–299.

Woolf, C. J., Shortland, P. and Coggeshall, R E., Peripheral nerve injury triggers central sprouting of myelinated afferents, Nature, (1992); 355:75–78.

Woolf, C. J., The dorsal horn: state-dependent sensory processing and the generation of pain. In: P. D. Wall and R. Melzack (Eds.), Textbook of pain, Third Edition, Churchill Livingstone, Edinburgh. (1994a) pp 101–112.

Woolf, C. J. and Doubell, T. P., The pathophysiology of chronic pain-increased sensitivity to low threshold A-b-fiber inputs, Curr Opin Neurobiol, (1994b); 4:525–534.

Woolf, C. J., Windup and central sensitization are not equivalent, Pain, (1996); 66:105–108.

Wänmann A, Agerberg G. Headache and dysfunction of the masticator; system in adolescents. Cephalalgia (1986); 6:247–55.

Wörz R, Lobisch M, Gessler M, Grotemeyer K H, Nehrfich D, May A, Schabet M, Schwittmann B. Flupirtine versus placebo in chronic tension-type headache. Headache Quaterly, 7(1):30–38.

Xiao W H, Bennett G J. Gabapentin relieves abnormal pain sensations via spinal site of action in a rat model of painful peripheral neuropathy. Pain, in press.

Yaksh, T. L. and Malmberg, A. B., Central pharmacology of nociceptive transmission. In: P. D. Wall and R Melzack (Eds.), Textbook of pain, Third Edition, Churchill Livingstone, Edinburgh. (1994) pp 165–200.

Yarnitsky D, Sprecher E, Zaslansky R, Hemli J A. Heat pain thresholds: normative data and repeatability. Pain 1995;60:329–332.

Yu, X. M. and Mense, S., Response properties and descending control of rat dorsal horn neurons with deep receptive fields, Neuroscience, (1990); 39:823–831.

Yu X. M, J W, Vernon H, Sessle B J. Temporomandibular inflammatory irritant induces increased activity of jaw muscles. J Dent Res (1992); 71:60

Yu X M, Sessle B J, Hu J W. Differential effects of cutaneous and deep application of inflammatory irritant on the mechanoreceptive field properties of trigeminal brain stem nociceptive neurons. J Neurophysiol (1993); 70:1704–1707.

Zhang, X., Ashton Miller, J. A. and Stohler, C. S., A closed-loop system for maintaining constant experimental muscle pain in man, IEEE Trans Biomed Eng, 40(1993) 344–352.

Østergaard, S., Russell, M. B., Bendtsen, L. and Olesen, J., Comparison of first degree relatives and spouses of people with chronic tension-type headache, BMJ, (1997); 314:1092–1093

What is claimed is:

1. A method for treatment of a tension-type headache in a person in need of such treatment, comprising administering an amount of an agent effective to interact with neuronal transmission connected with pain perception, so as to prevent or reduce central sensitization, which agent comprises an NMDA glutamate receptor antagonist or a prodrug thereof, with the proviso that said antagonist is not ethyl 2-amino-6-(4-fluorobeznylamino)-3-pyridylcarbamate, an arylglycinamide derivative as defined herein or amitriptyline.

2. A method according to claim 1, wherein the agent is an agent which is capable of substantially normalizing a pathological qualitatively altered stimulus-response function.

3. A method according to claim 1, wherein the agent is an agent which is capable of substantially normalizing a pathological abnormally low pain threshold.

4. A method according to claim 1, wherein the agent is an agent which is capable of substantially reducing a pathological increased pericranial muscle hardness.

5. A method according to claim 1, wherein the agent is an agent which is capable of substantially reducing a pathological increased pericranial myofascial tenderness.

6. A method according to claim 1, wherein the agent is an agent which is capable of substantially preventing or reducing pain, tenderness or hardness in pericranial muscle induced by experimental tonic muscle contraction, or normalizing a qualitatively altered stimulus-response function induced by experimental tonic muscle contraction, or normalizing a reduced pain threshold induced by experimental tonic muscle contraction.

7. A method according to claim 1, wherein the agent is an agent which is capable of substantially preventing or reducing pain, tenderness or hardness in pericranial muscle induced by intra muscular infusion of algogenic substances, or preventing or normalizing a qualitatively altered stimulus-response function induced by intra muscular infusion of algogenic substances or normalizing a reduced pain threshold induced by intra muscular infusion of algogenic substances.

8. A method according to claim 1, wherein the agent is an agent which is capable of substantially preventing or reducing pain, tenderness or hardness in pericranial muscle induced by stimulation of nociceptive afferents in myofascial tissues or preventing or normalizing a qualitatively altered stimulus-response function induced by stimulation of nociceptive afferents in myofascial tissues or normalizing a reduced pain threshold induced by stimulation of nociceptive afferents in myofascial tissues.

9. A method according to claim 1, wherein the agent is an agent which is capable of substantially preventing or reducing secondary allodynia or secondary hyperalgesia induced by stimulation of nociceptive afferents in myofascial tissues.

10. A method according to claim 1, wherein the agent is an agent which is capable of substantially preventing or reducing wind-up induced by repetitive stimulation of nociceptive afferents in the pericranial region.

11. A method according to claim 1, wherein the agent is an agent which is capable of substantially preventing or reducing secondary allodynia or secondary hyperalgesia induced by nociceptive input in an experimental animal model.

12. A method according to claim 1, wherein the agent is an agent which is capable of substantially preventing or reducing wind-up induced by repetitive stimulation of nociceptive afferents in an experimental animal model.

13. A method according to claim 1, wherein the agent is an agent which is capable of substantially preventing or reducing increased receptive field size of second order neurons induced by nociceptive input in an experimental animal model.

14. A method according to claim 1, wherein the agent is an agent which is capable of substantially preventing or reducing an increased excitability of the flexion reflex induced by nociceptive input in an experimental animal model.

15. A method according to claim 1, wherein the agent is an agent which is capable of substantially preventing or reducing central sensitization induced by nociceptive input in an experimental animal model.

16. A method according to claim 1 for treatment of tension-type headache in a person in need of such treatment, the patient having a qualitatively altered stimulus/response function in connection with nociception, comprising administering an amount of an agent effective to interact with neuronal transmission connected with pain perception, so as to obtain a substantial normalization of an otherwise qualitatively altered stimulus/response function in connection with nociception.

17. A method according to claim 1, wherein the treatment of tension-type headache is not accompanied by a substantial reduction of muscle tension.

18. A method according to claim 1, wherein the interaction comprises interaction with neuronal transmission connected with second order nociceptive neurons.

19. A method according to claim 1, wherein the interaction comprises a reduction of input to second order nociceptive neurons.

20. A method according to claim 1, which comprises administering an agent in an amount effective to alleviate said headache, said agent being an agent capable of altering the relationship of pain intensity to pressure intensity when the trapezoid muscle is palpated at different pressure intensities in said person.

21. A method according to claim 20 wherein the relationship is substantially linear in the untreated persons, and substantially non-linear in the treated persons.

22. A method according to claim 21, wherein the relationship is positively accelerating in the treated person.

23. A method according to claim 22, wherein the rate of acceleration of pain intensity with pressure intensity is substantially constant.

24. A method according to claim 23, wherein the relationship in the treated persons is substantially the same as in control persons who did not have tension-type headache and who were treated with a placebo.

25. A method according to claim 1, wherein the interaction is one which in a panel of test persons suffering from increased myofascial tenderness with disorder of pericranial muscle in connection with tension-type headache will transform a substantially linear pain intensity perception in response to pressure intensity in trapezius muscle into a curve (C) of which the values of pain intensity are lower than the linear pain intensity perception and wherein the curve (C) can be described substantially as a power function and is a curve which is substantially linear in a double logarithmic plot and wherein substantially each of the values of curve (C) is at the most 20% higher than the value of the corresponding curve produced for a test panel of healthy controls.

26. A method according to claim 25, wherein substantially each of the values of curve (C) is at the most 10% higher than the value of the corresponding curve produced for a test panel of healthy controls.

27. A method according to claim 1, wherein the interaction is effected by administering an effective amount of an agent interacting with neuronal transmission connected with pain perception, the administration being performed substantially at least once daily and being continued for a period of at least one month.

28. A method according to claim 27, wherein the administration is being continued for a period of at least one month and less than 10 years.

29. A method according to claim 27, wherein the administration is being continued for a period of at least one month and less than 5 years.

30. A method according to claim 27, wherein the administration is being continued for a period of at least one month and less than 2 years.

31. A method according to claim 27, wherein the administration is being continued for a period of at least one month and less than 1 year.

32. A method for treatment of tension-type headache in a person in need of such treatment, comprising administering an amount of an agent which, in the peripheral and/or central nervous system, is effective to specifically interact with neuronal transmission connected with pain perception by substantially antagonizing the action of glutamate on the NMDA receptor, with the proviso that said agent is not ethyl 2-amino-6-(4-fluorobenzylamino)-3-pyridylcarbamate, an arylglycinamide derivative as defined herein, or amitriptyline.

33. A method according to claim 32, wherein the agent is an agent capable of interacting with neuronal transmission connected with pain perception, so as to obtain a substantial normalization of a qualitatively altered stimulus/response function in connection with nociception.

34. A method according to claim 1, wherein the agent is an agent which, in the peripheral and/or central nervous system, is capable of substantially inhibiting the production of glutamate or substantially inhibiting the release of glutamate.

35. A method according to claim 1, wherein the agent comprises a competitive NMDA glutamate receptor antagonist.

36. A method according to claim 35, wherein the antagonist is a nitrogen-containing heterocyclic compound selected from the group consisting of diacidic piperidines, diacidic piperazines and phosphono amino acids.

37. A method according to claim 1, wherein the agent comprises a non-competitive NMDA glutamate receptor antagonist.

38. A method according to claim 37, wherein the antagonist is selected from a group consisting of polycyclic amines, tricyclic antidepressants, adamantanamines, arylcyclohexylamines, arylcyclohexylamines, opioid derivatives, glycylamides, piperidinylethanols, piperidinylethanols, diguanidines, g-aminobutyric acid derivatives, polycyclic amines.

39. A method according to claim 1, wherein the antagonist is a tricyclic antidepressant.

40. A method according to claim 1, wherein the antagonist is selected from the group consisting of γ-aminobutyric acid derivatives and polycyclic amines.

41. The method of claim 1 in which the agent is mirtazapine or a pharmaceutically acceptable salt or derivative thereof.

42. The method of claim 1 in which the agent is mirtazapine or a pharmaceutically acceptable salt thereof.

43. The method of claim 42 in which the tension-type headache is an episodic tension-type headache.

44. The method of claim 42 in which the tension-type headache is a chronic tension-type headache.

45. The method of claim 36 in which the agent is CGS 19755, (R)-CPP, (R)-CPPene, or LY 235959.

46. The method of claim 39 in which the agent is Metapramine, Imipramine, Desipramine, Mirtazapine or Venlafaxine.

47. A method for treatment of a tension-type headache in a person in need of such treatment, comprising administering to said person a therapeutically effective amount of mirtazapine or a pharmaceutically acceptable salt thereof.

48. The method of claim 47 in which the tension-type headache is an episodic tension-type headache.

49. The method of claim 47 in which the tension-type headache is a chronic tension-type headache.

50. The method of claim 1 wherein the agent comprises an NMDA glutamate receptor antagonist.

51. A method according to claim 1, wherein the agent is an agent which, in the peripheral and/or central nervous system, is capable of substantially inhibiting the binding of glutamate to receptors for glutamate.

* * * * *